United States Patent
Aberger et al.

(10) Patent No.: US 10,633,369 B2
(45) Date of Patent: *Apr. 28, 2020

(54) METHOD OF INHIBITING DYRK1B

(71) Applicant: 4 SC AG, Planegg-Martinsried (DE)

(72) Inventors: Fritz Aberger, Salzburg (AT); Wolfgang Gruber, Salzburg (AT); Johann Leban, Vienna (AT); Hella Kohlhof, Munich (DE); Daniel Vitt, Germering (DE); Roland Baumgartner, Planegg-Martinsried (DE)

(73) Assignee: 4 SC AG, Planegg-Martinsried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/915,626

(22) Filed: Mar. 8, 2018

(65) Prior Publication Data

US 2018/0201606 A1    Jul. 19, 2018

Related U.S. Application Data

(62) Division of application No. 14/307,533, filed on Jun. 18, 2014, now Pat. No. 9,951,050.

(30) Foreign Application Priority Data

Jun. 8, 2013  (EP) .................................... 13172575

(51) Int. Cl.
 *C07D 403/12* (2006.01)
 *A61K 31/00* (2006.01)
 *A61K 31/506* (2006.01)
 *A61P 35/00* (2006.01)

(52) U.S. Cl.
 CPC ............ *C07D 403/12* (2013.01); *A61K 31/00* (2013.01); *A61K 31/506* (2013.01); *A61P 35/00* (2018.01)

(58) Field of Classification Search
 CPC .... A61K 31/00; A61K 31/506; C07D 403/12; A61P 35/00
 See application file for complete search history.

(56) References Cited

U.S. PATENT DOCUMENTS

| 8,362,023 B2 | 1/2013 | Liu et al. |
| 9,951,050 B2 * | 4/2018 | Aberger ................ A61K 31/00 |
| 10,005,769 B2 * | 6/2018 | Leban ................ C07D 417/14 |
| 2012/0184508 A1 | 7/2012 | Liu et al. |
| 2012/0184548 A1 | 7/2012 | Dominique et al. |

FOREIGN PATENT DOCUMENTS

WO    2013026806 A1    2/2013

OTHER PUBLICATIONS

Ashford et al., "A novel DYRK1B inhibitor AZ191 demonstrates that DYRK1B acts independently of GSK3β to phosphorylate cyclin D1 at Thr286, not Thr288", 2014, Biochemical Journal, 457(1), pp. 43-56. (Published online as BJ Immediate Publication on Oct. 2013) (Year: 2014).*
Partial European Search Report related to corresponding European Patent Application No. EP13172575 dated Feb. 10, 2014.
Holohan et al., "Cancer drug resistance: an evolving paradigm", 2013, Nature Reviews Cancer, vol. 13, No. 10, pp. 714-726.

* cited by examiner

*Primary Examiner* — My-Chau T. Tran
(74) *Attorney, Agent, or Firm* — Millen White Zelano and Branigan, PC; Csaba Hunter

(57) ABSTRACT

The present invention relates to a DYRK1B inhibitor for use in the treatment of cancer, wherein in said cancer and/or in cells of said cancer the hedgehog signaling pathway is activated, and in particular the activation of the hedgehog signaling pathway is independent of signaling by the G protein-coupled receptor Smoothened.

14 Claims, 13 Drawing Sheets

Specification includes a Sequence Listing.

L3.6pl

SEQUENCE LISTING

<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tctggacata ccccacctcc ctctg                                        25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
actgcagctc ccccaatttt tctgg                                        25

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcctcgtgtg cgctgtcttc cttc                                         24

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgtcagaaag gccaaagcaa cgtga                                        25

```
<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Arg Arg Phe Arg Pro Ala Ser Pro Leu Arg Gly Pro Pro Lys
1               5                   10                  15

<210> SEQ ID NO 6
<211> LENGTH: 7
<212> TYPE: PRT
<213> ORGANISM: Homo sapiens

<400> SEQUENCE: 6

Phe Glu Leu Leu Ser Tyr Asn
1               5

<210> SEQ ID NO 7
<211> LENGTH: 4
<212> TYPE: PRT
<213> ORGANISM: Homo sapiens

<400> SEQUENCE: 7

Val Asp Phe Gly
1
```

METHOD OF INHIBITING DYRK1B

SEQUENCE LISTING

The instant application contains a Sequence Listing which has been submitted electronically in ASCII format and is hereby incorporated by reference in its entirety. Said ASCII copy, created on Jun. 17, 2014, is named BOEHMERP-0207_SL.txt and is 1,746 bytes in size.

BACKGROUND OF THE INVENTION

The Dual-Specificity-Tyrosine-Regulated Kinase 1B (DYRK1B, also known as Minibrain-Regulated Kinase MIRK) belongs to the DYRK family of serine/threonine kinases, which, based on sequence and structural homologies, can be divided into three subgroups: the YAK group with no members in the animal kingdom, the DYRK1 and the DYRK2 subgroup. The two DYRK1 subgroup members DYRK1A and DYRK1B share 85% identity at the amino acid level, though expression and functional characteristics are distinct (Aranda et al., 2011).

The human DYRK1B gene encodes a 69 kDa protein with 629 amino acids in length. Alternative splicing and differential promoter engagement can yield two additional, slightly shorter DYRK1B isoforms with differential expression patterns, the shorter of which lacking kinase activity (Leder et al., 2003).

The regulation of DYRK1B catalytic activity and function is not entirely understood. Given the extensive sequence similarity to DYRK1A, the intrinsic regulatory and catalytic properties of DYRK1B can, to a certain extent, be inferred from studies of DYRK1A regulation. DYRK family members are arginine-directed serine/threonine kinases, with DYRK1B phosphorylating either serine in the consensus substrate sequence SPSxxR (Friedman, 2007; Himpel et al., 2000). Activation of DYRK1B involves an intramolecular tyrosine (Y) auto-phosphorylation of the second tyrosine of an YxY motif in the conserved kinase domain and activation loop, respectively (Becker and Sippl, 2011; Himpel et al., 2000; Nolen et al., 2004). Notably, this Y-phosphorylation-dependent activation step occurs only during translation of DYRK kinases, resulting in activated DYRK proteins with Ser/Thr kinase activity (Lochhead et al., 2005). This implies that additional processes including protein-protein interactions, further post-translational modifications and/or subcellular localization control the response of DYRK kinases to extracellular signals. For instance, signaling via RAS/RAC/MKK3 is able to stimulate DYRK1B activity in certain cellular contexts such as in pancreatic cancer cells and interaction of DYRK1A with 14-3-3 proteins significantly enhances DYRK kinase activity (Deng et al., 2003; Jin et al., 2005; Jin et al., 2007; Kim et al., 2004; Lim et al., 2002).

During normal development DYRK1B expression is preferentially restricted to testes and muscle cells (Leder et al., 2003; Leder et al., 1999). In muscle its expression is regulated by RHO and basic Helix-Loop-Helix transcription factors via binding to an E-box in the DYRK1B promoter (Deng et al., 2003; Friedman, 2007). Inhibition and overexpression studies suggest a pro-differentiation activity of DYRK1B in myoblast differentiation by enhancing the expression of myogenic transcription factors such as Mef2 (Deng et al., 2005). This effect is mediated by DYRK1B-dependent phosphorylation of class II histone deacetylases (HDAC) thereby freeing Mef2 from complexes with inhibitory HDACs and allowing Mef2 to exert its pro-myogenic function (Deng et al., 2005). In addition to its role in myoblast differentiation, DYRK1B also controls cell cycle arrest by phosphorylation-dependent destabilization of D-type cyclins and stabilization of cell cycle inhibitors including p27 and p21 (Deng et al., 2004; Ewton et al., 2011; Mercer et al., 2005; Zou et al., 2004). Like DYRK1A, for which a larger number of substrate proteins has already been identified, DYRK1B can act as co-activator of the FOXO1a transcription factor, thereby regulating glucose-6-phosphatase expression (von Groote-Bidlingmaier et al., 2003).

DYRK1B deficient mice do not display any evident developmental defects and survive several weeks post birth (Leder et al., 2003). Details of the DYRK1B mutant phenotype remain to be reported. By contrast, DYRK1A deficiency in mice results in an embryonic lethal phenotype (Fotaki et al., 2002).

DYRK1B in Cancer

Several recent studies have implicated DYRK1B as a putative oncogenic factor in different cancer entities. DYRK1B localizes to the chromosomal region 19q13, which is frequently amplified in pancreatic and ovarian cancers (Friedman, 2007; Karhu et al., Genes Chromosomes Cancer. 2006 August; 45(8):721-730; Lee et al., 2000). Accordingly, DYRK1B is strongly expressed in a fraction of pancreatic and ovarian cancer cell lines (Friedman, 2007; Hu and Friedman, 2010). Notably, in pancreatic cancer DYRK1B acts as survival effector kinase downstream of RAS-RAC1 to promote viability and clonal growth of cancer cells (Jin et al., 2007). In addition, several in vitro studies suggest that DYRK1B has pro-oncogenic function in colon cancer, osteosarcoma and rhabdomyosarcoma (RMS). RNA interference and overexpression studies demonstrated a pro-survival role of DYRK1B in colon cancer, osteosarcoma, RMS and pancreatic cancer (Deng et al., 2009; Deng et al., 2006; Friedman, 2011; Jin et al., 2007; Mercer et al., 2006; Yang et al., Carcinogenesis. 2010 April; 31(4):552-558). The pro-survival activity in sarcoma can—at least in part—be ascribed to the role of DYRK1B in promoting the inactivation of reactive oxygen species (ROS). DYRK1B is able to increase the expression of ROS detoxifying enzymes including superoxide dismutases 2 and 3 (Deng et al., 2009; Hu and Friedman, 2010). This may also explain the enhanced sensitivity of DYRK1B-depleted cancer cells to certain chemotherapeutic drugs such as cisplatin known to increase toxic ROS levels (Hu and Friedman, 2010). Recently published results indicate that meningioma, in particular Non-NF2 Meningioma, may also depend on DYRK1B activity e.g. due to mutations in factors such as TRAF7, KLF4, AKT1, and/or SMO (Clark, V. E. et al., Science, 2013 Jan. 24, Epub ahead of print, PMID (PubMed-ID) 23348505—as supplied by publisher; Aavikko M. et al., Am J Hum Genet, 2012 Sep. 7, 91(3), 520-526; Kijima C. et al., Fam Cancer. 2012 Dec. 11(4), 565-570).

Hedgehog Signaling in Cancer Therapy

The Hedgehog (HH)/GLI signal transduction pathway is a key regulator of multiple developmental processes. Uncontrolled activation of HH/GLI signaling is a common feature of many human malignancies including cancers of the brain, skin, gastro-intestinal tract, prostate, breast lung, muscle and bone (reviewed in (Beachy et al., 2004a, b; Epstein, 2008; Kasper et al., 2012; Kasper et al., 2006; Merchant and Matsui, 2010; Ng and Curran, 2011; Ruiz i Altaba et al., 2007; Ruiz i Altaba et al., 2002; Scales and de Sauvage, 2009; Teglund and Toftgard, 2010; Theunissen and de Sauvage, 2009).

Precise reversible regulation of Hedgehog signaling is a complex process and mandatory for proper normal development of invertebrate and vertebrate organisms (for detailed reviews see (Huangfu and Anderson, 2006; Ingham and McMahon, 2001; Teglund and Toftgard, 2010)). In the absence of HH ligand, HH signaling is repressed by the activity of the HH receptor Patched (PTCH), a twelve-transmembrane domain protein whose intracellular localization is concentrated at the base of the primary cilium, a single antenna-like cell surface compartment that coordinates HH signal transduction. Unliganded PTCH prevents the translocation of the G-protein coupled receptor-like protein and essential pathway effector Smoothened into the primary cilium (Corbit et al., 2005; Rohatgi et al., 2007; Rohatgi and Scott, 2007). This leads to proteolytic cleavage of the latent zinc finger transcription factors GLI3—and to some extent also of GLI2—into C-terminally truncated repressor forms ($GLI^R$). $GLI^R$ formation involves preceding and sequential phosphorylation by protein kinase A (PKA), glycogen synthase kinase 3-beta (GSK) and casein kinase I (CKI) (Price and Kalderon, 2002) as well as a functional primary cilium (Smith and Rohatgi, 2011; Wang et al., 2000; Wen et al., 2010; Wong et al., 2009). Following processing, $GLI^R$ translocates to the nucleus to bind to HH target gene promoters and repress target gene expression (Aza-Blanc and Kornberg, 1999; Aza-Blanc et al., 1997). GLI signals are also negatively regulated by proteasome-mediated degradation of GLI and by binding to Suppressor of Fused (SUFU), which sequesters GLI proteins in the cytoplasm and also contributes to GLI processing in the primary cilium (Humke et al., 2010; Kogerman et al., 1999).

The therapeutic relevance of targeting HH/GLI signaling in human cancers with genetic, ligand-independent activation of HH/GLI signaling has recently been demonstrated for BCC and medulloblastoma. In both malignant entities, inhibition of the essential HH pathway effector Smoothened had a dramatic therapeutic benefit (Rudin et al., 2009; Skvara et al., 2011; Von Hoff et al., 2009). Whether Smoothened antagonists will display therapeutic efficacy in HH ligand dependent cancers remains to be shown. Ongoing clinical trials with Smoothened antagonists from different pharmaceutical companies will eventually answer the question of the clinical efficacy of targeting Smoothened in Hedgehog associated malignancies (Aberger et al., 2012; Lin and Matsui, 2012; Ng and Curran, 2011; Scales and de Sauvage, 2009). Clinical studies with small molecule Smoothened inhibitors to treat patients with metastatic colorectal cancer, ovarian cancer or pancreatic cancer failed to demonstrate therapeutic efficacy of Smoothened antagonists in combination with currents treatment regimens (Ng and Curran, 2011). One of the reasons for the lack of therapeutic efficacy of Smoothened inhibitors may be explained by Smoothened-independent activation of GLI transcription factors in different cancer entities such as pancreatic cancer, melanoma or Ewing's sarcoma. This non-canonical activation of GLI transcription factors can be induced by a variety of signals frequently hyperactive in malignant cells including TGF-b/SMAD, RAS-MEK/ERK, PI3K/AKT, EGFR signaling or the EWS-FLI1 oncogene (reviewed in Aberger et al., 2012; Mangelberger et al., 2012; Stecca and Ruiz, 2010).

Regulation of HH/GLI Signaling by DYRK Family Members

The first regulatory interactions between DYRK family members and the HH/GLI pathway came from studies of DYRK1A and its impact on the transcriptional activity of the GLI zinc finger transcription factors mediating the transcriptional output of HH pathway activation. Using reporter gene based assays, Mao et al. have shown that DYRK1A is able to enhance the activity of the GLI1 activator and stimulate HH target gene expression, respectively. DYRK1A can phosphorylate GLI1 in vitro and enhance the nuclear level of GLI1. Direct modification of GLI1 and enhanced nuclear localization in response to DYRK1A activity are likely to account for the enhanced expression of HH target genes (Mao et al., 2002).

While DYRK1A enhances GLI activity, the class II DYRK family member DYRK2 acts as negative regulator of GLI activity. DYRK2 can directly phosphorylate GLI2 and GLI3 resulting in destabilization of GLI2/3 and enhanced proteasome-dependent degradation.

Mutation of the DYRK2 substrate phosphorylation sites S384 and S1011 in GLI2 rendered GLI2 resistant to DYRK2 mediated inhibition of transcriptional activity and proteasomal degradation (Varjosalo et al., 2008).

Analysis of DYRK1B function in HH-unresponsive RAS mutant pancreatic cancer cells revealed another regulatory mechanism by which DYRK kinases can affect the activity of HH signaling. Lauth et al. (2010) provide evidence that DYRK1B is involved in an autocrine-to-paracrine shift of HH signaling triggered by mutant RAS. This study suggests that oncogenic RAS signaling in pancreatic cancer cells increases HH ligand expression though at the same time it also prevents autocrine HH pathway activation (Lauth et al., 2010). RAS signaling therefore contributes to paracrine HH signaling, with tumor cells representing the signal source and adjacent stroma cells the signal-receiving compartment (Yauch et al., 2008). Like RAS, expression of the RAS effector DYRK1B in HH activated mouse fibroblasts inhibited HH signaling, suggesting that DYRK1B can act downstream of RAS to prevent autocrine HH signaling. Further, RNAi knockdown of RAS and DYRK1B in RAS mutant pancreatic cancer cells both led to a GLI2-dependent increase in GLI1 mRNA expression (Lauth et al., 2010). The detailed mechanisms of HH pathway inhibition by DYRK1B remain unknown.

Together, these reports suggest that DYRK2 and DYRK1B can have a repressive effect on HH/GLI signaling while DYRK1A functions as positive regulator of GLI transcriptional activity.

SMO targeting is a valid approach for the treatment of cancer entities involving canonical Hedgehog signaling such as BCC and medulloblastoma. However, rapid resistance development to SMO inhibitors as well as non-canonical SMO-independent activation of oncogenic GLI (e.g. in pancreatic cancer, esophageal carcinoma and Ewing's sarcoma) confers severe constraints to the therapeutic application of SMO inhibitors. Further, multiple oncogenic signals including RTK, MAPK and PI3K pathways promote oncogenic GLI function independent of SMO. Thus, there is a high medical need for the identification of drug targets downstream of SMO (and therefore independent of SMO activation) for the rational design of GLI intervention strategies. This would open up the opportunity for the design of novel anti-GLI drugs with a clear medical benefit for the treatment of SMO-dependent and the many SMO-independent or SMO-inhibitor resistant cancers.

REFERENCES

Aberger, F. et al. (2012). Vitam Horm 88, 25-54; Aranda, S. et al. (2011) FASEB 25, 449-462; Aza-Blanc, P. and Kornberg, T. B. (1999) Trends Genet 15, 458-462; Aza-Blanc, P. et al. (1997) Cell 89, 1043-1053; Beachy, P. A. et al. (2004a) Nature 431, 402; Beachy, P. A., et al. (2004b) Nature 432, 324-331; Becker, W. and Sippl, W. (2011) The FEBS journal 278, 246-256; Bruns, C. J. et al. (1999)

Neoplasia 1, 50-62; Chen, J. K. et al. (2002) PNAS 99, 14071-14076; Corbit, K. C. et al. (2005) Nature 437, 1018-1021; Deng, X. et al. (2009) Cancer research 69, 3317-3324; Deng, X. et al. (2006) Cancer research 66, 4149-4158; Deng, X. et al. (2005) J Biol Chem 280, 4894-4905; Deng, X. et al. (2003) J Biol Chem 278, 41347-41354; Deng, X. et al. (2004) J Biol Chem 279, 22498-22504; Eberl, M. et al. (2012) EMBO molecular medicine 4, 218-233; Epstein, E. H. (2008). Nat Rev Cancer 8, 743-754; Ewton, D. Z. et al. (2011) Molecular cancer therapeutics 10, 2104-2114; Fotaki, V. et al. (2002) Molecular and cellular biology 22, 6636-6647; Friedman, E. (2007) Journal of cellular biochemistry 102, 274-279; Friedman, E. (2011) Sarcoma 2011, 260757, doi:10.1155/2011/260757; Himpel, S. et al. (2000). J Biol Chem 275, 2431-2438; Hu, J., and Friedman, E. (2010) Genes & cancer 1, 803-811; Huangfu, D., and Anderson, K. V. (2006) Development 133, 3-14; Humke, E. W. et al. (2010) Genes & development 24, 670-682; Ingham, P. W., and McMahon, A. P. (2001) Genes & development 15, 3059-3087; Jin, K. et al. (2005) J Biol Chem 280, 42097-42105; Jin, K. et al. (2007) Cancer research 67, 7247-7255; Karhu, R. et al. (2006) Genes, chromosomes & cancer 45, 721-730; Kasper, M. et al. (2012) The Journal of clinical investigation 122, 455-463; Kasper, M. et al. (2007) Methods in molecular biology 397, 67-78; Kasper, M. et al. (2006) Eur J Cancer 42, 437-445; Kim, D. et al. (2004) Biochem Biophys Res Commun 323, 499-504; Kogerman, P. et al. (1999) Nat Cell Biol 1, 312-319; Lauth, M. et al. (2010) Nat Struct Mol Biol 17, 718-725; Leder, S. et al. (2003) Biochem J 372, 881-888; Leder, S. et al. (1999) Biochemical and biophysical research communications 254, 474-479; Lee, K. et al. (2000) Cancer research 60, 3631-3637; Lim, S. et al. (2002) J Biol Chem 277, 25040-25046; Lin, T. L., and Matsui, W. (2012) OncoTargets and therapy 5, 47-58; Lochhead, P. A. et al. (2005) Cell 121, 925-936; Mangelberger, D. et al. (2012) Front Biosci 17, 90-99; Mao, J. et al. (2002) J Biol Chem 277, 35156-35161; Mercer, S. E. et al. (2005) J Biol Chem 280, 25788-25801; Mercer, S. E. et al. (2006) Cancer research 66, 5143-5150; Merchant, A. A., and Matsui, W. (2010) Clinical cancer research 16, 3130-3140; Ng, J. M., and Curran, T. (2011) Nat Rev Cancer 11, 493-501; Nolen, B. et al. (2004) Molecular cell 15, 661-675; Price, M. A., and Kalderon, D. (2002) Cell 108, 823-835; Rohatgi, R. et al. (2007) Science 317, 372-376; Rohatgi, R., and Scott, M. P. (2007) Nat Cell Biol 9, 1005-1009; Rudin, C. M. et al. (2009) N Engl J Med 361, 1173-1178; Ruiz i Altaba, A., et al. (2007) Trends Cell Biol 17, 438-447; Ruiz i Altaba, A. et al. (2002) Nat Rev Cancer 2, 361-372; Scales, S. J., and de Sauvage, F. J. (2009) Trends Pharmacol Sci 30, 303-312; Skvara, H. et al. (2011) J Invest Dermatol 131, 1735-1744; Smith, E. F., and Rohatgi, R. (2011) Science signaling 4, mr1; So, P. L. et al. (2006) Experimental dermatology 15, 742-750; Stecca, B., and Ruiz, I. A. A. (2010) J Mol Cell Biol 2, 84-95; Teglund, S., and Toftgard, R. (2010) Biochim Biophys Acta 1805, 181-208; Theunissen, J. W., and de Sauvage, F. J. (2009) Cancer research 69, 6007-6010; Varjosalo, M. et al. (2008) Cell 133, 537-548; von Groote-Bidlingmaier, F. et al. (2003) Biochem Biophys Res Commun 300, 764-769; Von Hoff, D. D. et al. (2009) N Engl J Med 361, 1164-1172; Wang, B. et al. (2000) Cell 100, 423-434; Wen, X. et al. (2010) Molecular and cellular biology 30, 1910-1922; Wong, S. Y. et al. (2009) Nat Med 15, 1055-1061; Yang, C. et al. (2010) Carcinogenesis 31, 552-558; Yauch, R. L. et al. (2008) Nature 455, 406-410; Zou, Y. et al. (2004) J Biol Chem 279, 27790-27798.

BRIEF SUMMARY OF THE INVENTION

The various and partially opposing functions of DYRK kinases reported previously prompted the present inventors to carefully study the specific involvement of said kinases in oncogenic HH signaling, with a focus on DYRK1 kinases. The impact of DYRK1A and DYRK1B on HH signal activity was re-addressed using an array of cellular in vitro and in vivo test systems including SMO-dependent and SMO-independent model systems from different species.

The present invention relates to a method of treating cancer in a patient suffering from cancer, said method comprising administering a therapeutically effective amount of a DYRK1B inhibitor to said patient.

The present invention further relates to a DYRK1B inhibitor for use in the treatment of cancer.

The present invention further relates to the use of a DYRK1B inhibitor for producing a medicament for the treatment of cancer.

The present invention further relates to a pharmaceutical combination comprising a DYRK1B inhibitor, in particular for use in the treatment of cancer.

The present invention further relates to a cancer medicament comprising a DYRK1B inhibitor.

The present invention further relates to a method of inhibiting DYRK1B in vitro, a method of inhibiting DYRK1B in a mammal, a method of inhibiting the hedgehog signaling pathway in a mammal, and a method of preventing the formation of resistance of cancer cells against chemotherapeutic agents in a patient suffering from cancer, all of which are detailed further herein below.

DETAILED DESCRIPTION OF THE INVENTION

In certain embodiments, the present invention relates to the matter enumerated in the following items:
1. A DYRK1B inhibitor for use in the treatment of cancer, wherein in said cancer and/or in cells of said cancer the hedgehog signaling pathway is activated.
2. The DYRK1B inhibitor according to item 1, wherein said cancer and/or cells of said cancer do not respond to Smoothened inhibitor therapy.
3. The DYRK1B inhibitor according to any of items 1 or 2, wherein in said cancer and/or in cells of said cancer the activation of the hedgehog signaling pathway is independent of signaling by the G protein-coupled receptor Smoothened.
4. The DYRK1B inhibitor according to any of items 1 to 3, wherein said cancer is not responsive to inhibition of the G protein-coupled receptor Smoothened.
5. The DYRK1B inhibitor according to any of items 1 to 4, wherein in said cancer and/or in cells of said cancer the G protein-coupled receptor Smoothened is not responsive to inhibition by Smoothened inhibitors.
6. The DYRK1B inhibitor according to any of items 1 to 5, wherein said cancer is selected from the group comprising cancer of the breast, esophagus, gastrointestinal tract, gastro-intestinal stromal tumors, pancreas, prostate, biliary tract, bladder, basal cell carcinoma, medulloblastoma, rhabdomyosarcoma, glioma, small-cell lung cancer, oral squamous cell carcinoma, melanoma, colorectal cancer, non-small cell lung cancer, osteosarcoma, glioblastoma, chronic lymphacytic leukemia, chronic myeloid leukemia, multiple myeloma, acute myeloid leukemia, ovarian cancer, meningioma, particularly Non-NF2 Meningiomas, and liver cancer.
7. The DYRK1B inhibitor of any of items 1 to 6, wherein said DYRK1B inhibitor is a small molecule.

8. The DYRK1B inhibitor of any of items 1 to 7, wherein said DYRK1B inhibitor is a compound of the below formula (I):

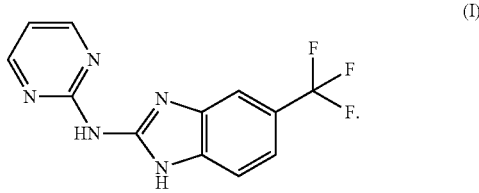 [SMILES: FC(F)(F)c1ccc2[nH]c(Nc3ncccn3)nc2c1]

In the method of item 1, said method can in certain embodiments comprise inhibiting the expression of a gene encoding for DYRK1B, wherein more particularly the expression of said gene is inhibited on the DNA level and/or on the RNA level.

9. The DYRK1B inhibitor of any of items 1 to 10, wherein said patient is a human.
10. The DYRK1B inhibitor of any of items 1 to 11, wherein cancer stem cells are inhibited in said cancer.
11. A method of inhibiting DYRK1B in vitro, said method comprising adding a DYRK1B inhibitor to a sample comprising cancer cells wherein the hedgehog signaling pathway is activated.

In certain embodiments the DYRK1B inhibitor is added in an amount which is effective to inhibit DYRK1B by at least 50%, more particularly at least 75%, even more particularly at least 90% in said sample. This can be determined via determining the expression level of a target gene of the Hedgehog signaling pathway via the methods described herein, e.g. qPCR or Western Blot.

12. A DYRK1B inhibitor for use in therapy for preventing the formation of resistance of cancer cells against chemotherapeutic agents in a patient suffering from cancer, wherein in said cancer and/or in cells of said cancer the hedgehog signaling pathway is activated.

In principle, in the embodiments of the present invention, the DYRK1B inhibitor can be any molecule which inhibits DYRK1B. In certain embodiments of the present invention, the DYRK1B inhibitor is selected from the group comprising the compound of the above formula (I), harmine, and the shRNA targeting DYRK1B (shDYRK1B) as described herein, particularly the compound of the above formula (I).

In particular embodiments of the present invention, in said cancer, the hedgehog signaling pathway is activated.

In particular embodiments of the present invention, in cells of said cancer, the hedgehog signaling pathway is activated.

In further particular embodiments of the present invention, said cancer does not respond to Smoothened inhibitor therapy.

In further particular embodiments of the present invention, cells of said cancer do not respond to Smoothened inhibitor therapy.

In further particular embodiments of the present invention, in said cancer the activation of the hedgehog signaling pathway is independent of signaling by the G protein-coupled receptor Smoothened.

In further particular embodiments of the present invention, in cells of said cancer the activation of the hedgehog signaling pathway is independent of signaling by the G protein-coupled receptor Smoothened.

In further particular embodiments of the present invention, in said cancer the G protein-coupled receptor Smoothened is not responsive to inhibition by Smoothened inhibitors.

In further particular embodiments of the present invention, in cells of said cancer the G protein-coupled receptor Smoothened is not responsive to inhibition by Smoothened inhibitors.

In the context of the present invention, said cancer or cells of said cancer being not responsive to Smoothened inhibitor therapy includes both the case that the activation of the hedgehog signaling pathway is independent of signaling by the G protein-coupled receptor Smoothened, and that the G protein-coupled receptor Smoothened is not responsive to inhibition by Smoothened inhibitors.

In the present invention patients wherein in said cancer, or in cells of said cancer, the hedgehog signaling pathway is activated are in short referred to as "Hedgehog dependent patients", and patients wherein in said cancer, or in the cells of said cancer, the hedgehog signaling pathway is not activated are in short referred to as "Hedgehog independent patients". In the present invention, patients e.g. can be stratified into Hedgehog dependent patients and Hedgehog independent patients by a procedure comprising the steps of
1) providing a sample from said patient, wherein said sample comprises cancer cells from said patient,
2) optionally subjecting said sample to a work-up step,
3) adding a labeled antibody which specifically binds to at least one protein playing a role in the hedgehog signaling pathway,
   or
   adding a first antibody which specifically binds to at least one protein playing a role in the hedgehog signaling pathway, and subsequently adding a second antibody which specifically binds to said first antibody, and wherein said second antibody is a labeled antibody,
4) washing said sample after step 3,
5) determining whether said labeled antibody is detectable in said sample after step 4),
6) if in step 5) said marker moiety is detectable, classifying said patient as Hedgehog dependent patient, and if in step 5) said marker moiety is not detectable, classifying said patient as Hedgehog independent patient.

Antibodies used in the present invention are typically monoclonal antibodies.

The label in said labeled antibody can be selected from any label typically used as antibody label in the field of biochemistry, cellular biology, immunochemistry, etc., for a label selected from the group comprising a fluorescence label, a dye, a FRET label, a radioactive label, moiety, or an enzymatically active moiety. Said enzymatically active moiety can process a reaction which in turn results in the release of a detectable substance, e.g. a dye.

In the above method of stratifying patients into Hedgehog dependent patients and Hedgehog independent patients, the work-up step is e.g. in particular embodiments selected from the group comprising preservation, embedding, slicing and staining. Preservation can be performed by cryopreservation or fixation by e.g. formaldehyde or ethanol. Embedding the tumor material prepares it for slicing. Staining can be performed with direct or indirect methods. For further information and examples see DOI: 10.1354/vp.42-4-405 J. A. Ramos-Vara, Technical Aspects of Immunohistochemistry, (2005) 42: 405 Vet Pathol.

In the context of the present invention, the expression "said labeled antibody is not detectable" means that by the state of the art measurement methods used for detecting said label, no signal relating to said label is detectable, and/or said signal is not significant in relation to the background noise generated by said measurement method.

In the above method to stratify patients into Hedgehog dependent patients and Hedgehog independent patients, washing step 4 is to remove unbound and/or unspecifically bound antibodies from step 3. In particular embodiments, said washing step comprises washing with a buffer, e.g. a PBS buffer, and optionally a serum protein, e.g. BSA. Washing step 4 can be repeated as necessary to obtain a suitable signal/noise ratio, e.g. 2 or more, 3 or more, 4 or more times.

In certain embodiments of the above method to stratify patients into Hedgehog dependent cancer patients and Hedgehog independent cancer patients, background signal by unspecific binding of antibodies is excluded by an isotype control. This control can be utilized when working with monoclonal primary antibodies. A comparative sample treated as above is incubated with antibody diluent, supplemented with a non-immune immunoglobulin of the same isotype (for example, $IgG_1$, $IgG2_A$, $IgG2_B$, IgM) and concentration as the aforementioned antibody. The sample is then incubated with the labeled antibody and detection reagents. These steps will help ensure that what appears to be specific staining was not caused by non-specific interactions of immunoglobulin molecules with the sample. Examples and a further description of this method can be found in "Tissue Microarrays—Methods in Molecular Biology Volume 664, 2010, pp 113-126, Immunohistochemical Analysis of Tissue Microarrays; Ronald Simon, Martina Mirlacher, and Guido Sauter".

In the context of the present invention the G protein-coupled receptor Smoothened is interchangeably abbreviated as "Smoothened" and "Smo".

In the context of the present invention the expression "the activation of the hedgehog signaling pathway" in particular refers to the activation of expression of primary target genes of the Hedgehog signaling pathway, including GLI, HHIP, Ptch, more particularly of GLI expression via the hedgehog pathway. Typically, GLI expression is triggered via binding of hedgehog to the Smo/Ptch (Smoothened/Patched) complex and thereupon GLI expression via signalling by Smo.

In the context of the present invention, the "activation of the hedgehog signaling pathway is independent of signaling by the G protein-coupled receptor Smoothened" as used in the present invention refers to the ability of certain cancers to activate the expression of primary target proteins of the Hedgehog signaling pathway, more particularly of GLI expression independent of signaling via Smo. Instead, in these cases GLI expression is activated by alternate routes, which are independent of the hedgehog signaling pathway as described above.

Known Smoothened inhibitors are for example LDE225 (by Novartis), LEQ506 (by Novartis), Vismodegib (GDC-0449), IPI-926 (by Infinity Pharmaceuticals), BMS-833923 (XL139) (by Bristol Myers Squibb; Exelixis), or PF-04449913 (by Pfizer), N-[3-(1H-Benzimidazol-2-yl)-4-chlorophenyl]-3,4,5-triethoxybenzamide (SANT-2), SANT19, SANT74, aSANT75, (3β,23β)-17,23-Epoxy-3-hydroxyveratraman-11-one (11-ketocyclopamine/Jervine), Cur61414 (by Curis), IPI-269609 (by Infinity), MRT 10, and for example cyclopamine (for further information and further Smoothened inhibitors, see e.g. Peukert S., Miller-Moslin K., ChemMedChem Volume 5, Issue 4, pages 500-512, Apr. 6, 2010).

In the present invention, patients e.g. can be stratified into patients wherein said cancer, or cells of said cancer, do not respond to Smoothened inhibitor therapy, and patients wherein in said cancer, or in the cells of said cancer, respond to Smoothened inhibitor therapy, based on their medical history, i.e. if at a previous point said cancer did not respond or ceased to respond to (wherein said response encompasses the amelioration or stabilization of one or more of the following: Disease state, symptom severity, tumor volume, tumor aggressiveness, propensity to form metastases, tumor malignancy, tumor invasiveness and patient's overall physical state), to Smoothened inhibitor therapy. Alternatively, said stratification can be done by a procedure comprising the steps of 1) providing a sample from said patient, wherein said sample comprises cancer cells from said patient,
2) preparing two or more cell cultures from said sample,
3) incubating said cell cultures to increase the number of cells in order to obtain in each cell culture a cell number which is sufficient to provide at least 1 µg total RNA, in other embodiments at least 200 ng or at least 500 ng total RNA,
4) adding a Smo-inhibitor to all but one of said cell cultures,
5) adding a Smoothened agonist to said cell cultures,
6) incubating said cell cultures,
7) determining the level of GLI expression in said cell cultures,
8) comparing the level of GLI expression in said cell cultures to which a Smoothened inhibitor has been added to said sample which no Smoothened inhibitor has been added,
9) if the expression of GLI in at least one of said cell cultures to which a Smoothened inhibitor has been added is lower than the expression of GLI in said sample which no Smoothened inhibitor has been added, classifying said patient as patient wherein said cancer, or the cells of said cancer, respond to Smoothened inhibitor therapy, and otherwise classifying said patient as patient wherein said cancer, or cells of said cancer, do not respond to Smoothened inhibitor therapy.

In the above method,
in step 2, cell cultures usually comprise at least a growth medium typically used in the field of cell biology;

in step 3 in particular embodiments, said cell number is at least 500,000, more particularly at least 1,000,000, even more particularly at least 1,500,000 cells, in other particular embodiments, said cell number is at least 100,000, more particularly at least 500.000, even more particularly at least 1,000,000 cells;

in step 4 a Smoothened inhibitor is in particular embodiments added in an amount known to usually at least partially inhibit cellular Smo activity; in the particular embodiments where a Smoothened inhibitor is added to more than one cell culture, a concentration gradient can be prepared by adding different amounts of Smoothened inhibitor to each cell culture;

in step 4 the Smoothened inhibitor is in particular embodiments a small molecule, more particularly a Smoothened inhibitor as described herein, in step 5 in particular embodiments the Smoothened agonist is added to each cell culture in the same amount with respect to the cell number (i.e. more agonist for a higher cell number) in said cell culture, and in an amount known to usually at least partially activate GLI expression; said amount can for instance be determined in one or more comparative cell cultures comprising cancer cells of the same or similar tissue from a subject which is known to be a as patient wherein said cancer, or the cells of said cancer, respond to Smoothened inhibitor therapy;

in step 6 in particular embodiments said cell cultures are incubated for at least 24 h, 36 h, or 48 h, in this way the cells can express GLI upon the addition of the Smoothened agonist (and in the case that said cancer cells respond to Smoothened inhibitor therapy, allows said cancer cells to degrade GLI);

in steps 7 the level of GLI expression can e.g. be determined with the qPCR and/or Western blot methods described herein;

in step 9, in particular embodiments, to classify said patient as patient wherein said cancer, or the cells of said cancer, respond to Smoothened inhibitor therapy, the difference in the level of GLI expression between said at least one of said cell cultures to which a Smoothened inhibitor has been added and said sample which no Smoothened inhibitor has been added is statistically significantly, e.g. at least 20%, particularly at least 40%, more particularly at least 60%, even more particularly at least 75%, yet even more particularly at least 90%.

Patients can be stratified into patients having cancer wherein in said cancer or in cells of said cancer the activation of the hedgehog signaling pathway is independent of signaling by the G protein-coupled receptor Smoothened and patients having cancer wherein in said cancer or in cells of said cancer the activation of the hedgehog signaling pathway is dependent of signaling by the G protein-coupled receptor Smoothened with common methods. For example, the specific genetic subtype of cancer can be determined and compared with a database. If in said specific genetic subtype of cancer activation of the hedgehog signaling pathway is known to be independent of signaling by the G protein-coupled receptor Smoothened, e.g. in the scientific literature, and in a particular example in the scientific literature cited herein, said patient is classified as Smo independent cancer patient. If in said specific genetic subtype of cancer activation of the hedgehog signaling pathway is known to be dependent of signaling by the G protein-coupled receptor Smoothened, e.g. in the scientific literature, and in a particular example in the scientific literature cited herein, said patient is classified as Smo dependent cancer patient.

Patients can further be stratified into patients having cancer wherein in said cancer or in cells of said cancer the activation of the hedgehog signaling pathway is independent of signaling by the G protein-coupled receptor Smoothened and patients having cancer wherein in said cancer or in cells of said cancer the activation of the hedgehog signaling pathway is dependent of signaling by the G protein-coupled receptor Smoothened by a method comprising the steps of
1) providing a sample from said patient, wherein said sample comprises cancer cells from said patient,
2) preparing a cell culture from said sample,
3) incubating said cell culture to increase the number of cells in order to obtain a cell number which is sufficient to provide at least 1 μg total RNA, in other embodiments at least 200 ng or at least 500 ng total RNA,
4) adding a Smo-inhibitor to said cell culture,
5) incubating said cell cultures,
6) determining the level of GLI expression in said cell cultures,
7) if GLI expression is detectable in said cell culture, classifying said patient as patient having cancer wherein in said cancer or in cells of said cancer the activation of the hedgehog signaling pathway is independent of signaling by the G protein-coupled receptor Smoothened, and if GLI expression is not detectable in said cell culture, classifying said patient as patient having cancer wherein in said cancer or in cells of said cancer the activation of the hedgehog signaling pathway is dependent of signaling by the G protein-coupled receptor Smoothened.

In the above method, in step 2, cell cultures usually comprise at least a growth medium typically used in the field of cell biology;

in step 3 in particular embodiments, said cell number is at least 500.000, more particularly at least 1,000,000, even more particularly at least 1,500,000 cells, in other particular embodiments, said cell number is at least 100,000, more particularly at least 500.000, even more particularly at least 1,000,000 cells;

in step 4 a Smoothened inhibitor is in particular embodiments added in an amount known to usually at least partially inhibit cellular Smo activity; in the particular embodiments where a Smoothened inhibitor is added to more than one cell culture, a concentration gradient can be prepared by adding different amounts of Smoothened inhibitor to each cell culture; in this case, the Smoothened inhibitor can also be and RNA molecule inhibiting the expression of Smo, e.g. siRNA or shRNA, particularly an RNA molecule which specifically and/or selectively binds to the gene encoding for Smo and prevents transcription of said gene (this is typically also known as a Smo knockdown);

in step 4 the Smoothened inhibitor is in particular embodiments a small molecule, more particularly a Smoothened inhibitor as described herein, in step 5 in particular embodiments in particular embodiments said cell cultures are incubated for at least 12 h, 24 h, or 36 h, in this way the cells can express GLI;

in step 6 the level of GLI expression can e.g. be determined with the qPCR and/or Western blot methods described herein;

in step 7, in particular embodiments, not detectable means that by the state of the art measurement methods used for detecting said label, no signal relating to GLI expression is detectable, and/or said signal is not significant in relation to the background noise generated by said measurement method.

In the context of the present invention "the G protein-coupled receptor Smoothened is not responsive to inhibition by Smoothened inhibitors" means that Smoothened activity is not inhibited by Smoothened inhibitors. Usually, in these cases cancer cells show at least one mutation in a gene encoding for Smoothened, particularly The D473H mutation which results in an amino acid substitution at position 473 in Smoothened, from an aspartic acid (D) to a histidine (H). Said mutation typically leads to an alteration of the Smoothened receptor which prevents binding of Smoothened inhibitors, in particular of known Smoothened inhibitors which target wild type Smoothened. Said mutation may originate from the patient's innate chromosomal setup, i.e. a hereditary trait, or may be acquired at a later point, e.g. by a spontaneous mutation of cancer cell DNA, which is then selected and passed on to further cancer cell generations as a response to therapy with Smoothened inhibitors. Patients can accordingly be classified as patients having cancer wherein in said cancer or in cells of said cancer the activation of the hedgehog signaling pathway is independent of signaling by the G protein-coupled receptor Smoothened by analyzing the genes encoding for Smo in cells from said patient's cancer for the presence of a mutation as described above, which can e.g. be done by the qPCR methods as described herein.

Patients having cancer wherein in said cancer or in cells of said cancer the activation of the hedgehog signaling pathway is dependent of signaling by the G protein-coupled receptor Smoothened can further be stratified into patients having cancer wherein the G protein-coupled receptor Smoothened is not responsive to inhibition by Smo inhibitors and patients having cancer wherein the G protein-coupled receptor Smoothened is not responsive to inhibition by Smo inhibitors by the method described above for stratifying into patients wherein said cancer, or cells of said cancer, do not respond to Smoothened inhibitor therapy, and patients wherein in said cancer, or in the cells of said cancer, respond to Smoothened inhibitor therapy.

In the context of the present invention, said sample from said patient comprising cancer cells from said patient is for instance a biopsy of said patient's cancer.

As used herein, the term "DYRK1B" means an enzyme from the family of serine/threonine kinases, more particularly a member of the Minibrain/DYRK family of kinases which is specified by the UniProt/Swiss-Prot ID Q9Y463; or as Refseq proteins: NP_004705.1, NP_006474.1 and NP_006475.1, and/or an expression product of a gene encoding for DYRK1B as defined herein below. As used herein, the term "DYRK1B" in certain embodiments also includes variants of DYRK1B, such as isoforms, homologs and mutants of DYRK1B, which share at least 95% sequence homology, more particularly at least 97% sequence homology, even more particularly at least 99% sequence homology with DYRK1B as defined above, and in the case of proteins and/or gene expression products in certain embodiments have essentially the same enzymatic activity profile, i.e. process essentially the same substrates as DYRK1B as defined above, wherein however the enzymatic activity of said variants of DYRK1B may differ (i.e. be higher or lower than) from DYRK1B as defined above by up to two orders of magnitude, particularly up to one order of magnitude, more particularly up to a factor of 2. A particular variant of DYRK1B which is comprised by the present invention is Mirk, which typically is located in skeletal muscle tissue, whereas DYRK1B typically is located in brain tissue.

In the context of the present invention said at least one protein playing a role in the hedgehog signaling pathway can e.g. be selected from the group comprising Patched, GLI, Smoothened, HHIP, Hedgehog and SUFU.

In the context of the present invention, the term "GLI" refers to members of the GLI protein family, such as GLI1, GLI2, GLI3 in particular embodiments and, unless specified otherwise particularly to GLI1.

In general, and unless specified otherwise, the proteins, genes and/or gene expression products as defined herein in certain embodiments also include variants of said proteins, genes and gene expression products, such as isoforms, homologs and mutants thereof, which share at least 95% sequence homology, more particularly at least 97% sequence homology, even more particularly at least 99% sequence homology with, the proteins, genes and/or gene expression products as defined herein, and in the case of proteins and/or gene expression products in certain embodiments have essentially the same enzymatic activity as, the proteins and/or gene expression products as defined herein, wherein however the enzymatic activity of said variants may differ (i.e. be higher or lower than) from the proteins, and/or gene expression products as defined herein by up to two orders of magnitude, particularly up to one order of magnitude, more particularly up to a factor of 2.

As used herein, the term "DYRK1B inhibitor" or "compound which inhibits the activity of DYRK1B" means a compound which is capable of inhibiting the enzymatic activity of DYRK1B in vitro and/or in vivo, e.g. in a patient in need thereof, particularly with an inhibitory concentration $IC_{50}$ of 50 mM or lower, more particularly with an inhibitory concentration $IC_{50}$ of 20 mM or lower, even more particularly with an inhibitory concentration $IC_{50}$ of 5 mM or lower, yet even more particularly with an inhibitory concentration $IC_{50}$ of 1 mM or lower, e.g. in the kinase assay described herein. The chemical nature of the DYRK1B inhibitor is not particularly limited and can for example be selected from the group comprising synthetic compounds, naturally occurring compounds, peptides, proteins, antibodies, and small molecules. For the avoidance of doubt, it is mentioned that the above $IC_{50}$ values are erroneous, which a skilled person readily recognizes, because an inhibitory concentration $IC_{50}$ of 50 mM, 20 mM, 5 mM, 1 mM or lower is apparently not very potent for treatment of diseases. Thus the above values should, at least in a specific embodiment be read as $IC_{50}$ of 50 µM or lower, more particularly with an inhibitory concentration $IC_{50}$ of 20 µM or lower, even more particularly with an inhibitory concentration $IC_{50}$ of 5 µM or lower, yet even more particularly with an inhibitory concentration $IC_{50}$ of 1 µM or lower.

In certain embodiments of the present invention, said DYRK1B inhibitor is selective and/or specific for DYRK1B. In certain embodiments of the present invention, said DYRK1B inhibitor is non-selective and/or non-specific for DYRK1B. It is apparent that non-selectivity and/or non-specificity is acceptable, as long as no intolerable side-effect occurs due to the non-selectivity and/or non-specificity of the DYRK1B inhibitor. In this context, "intolerable side-effect" means an effect of the addition or administration of the DYRK1B inhibitor which is different from the inhibition of DYRK1B, e.g. the inhibition of one or more further enzymes, and which conflicts with the objective to be achieved by the addition or administration of the DYRK1B inhibitor to such a degree that no acceptable results may be achieved. Examples are for instance a pharmaceutical side effect which would prevent the use of the DYRK1B inhibitor for therapeutic purposes, such as high toxicity, cancerogenity or the like. As one example of tolerable non-selectivity and/or non-specificity, the DYRK1B inhibitor may inhibit DYRK1A in addition to DYRK1B. DYRK1A function is largely dispensable in GLI-driven cancer cells. Off-target effects of DYRK1B inhibitors will not be critical as inhibition of DYRK1A—if at all—will enhance the GLI-antagonizing effect of DYRK1B inhibition in cancer cells. This effect is for instance credible in view of the results shown in Mao et al., J. Biol. Chem. 2002, 277, 38, 35156-35161, in particular FIGS. 4 and 6.

It is also within the general scope of the present invention to inhibit DYRK1B activity by inhibiting the expression of a gene encoding for DYRK1B. This can be achieved by inhibiting expression of said gene on DNA level and/or RNA level, thus lowering the amount of DYRK1B produced by said gene and consequently lowering the overall activity of DYRK1B in a subject in which the expression of said gene is inhibited. The methods by which the expression of said gene is inhibited are not particularly limited, and may comprise the addition or administration of an agent selected from the group comprising siRNA, shRNA, miRNA, antisense-oligonucleotides.

As used herein, the expression that in a cancer or cells in a cancer the "hedgehog signaling pathway is independent of signaling by the G protein-coupled receptor Smoothened" means that the proliferation of a certain cancer entity is independent of the G protein-coupled receptor Smoothened and thus not affected, or at least not substantially affected, by inhibition of the G protein-coupled receptor Smoothened. Accordingly, patients suffering from such cancer cannot be treated and do not benefit by therapeutic approaches which are directed to inhibition of the G protein-coupled receptor Smoothened.

As used herein, the term "hedgehog signaling pathway" means a cellular signaling pathway comprising an interaction with a protein of the family known as hedgehog proteins, such as e.g. the proteins commonly known as "sonic hedgehog" (UniProtKB/Swiss-Prot: Q15465), "indian hedgehog" (UniProtKB/Swiss-Prot: Q14623) and "desert hedgehog" (UniProtKB/Swiss-Prot: O43323) (Ingham and McMahon, 2001).

As used herein, the term "treating" or "treatment" encompasses the amelioration or stabilization of one or more of the following: Disease state, symptom severity, tumor volume, tumor aggressiveness, propensity to form metastases, tumor malignancy, tumor invasiveness and patient's overall physical state.

As used herein, the term "therapeutically effective amount" means an amount, e.g. of a compound, which upon administration to a patient in need thereof results in a therapeutic effect on the disease to be treated. Such therapeutic effects, e.g. in cancer therapy, may comprise an effect on diseased tissue or cells including changes in tumor size, metabolic activity, cell viability, blood supply of the tumor, i.e. angiogenesis, composition of the tumor, e.g. relationship of cells comprising the tumor e.g. tumor cells, immune cells, fibroblasts and endothelial cells; and an effect on the patient's medical state including improvements in clinical status, health status, progression or stabilization of disease, increased time of progression free survival, cure of disease, enhanced overall survival, delay of disease progression and alleviation of symptoms. Such effects usually do not occur immediately after administration of a compound and may be delayed, e.g. by hours, days, weeks or months, depending e.g. on the specific patient, type of disease and overall situation under which the therapy is administered.

As used herein, the term "sample" in principle comprises samples from natural sources, such as a sample obtainable from a mammal, and artificial samples, which are obtainable by admixing several ingredients, wherein said ingredients may or may not be derived from natural sources, and may e.g. comprise ingredients selected from the group comprising synthetic and/or natural proteins, peptides, oligo- or polynucleic acids, etc. In certain embodiments, samples are from natural sources, which include bodily fluids and/or tissue samples, such as bodily fluid and/or a tissue sample obtainable from mammals. Said samples from natural sources can be used in the present invention with or without further processing after being obtained from their source, e.g. a mammal. Such processing can for instance comprise separation, fractionation, dilution, dispersion, mechanical treatment such as sonification, or grinding, concentration, removal of certain components of said sample, or addition of compounds, such as salts, buffers, detergents, etc.

As used herein, the term "bodily fluid" or "body fluid" specifies a fluid or part of a fluid originating from the body of a patient, including fluids that are excreted or secreted from the body of the patient, including but not limited to blood, including peripheral blood, serum, plasma, urine, interstitial fluid, liquor, aqueous humour and vitreous humour, bile, breast milk, cerebrospinal fluid, endolymph, perilymph, ejaculate, gastric juice, mucus, peritoneal fluid, pleural fluid, saliva, sweat, tears and vaginal secretion, particularly peripheral blood, serum, plasma and urine. Said bodily fluid itself may or may not comprise diseased and/or non-diseased cells.

As used herein, the term "tissue sample" specifies a non-fluid material or solid originating from the body of a patient. Tissue samples include, but are not limited to samples of bone material, bone marrow, skin, hair follicle, mucosa, brain, cartilage, muscles, lung, kidney, stomach, intestines, bladder and liver. Said tissue sample itself may or may not comprise diseased cells, and may for instance be a sample taken from a diseased region of a patient's body, such as a biopsy of a tumor. In certain embodiments the tissue sample is selected from skin, hair follicle or oral mucosa.

In the embodiments of the present invention, the sample is obtained from the patient by any method and/or means commonly known to the skilled person in the field of medicine, e.g. in certain embodiments blood sample taking by venipuncture.

As used herein, the term "peripheral blood" specifies blood obtained from the circulation remote from the heart, i.e. the blood in the systemic circulation, as for example blood from acral areas.

As used herein, the term "whole blood" specifies unmodified blood comprising cells and fluid, as obtained from the donor of said blood, such as a patient.

As used herein, the term "patient" specifies a subject which is suspected of having a disease or disorder, in certain embodiments having a medical condition, which may require treatment. In certain embodiments of the present invention, the patient is a cancer patient, i.e. a subject suffering from cancer. The patient may have received prior treatment for the disease in question, e.g. in the case of a cancer patient by radiation or chemotherapy, or the patient's disease may be untreated prior to the application of the embodiments of the present invention to said patient.

As used herein, the term "small molecule" is to be understood as commonly used in the field of pharmacology and means a low molecular weight organic compound which is not a polymer, and which usually has a molecular weight of about 800 Daltons or lower, particularly, 700 Daltons or lower, more particularly 600 Daltons or lower, even more particularly 500 Daltons or lower. From a functional point of view, a small molecule has to molecular weight which allows the molecule to rapidly diffuse across cell membranes and/or reach the interior of a mammalian cell.

As used herein, the term "gene encoding for DYRK1B" means a gene identified by the NCBI reference sequence (Refseq mRNAs NM_004714.1, NM_006483.1, NM_006484.1, or the Ensemble transcripts ENST00000323039(uc002omj.2) ENST00000348817 (uc002omi.2) ENST00000430012(uc002omk.2 uc002oml.2))

As used herein, the term "inhibited on the DNA level and/or on the RNA level" means that the intracellular level of the protein of interest, in the case of the present invention DYRK1B, is diminished by inhibiting the expression of the gene encoding for the protein of interest. This can be achieved either by an inhibition on the DNA level, i.e. by inhibiting transcription of the gene encoding for the protein of interest, or by an inhibition on the RNA level, i.e. by inhibiting translation of an RNA transcribed from the gene encoding for the protein of interest. The methods by which inhibition on the DNA level and/or on the RNA level can be achieved are well known to the skilled person and any such well known method which is suitable for the purposes of the present invention, e.g. for therapeutic use in a patient suffering from cancer, or for in vitro use such as in an assay, can be applied in the embodiments of the present invention.

In the context of the present invention, a mammal is in certain embodiments a human.

As used herein, the terms "inhibit DYRK1B", "inhibition of DYRK1B" and "DYRK1B inhibition" are used interchangeably and mean that the enzymatic activity of DYRK1B is diminished, which results in a diminished turnover rate with respect to the conversion of DYRK1B substrates by DYRK1B, which can particularly be determined by measuring a reduction in the level of GLI expression by the methods described herein, e.g. the qPCR or Western Blot methods described herein. Said reduction in the level of GLI expression is in particular embodiments at least 50%, more particularly at least 70%, even more particularly at least 80%, yet even more particularly at least 90%.

As used herein, the term "formation of resistance of cancer cells against chemotherapeutic agents" means that over the course of a treatment with a chemotherapeutic agent, the treated cancer cells develop a resistance against said chemotherapeutic agent, i.e. become non-responsive to said chemotherapeutic agent. The result of resistance against said chemotherapeutic agent is that the cancer cells will proliferate, irrespective of continued therapy with said chemotherapeutic agent. Usually, such resistance against a chemotherapeutic agent is not reversible, and usually, in such cases of resistance against a chemotherapeutic agent, therapy has to be changed to a different treatment regimen, e.g. encompassing the administration of a different chemotherapeutic agent, radiotherapy, or the like.

In the embodiments of the present invention, in particular wherein a DYRK1B inhibitor is administered in an amount which is effective to inhibit DYRK1B said DYRK1B inhibitor is administered in an amount which is effective to inhibit DYRK1B by for example by at least 50%, more particularly at least 75%, even more particularly at least 90%, inhibition of DYRK1B can be determined in vitro by a DYRK1B kinase assay and ex vivo by measuring the expression level of a primary target gene of the hedgehog signaling pathway, e.g. GLI, particularly in a sample obtained from a patient; this can be done by the methods described herein.

In further particular embodiments of the present invention, the hedgehog signaling pathway is inhibited, which can be determined by measuring the expression level of a primary target gene of the hedgehog signaling pathway, e.g. GLI, particularly in a sample obtained from a patient; this can be done by the methods described herein, e.g. qPCR or Western Blot.

In further particular embodiments of the present invention, the cellular expression of GLI, particularly GLI1 is inhibited.

In further particular embodiments of the present invention, the hedgehog signaling pathway-mediated cellular expression of GLI, particularly GLI1 is inhibited.

Furthermore, particular genetic subtypes of cancer of certain embodiments of the present invention are listed in the following; reference documents with further information are indicated in parentheses; for said genetic subtypes of cancer, among others, it is known that activation of the hedgehog signaling pathway is independent of signaling by the G protein-coupled receptor Smoothened:

esophagus/GI (Wang, Y., et al. (2012). Canc. cell 21(3) 374-387. doi:10.1016/j.ccr.2011.12.028);

gastrointestinal (Berman, D. M., et al. (2003). Nature, 425(6960), 846-851. doi:10.1038/nature01972);

gastrointestinal stromal tumors (Pelczar, P. et al. (2013). Gastroenterology, 144(1), 134-144.e6. doi:10.1053/j.gastro.2012.09.061);

pancreas (Nolan-Stevaux, O. et al. (2009). Genes & Development, 23(1), 24-36. doi:10.1101/gad.1753809; Feldmann, G., et al. (2007). Cancer Research, 67(5), 2187-2196. doi:10.1158/0008-5472.CAN-06-3281; Karhu, R. et al. (2006) Genes, chromosomes & cancer 45, 721-730; Merchant, A. A., and Matsui, W. (2010) Clin. Canc. Res. 16, 3130-3140);

prostate (Karhadkar, S S et al. (2004). Nature, 431(7009), 707-712. doi:10.1038/nature02962; Sanchez, P., et al. (2004). PNAS, 101(34), 12561-12566. doi:10.1073/pnas.0404956101);

biliary tract (Berman, D M et al. (2003). Nature, 425 (6960), 846-851. doi:10.1038/nature01972);

bladder/urogenital (Fei, D L et al. Cancer Res. 2012 Sep. 1; 72(17):4449-58);

basal cell carcinoma/skin (Hahn, H., et al. (1996). Cell, 85(6), 841-851);

medulloblastoma/brain (Goodrich, L. V., et al. (1997). Science, 277(5329), 1109-1113);

rhabdomyosarcoma (Ecke, I. et al. (2008). Molecular carcinogenesis, 47(5), 361-372. doi:10.1002/mc.20394; Deng, X. et al. (2006) Cancer research 66, 4149-4158; Friedman, E. (2011) Sarcoma 2011, 260757, doi:10.1155/2011/260757; Jin, K. et al. (2007) Cancer research 67, 7247-7255; Mercer, S. E. et al. (2006) Cancer research 66, 5143-5150; Yang et al., Carcinogenesis. 2010 April; 31(4): 552-558);

glioma/brain (Clement, V., et al. (2007). Current biology: CB, 17(2), 165-172. doi:10.1016/j.cub.2006.11.033);

small-cell lung cancer/lung (Watkins, D. N. et al. (2003). Nature, 422(6929), 313-317. doi:10.1038/nature01493; Park K S, et al. Nat Med. 2011 Oct. 9; 17(11):1504-8. doi: 10.1038/nm.2473.);

oral squamous cell carcinoma (Yan M, et al. Oral Oncol. 2011 June; 47(6):504-9. doi: 10.1016/j.oraloncology.2011.03.027. Epub 2011 May 4);

melanoma/skin (Stecca B et al. (2007) PNAS 104(14) 5895-5900 doi:10.1073/pnas.0700776104);

colorectal cancer/GI (Varnat, F., et al. (2009). EMBO molecular medicine, 1(6-7), 338-351. doi:10.1002/emmm.200900039; Deng, X. et al. (2006) Cancer research 66, 4149-4158; Friedman, E. (2011) Sarcoma 2011, 260757, doi:10.1155/2011/260757; Jin, K. et al. (2007) Cancer research 67, 7247-7255; Mercer, S. E. et al. (2006) Cancer research 66, 5143-5150; Yang et al., Carcinogenesis. 2010 April; 31(4):552-558);

non-small cell lung cancer/lung (Yuan, Z., et al. (2007). Oncogene, 26(7), 1046-1055. doi:10.1038/sj.onc.1209860);

osteosarcoma/bone (Bovée, J. V. M. G., et al. (2010). Nature Reviews Cancer, 10(7), 481-488. doi:10.1038/nrc2869; Ho, L., et al. (2009). Cancer cell, 16(2), 126-136. doi:10.1016/j.ccr.2009.05.013; Friedman, E. (2011) Sarcoma 2011, 260757, doi:10.1155/2011/260757; Jin, K. et al. (2007) Cancer research 67, 7247-7255; Mercer, S. E. et al. (2006) Cancer research 66, 5143-5150; Yang et al., Carcinogenesis. 2010 April; 31(4):552-558);

glioblastoma/brain (Clement, V., et al. (2007). Current biology: CB, 17(2), 165-172. doi:10.1016/j.cub.2006.11.033);

chronic lymphacytic leukemia/blood (Desch, P., et al. (2010). Oncogene, 1-11. doi:10.1038/onc.2010.243);

chronic myeloid leukemia/blood (Dierks, C., et al. (2008). Cancer cell, 14(3), 238-249. doi:10.1016/j.ccr.2008.08.003);

multiple myeloma/blood (Peacock C D, et al. PNAS 2007 Mar. 6; 104(10):4048-53);

ovarian cancer/urogenital (McCann C K, et al. PLoS One. 2011; 6(11):e28077. doi: 10.1371/journal.pone.0028077.

Epub 2011 Nov. 29; Friedman, E. (2007) Journal of cellular biochemistry 102, 274-279, 2007; Karhu et al., Genes Chromosomes Cancer. 2006 August; 45(8):721-730);

meningioma/brain (Clark, V. E. et al., Science, 2013 Jan. 24, Epub ahead of print, PMID (PubMed-ID) 23348505—as supplied by publisher; Aavikko M. et al., Am J Hum Genet, 2012 Sep. 7, 91(3), 520-526);

liver/GI (Arzumanyan A. et al. Cancer Res. 2012 Nov. 15; 72(22):5912-20);

liver (Huang, S., et al. (2006). Carcinogenesis, 27(7), 1334-1340. doi:10.1093/carcin/bgi378).

It is apparent that the embodiments of the present invention as described herein can be combined to form further particular embodiments of the present invention.

EXAMPLES

Material and Methods

Figure 1:
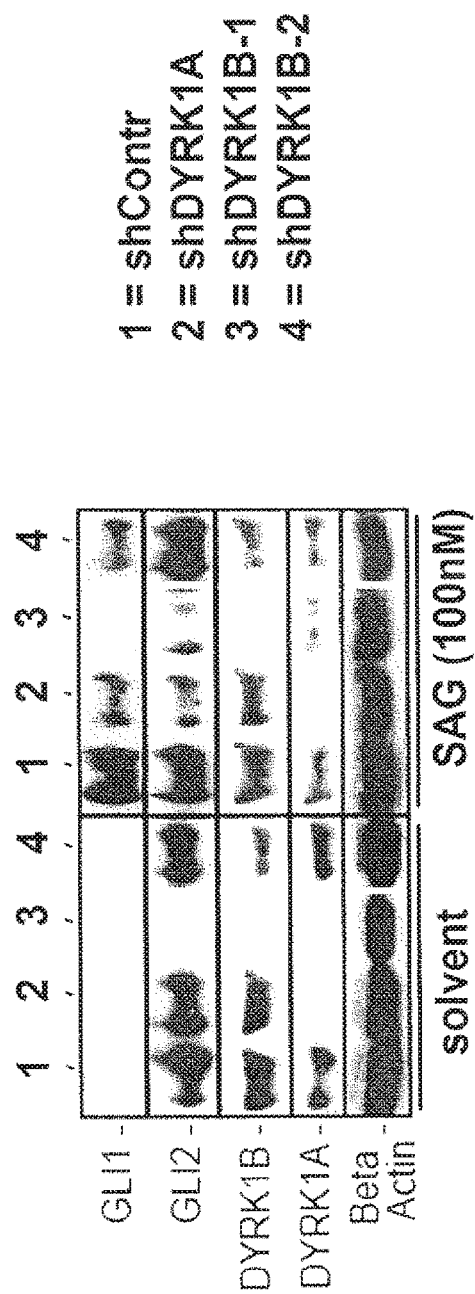
FIG. 1: Western blot analysis (upper panel) and qPCR analysis (lower panel) of medulloblastoma cells (DAOY) treated with solvent (DMSO) or SAG (100 nM, 48 hours under starving conditions) transduced with shRNA targeting DYRK1A (shDYRK1A) or DYRK1B (shDYRK1B). DYRK1B targeting efficiently reduces GLI1 and GLI2 protein expression as well as GLI1 and PTCH1 mRNA expression. Non-target shRNA (shContr) served as control. Beta Actin served as loading control for western blot analysis. qPCR data represent fold mRNA changes compared to solvent (DMSO) treated control.
Figure 1:
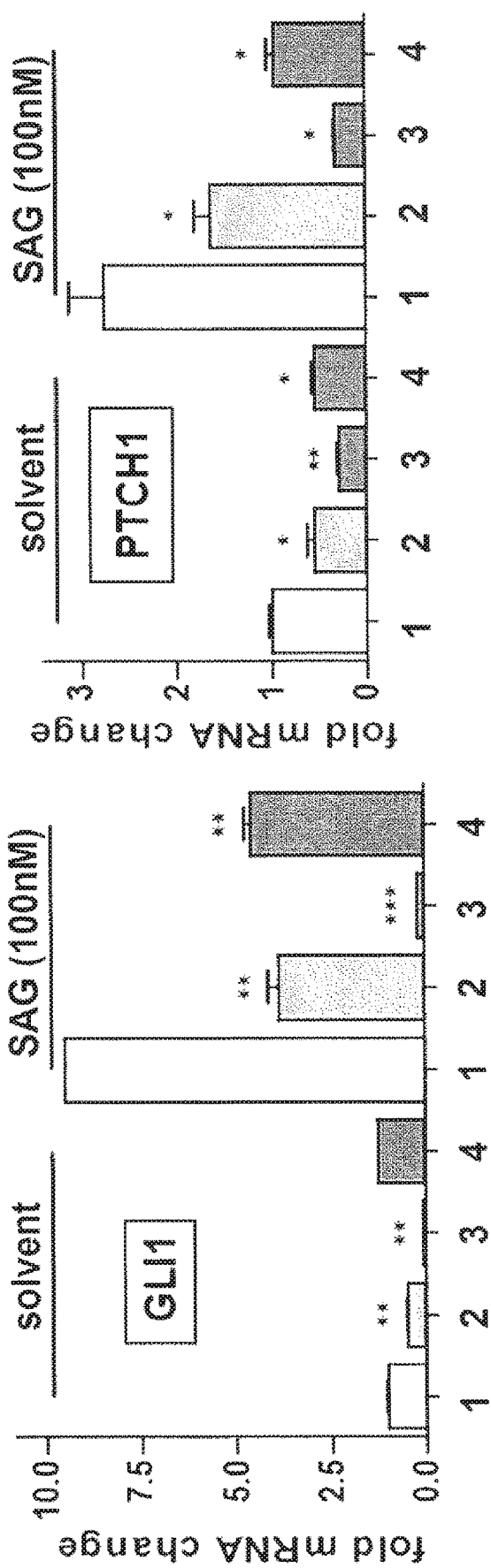

In all cases, kits and specific reagents were used according to the instructions in the respective manuals provided by the manufacturer, unless stated otherwise. The methods described in said manuals are incorporated herein by reference.

Cell Culture and Inhibitor Treatments

DAOY cells (ATCC) were grown in MEM media (PAA Laboratories, Germany) supplemented with 10% fetal bovine serum (FBS) (PAA Laboratories, Germany), penicillin (62.5 µg/ml) and streptomycin (100 mg/ml) at 37° C. in an atmosphere containing 5% $CO_2$. BSZ2 cells (So et al., 2006) were grown in 154-CF media (Life Technologies, UK) supplemented with 2% heat inactivated (56° C. for 30 minutes) and chelexed fetal bovine serum (FBS) (PAA Laboratories, Germany) (FBS was chelexed by adding to 50 mL FBS 10 g Chelex 100 (Bio-Rad Laboratories GmbH, Germany) followed by stirring for 60 min at RT; chelexed FBS was sterile filtered prior to use), penicillin (62.5 µg/ml) and streptomycin (100 mg/ml) at 37° C. in an atmosphere containing 5% $CO_2$. Panc-1 and A673 cells (ATCC) were grown in DMEM media (PAA Laboratories, Germany) supplemented with 10% fetal bovine serum (FBS) (PAA Laboratories, Germany), penicillin (62.5 µg/ml) and streptomycin (100 mg/ml) at 37° C. in an atmosphere containing 5% $CO_2$. For 3-dimensional (3D) cultures, $5 \times 10^3$ cells were seeded in 12-well plates in 0.4% select agar on top of 0.5% bottom select agar (Life Technologies, Germany) according to standard protocols of anchorage independent growth assays (Eberl et al., 2012). 3D cultures were grown for 4-6 weeks at 37° C. in a humidified atmosphere containing 5% $CO_2$. Colony formation was documented on a stereomicroscope with Cell^D Image capture system (Olympus) and quantified using Colony Counter Software (Microtec Nition, Japan). SAG (smoothened agonist, N-Methyl-N'-(3-pyridinylbenzyl)-N'-(3-chlorobenzo[b]thiophene-2-carbonyl)-1,4-diaminocyclohexane) (Axxora LCC), Harmine (Fisher Scientific), GDC-0449 (LC Laboratories), GANT61 (Merck Chemicals Ltd.) and 4SC Compound P (4SC Discovery GmbH, Germany) were dissolved in DMSO.

The final DMSO concentration in all wild-type DAOY samples was 0.2%, in all other cell line experiments including DAOY shSUFU cells 0.1%.

The chemical structure and chemical name of 4SC compound P are shown below:

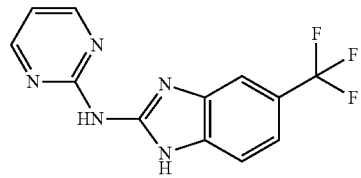

N-(pyrimidin-2-yl)-5-(trifluoromethyl)-1H-benzo[d]imidazol-2-amine

RNA Interference and Lentiviral Transduction

In the examples of the present invention, RNAi knockdown experiments were facilitated by lentiviral RNAi production and transductions, which were carried out as described in Kasper et al, 2007, which is incorporated herein by reference (Kasper et al., 2007). The following shRNA constructs (Sigma Aldrich mission TRC library) were used and the following abbreviations are used herein: shRNA DYRK1A (TRCN0000000526), shRNA DYRK1B-1 (TRCN0000002139), shRNA DYRK1B-2 (TRCN0000355722), shSUFU (TRCN0000019466) and control scrambled shRNA (SHC002). The functionality of the shRNAs was validated by Western blot analysis. Transduced cells were selected for puromycin resistance prior to further analysis.

RNA Isolation, qPCR and Western Blot Analysis

Total RNA was isolated using TRI-reagent (Molecular Research Center Inc.) followed by LiCl purification step. For this purpose, total RNA was dissolved in 100 mM Hepes pH 7.4/6M Urea and selectively precipitated by adding LiCl to a final concentration of 3M and incubating for 2 h at −20° C. Precipitated and purified RNA was used for cDNA synthesis using Superscript II reverse transcriptase (Life Technologies, Germany) according to the manufacturer's instructions. qPCR was done on a Rotorgene3000 (Qiagen, Germany) using iQ Sybr Green Supermix reagent (Bio-Rad Laboratories, UK). For qPCR analysis the following primer pairs (Microsynth AG, Switzerland) were used:

```
human GLI1:
                                    (SEQ ID NO: 1)
forward 5' TCTGGACATACCCCACCTCCCTCTG 3'

(SEQ ID NO: 2)
reverse 5' ACTGCAGCTCCCCCAATTTTTCTGG 3' human PTCH1:
                                    (SEQ ID NO: 3)
forward 5' TCCTCGTGTGCGCTGTCTTCCTTC 3'

(SEQ ID NO: 4)
reverse 5' CGTCAGAAAGGCCAAAGCAACGTGA 3'
```

For Western blot analysis, cells were lysed in Laemmli buffer supplemented with PhosStop (Roche, Germany) and cOmplete EDTA-free Protease Inhibitor Cocktail (Roche, Germany). Proteins were visualized with horseradish peroxidase-conjugated secondary antibodies in combination with enhanced chemiluminescence detection system (GE Health Care, USA).

The following antibodies were used:

Primary antibodies: Human and mouse GLI1: Cell Signaling Technology (Boston, Mass., USA), GLI1 (V812) #2534, polyclonal rabbit, 1:1000; Human GLI2: Santa Cruz Biotechnology, (Santa Cruz, Calif., USA), GLI2 (H300) sc-28674, polyclonal rabbit, 1:1000; Human and mouse DYRK1A: Cell Signaling Technology (Boston, Mass., USA), DYRK1A #2771, polyclonal rabbit, 1:1000; Human and mouse DYRK1B: Cell Signaling Technology (Boston, Mass., USA), DYRK1B #2703, polyclonal rabbit, 1:1000; Human SUFU: Santa Cruz Biotechnology, (Santa Cruz, Calif., USA), SUFU (C-15) sc-10933, polyclonal goat, 1:200; Human STAT3: BD Transduction Laboratories, (BD Biosciences, NJ, USA), STAT3 610189, monoclonal mouse, 1:5000; Human STAT5: Cell Signaling Technology (Boston, Mass., USA), STAT5 (3H7) #9358, monoclonal rabbit, 1:1000; Human Beta Catenin: Cell Signaling Technology (Boston, Mass., USA), β-Catenin #9587, polyclonal rabbit, 1:1000; Human and mouse Beta Actin: Santa Cruz Biotechnology (Santa Cruz, Calif., USA), β-Actin sc-47778, monoclonal mouse, 1:1000.

Secondary antibodies: Anti-mouse IgG, horse, HRP-linked: Cell Signaling Technology (Boston, Mass., USA) #7076, 1:3000; Anti-rabbit IgG, goat, HRP-linked: Cell Signaling Technology (Boston, Mass., USA) #7074, 1:3000; Anti-goat IgG, chicken, HRP-linked: Santa Cruz Biotechnology (Santa Cruz, Calif., USA) sc-2953, 1:5000.

Xenografts: For in vivo tumor growth studies $1\times10^6$ PANC1 or $1\times10^6$ L3.6p1 (Bruns et al., 1999) pancreatic cancer cells in 25% Matrigel (BD Biosciences, NJ, USA) were injected subcutaneously into the lower flanks of Foxn 1 nu/nu nude mice (Charles River Laboratories, USA). Tumor volume was measured with a caliper and calculated according to the formula [4/3×π×(length/2)×(width/2)×(height/2)].

Example 1—Genetic and Pharmacological Inhibition of DYRK1B in Human Cancer Cells Example 1A To address the effect of selected gene perturbations on canonical endogenous Hedgehog signaling in a human cancer cell line, the human medulloblastoma cell line (DAOY, ATCC ident. HTB-186) showing full responsiveness to Hedgehog activation by Smoothened agonist (SAG) as evidenced by activation of the direct Hedgehog target gene GLI1, a reliable and robust indicator of Hedgehog signaling pathway activity (FIG. 1) (Chen et al., 2002).

As shown in FIG. 1, RNAi knockdown of DYRK1A only moderately interfered with SAG induced (100 nM for 48 h under starving conditions) activation of GLI1 and PTCH1 expression. Notably, DYRK1B RNAi knockdown with shRNA DYRK1B-1 led to increased inhibition of SAG-induced pathway activation and HH target gene expression, respectively. This result was confirmed using shRNA for DYRK1B-2. Furthermore, knockdown of DYRK1B significantly decreased GLI2 protein levels independent of SAG treatment (FIG. 1 left panel). In the HH-responsive human medulloblastoma cell line DAOY, DYRK1 function is required for canonical HH signaling, with DYRK1B being the essential DYRK kinase.

Example 1B

Figure 2:
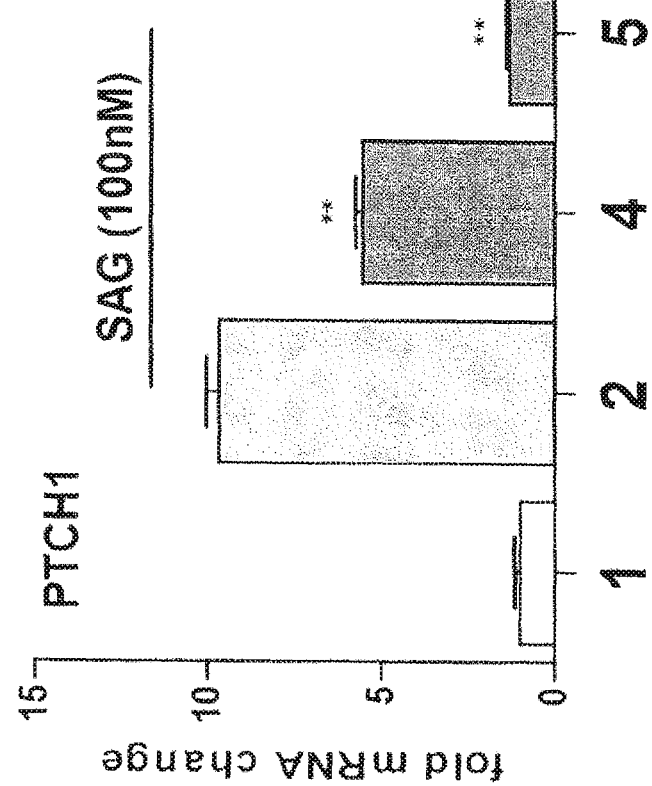
FIG. 2: Western blot analysis (upper panel) and qPCR analysis (lower panel) of DAOY cells stimulated for 48 hours with 100 nM SAG under starving conditions. Concomitant treatment with Harmine significantly inhibited GLI1 protein and PTCH1 mRNA expression. The SMO inhibitor GDC-0449 (Vismodegib) served as positive control, Beta Actin as loading control for western blot analysis. qPCR data represent fold mRNA change values compared to solvent (DMSO) treated controls. The final DMSO concentration in all wild-type DAOY samples was 0.2%, in all other cell line experiments including DAOY shSUFU cells 0.1%.
Figure 2:
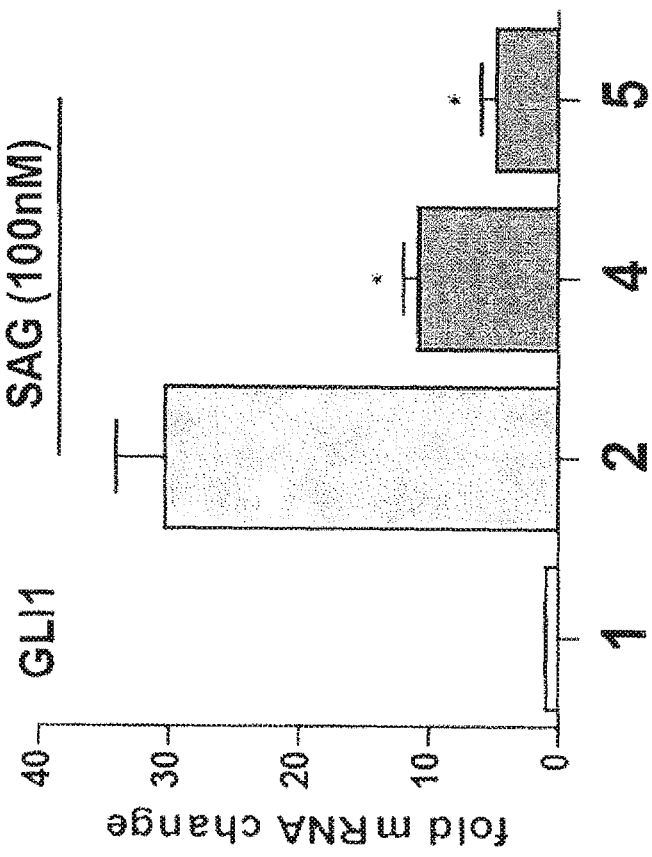
Figure 2:
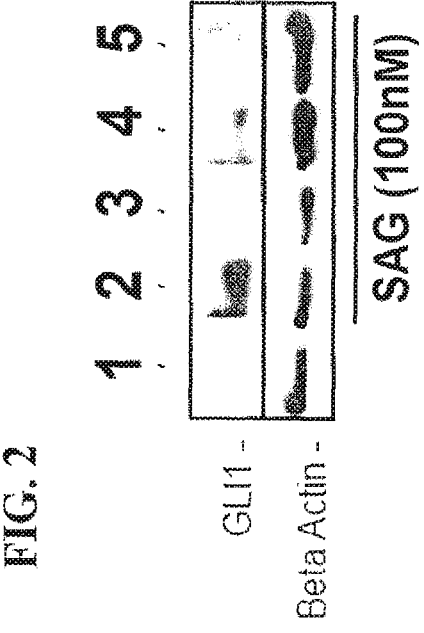
Figure 3:
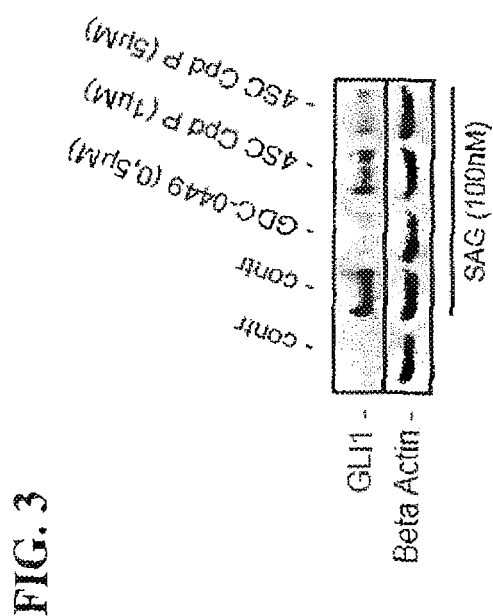
FIG. 3: Western blot analysis of DAOY cells treated with SAG as described in FIGS. 1 and 2. Concomitant treatment with DYKR1 inhibitor Compound P (Cpd P) significantly inhibited GLI1 protein expression.

SAG stimulated DAOY cells were treated with Harmine (7-MeO-1-Me-9H-pyrido[3,4-b]-indole) (dissolved at room temperature as 25 mM stock solution in DMSO and used at final concentration of 10 μM or 25 μM), a naturally occurring DYRK1 inhibitor, as well as with Compound P (Cpd P, dissolved at room temperature in DMSO as 20 mM stock solution and used at final concentration of 1 μM or 5 μM, respectively), a small molecule inhibitor of DYRK1, which is structurally unrelated to Harmine. Both Harmine and Cpd P prevented HH signaling as evidenced by a significant reduction of GLI target gene activation (FIGS. 2 and 3 respectively). For comparison, we also analyzed the effect of GDC-0449 (Vismodegib) treatment on SAG-mediated Hedgehog signaling pathway activation and target gene expression. As expected, the Smoothened antagonist GDC-0449 (dissolved at room temperature in DMSO as 10 mM stock solution and used at a final concentration of 0.504) efficiently blocked SAG-induced Hedgehog signaling pathway activation as evidenced by inhibition of GLI1 protein expression.

Example 1C

Figure 4:
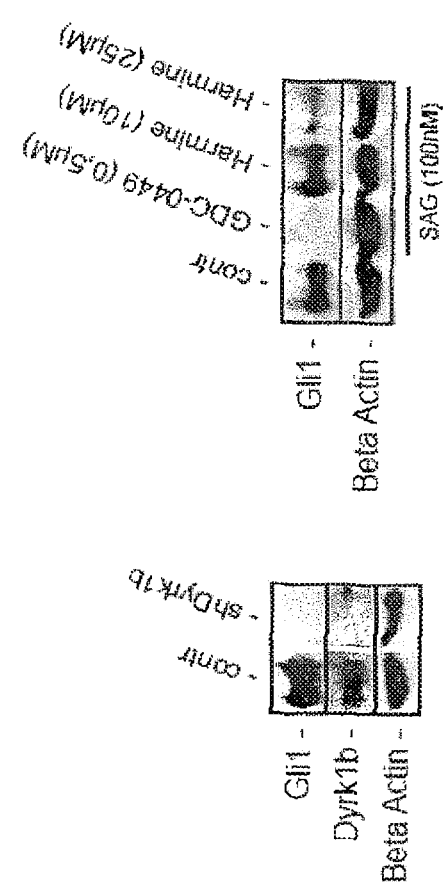
FIG. 4: Western blot analysis of RNAi knockdown (left panel) and pharmacological inhibition (right panel) of DYRK1b in mouse Ptch-/- BCC cells (BSZ2) showing reduced GLI1 expression upon RNAi mediated knockdown and pharmacological inhibition of DYRK1b by Harmine (the left panel demonstrates efficient DYRK1B knockdown and correlation of GLI repression). Beta Actin served as loading control for western blot analysis. *p<0.05, **p<0.01.

The above experiments were repeated with murine Ptch$^{-/-}$ basal cell carcinoma (BCC) cells (BSZ2) (So et al., 2006) showing constitutive, Smoothened-dependent canonical activation of Hh/GLI signaling. FIG. 4 shows that like in human HH-responsive DAOY cells, RNAi mediated genetic and pharmacological perturbation of DYRK1B function led to a decrease in GLI1 expression in BSZ2 cells. These findings confirm the critical role of DYRK1B in promoting canonical Hh/GLI signaling independent of the cellular model of Hh signaling.

Figure 5:
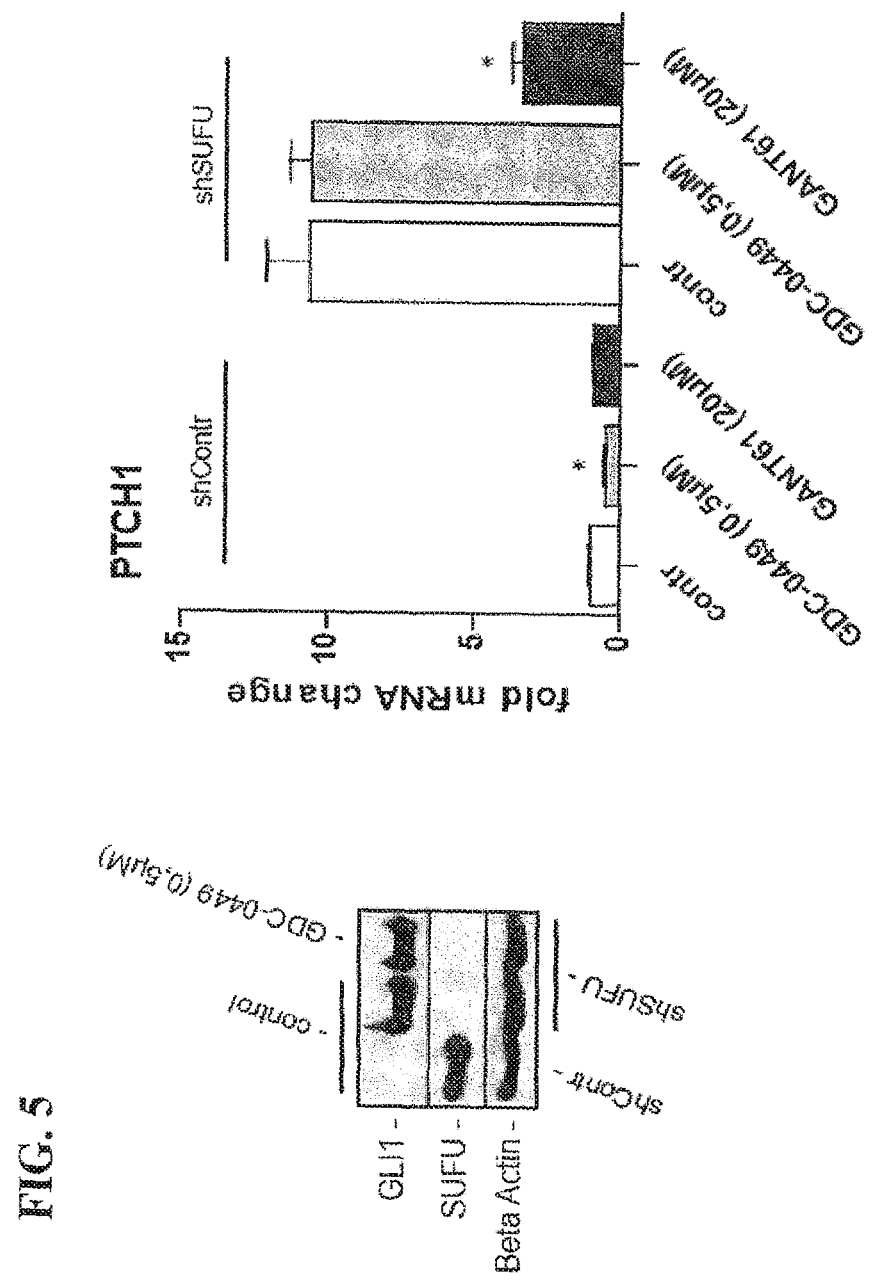
FIG. 5: RNAi mediated knockdown of SUFU (shSUFU) in DAOY cells leads to SMO independent activation of GLI1 expression that is resistant to SMO inhibition. Western blot (left panel) and qPCR analysis (right panel) showing SMO-independent HH target gene activation i.e. GLI1 protein and PTCH1 mRNA expression. In SUFU knockdown cells, activation of GLI1 and PTCH1 expression is resistant to treatment with GDC-0449. The cells nonetheless remain sensitive to treatment with GANT61 (shown only for PTCH1 expression). qPCR data represent fold change values compared to non-target shRNA (shContr).

Example 2—Targeting DYRK1B Inhibits Smoothened-Independent GLI Activity in Human Cancer Cells Resistance of DAOY cells to SMO-inhibitors by RNAi mediated inhibition of SUFU expression, a critical negative regulator of GLI proteins acting downstream of SMO was generated. As shown in FIG. 5, stable lentiviral RNAi-mediated SUFU knockdown (for details see Material and Methods, RNA interference and lentiviral transduction) in DAOY cells resulted in activation of GLI1 expression. Notably and unlike control knockdown cells, GLI1 expression in SUFU depleted DAOY cells was unaffected by GDC-0449 (2-chloro-N-(4-chloro-3-(pyridin-2-yl)phenyl)-4-(methylsulfonyl)benzamide; INN Vismodegib) treatment, indicating resistance to SMO-inhibition. By contrast, SUFU-knockdown cells retained their sensitivity to the GLI antagonist GANT61 (2,2'-[[Dihydro-2-(4-pyridinyl)-1,3 (2H,4H)-pyrimidinediyl]bis-(methylene)]bis[N,N-dimethylbenzenamine), as evidenced by down-regulation of GLI1 and PTCH1 mRNA expression.

Figure 6:
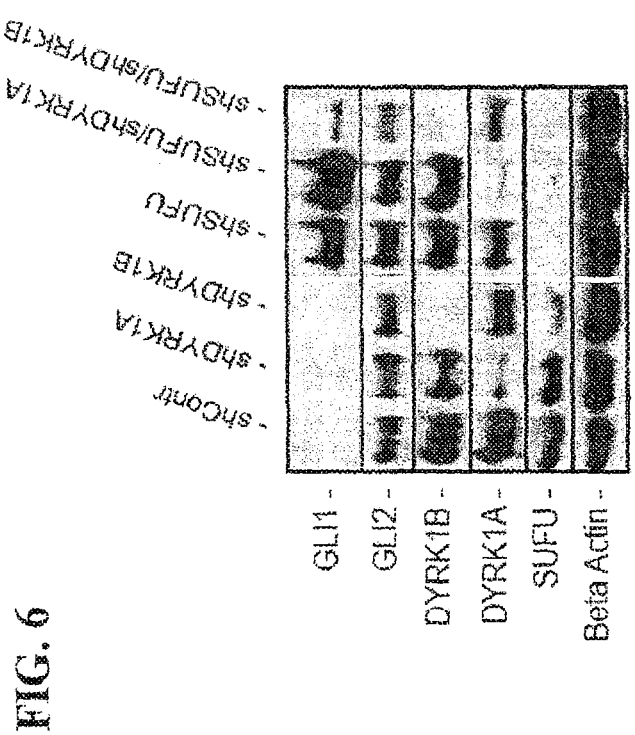
FIG. 6: Western blot analysis showing effects of knockdown of DYRK1A/B alone or in combination with shSUFU on GLI1 and GLI2 protein expression in DAOY cells. Only DYRK1B inhibition reduces GLI1 protein levels in SUFU depleted cells.

Of note, RNAi-mediated inhibition of DYRK1B prevented GLI1 expression even in SUFU-depleted, SMO-inhibitor resistant DAOY cells, while DYRK1A inhibition did not reduce GLI1 activation in this cellular model (FIG. 6).

Example 2 A

Figure 7:
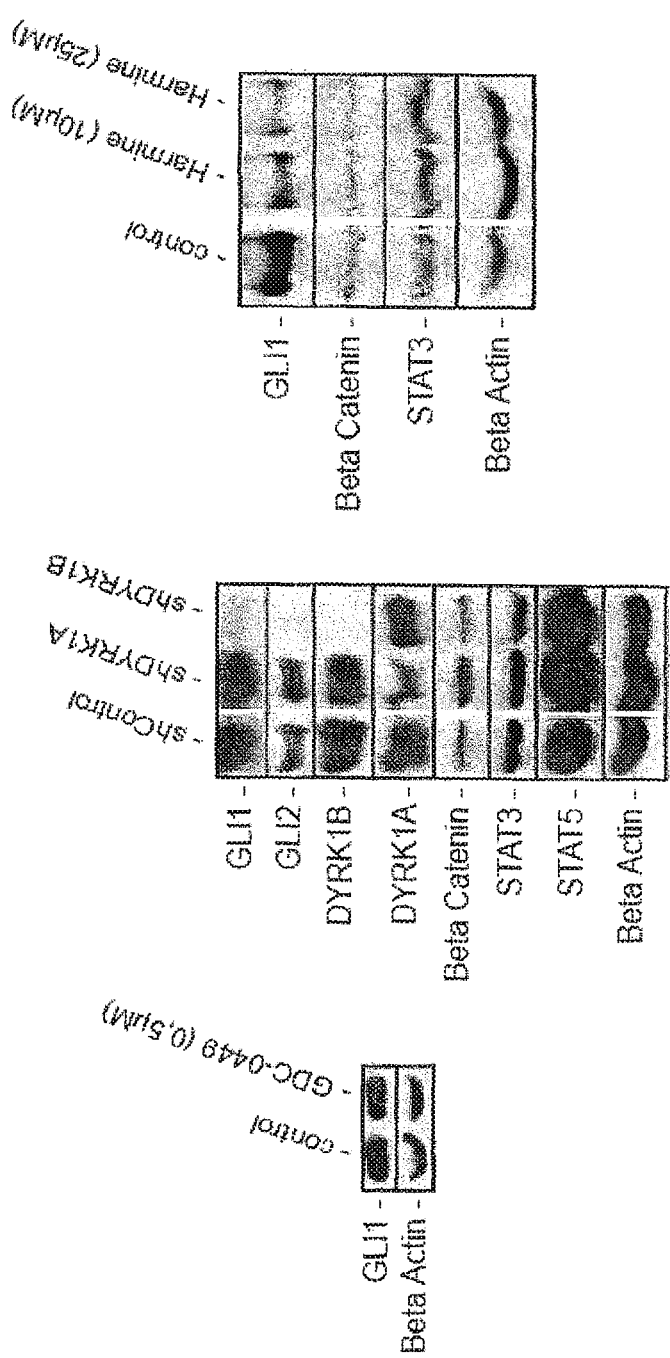
FIG. 7: Left panel: Western blot analysis of PANC1 cells showing resistance of GLI1 protein expression to SMO inhibition by GDC-0449 treatment. Middle panel: Effect of RNAi mediated knockdown of DYRK1A or DYRK1B on GLI1, GLI2, Beta Catenin, STAT3 and STAT5. Right panel: Effect of Harmine treatment on GLI1, Beta Catenin and STAT3 expression. In both cases, only DYRK1B inhibition reduces GLI1 and/or GLI2 protein levels in PANC1 cells. The general transcription factors Beta Catenin, STAT3 and STAT5 are essentially unaffected by DYRK1A and DYRK1B inhibition.
Figure 8:
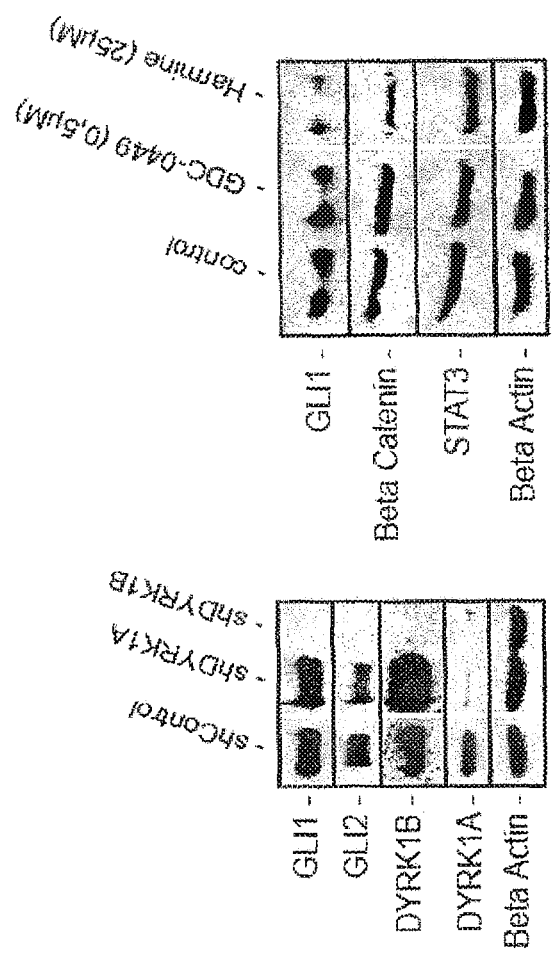
FIG. 8: Left panel: EWS (Ewing sarcoma) cell line (A673) Western blot analysis showing the effect of RNAi mediated knockdown of DYRK1A or DYRK1B on GLI1 and GLI2. Right panel: Effect of Harmine and GDC-0449 on GLI1, Beta Catenin and STAT3 protein expression. In both cases DYRK1B inhibition reduces GLI1 and/or GLI2 protein levels in EWS cells. The general transcription factor Beta Catenin is essentially unaffected by DYRK1A and DYRK1B inhibition.

The function of DYRK1 isoforms in SMO-independent/GLI-dependent pancreatic cancer and Ewing's sarcoma (EWS) cell lines PANC1 and A673, respectively, was analyzed. PANC1 cells display SMO-independent, TGFβ-driven expression of GLI1 and GLI2, whereas A673 cells express GLI1 as a direct transcriptional target of the fusion oncoprotein EWS/FLI1s. The inability of GDC-0449 treatment (0.5 μM) to decrease GLI expression (FIG. 7 left panel, FIG. 8 right panel) demonstrates SMO-independent expression of GLI in both cell lines. Importantly and in line with the presented data on SUFU-depleted medulloblastoma cells, genetic perturbation of DYRK1B, but not of DYRK1A, led to a reduction of endogenous GLI1 and GLI2 protein expression. Inhibition of GLI1/2 expression by DYRK1B targeting is a specific effect, as DYRK1B knockdown did not alter the abundance of other transcriptional regulators such as STAT3, STAT5 or β-Catenin, neither in PANC1 (FIG. 7 middle panel) nor in A673 cells (FIG. 8 left panel). The genetic data was confirmed by chemical inhibition of DYRK1 using Harmine as described above. Like RNAi-mediated inhibition of DYRK1B, Harmine treatment of PANC1 and A673 reduced levels of GLI1 (FIGS. 7 and 8 right panels).

Figure 9:
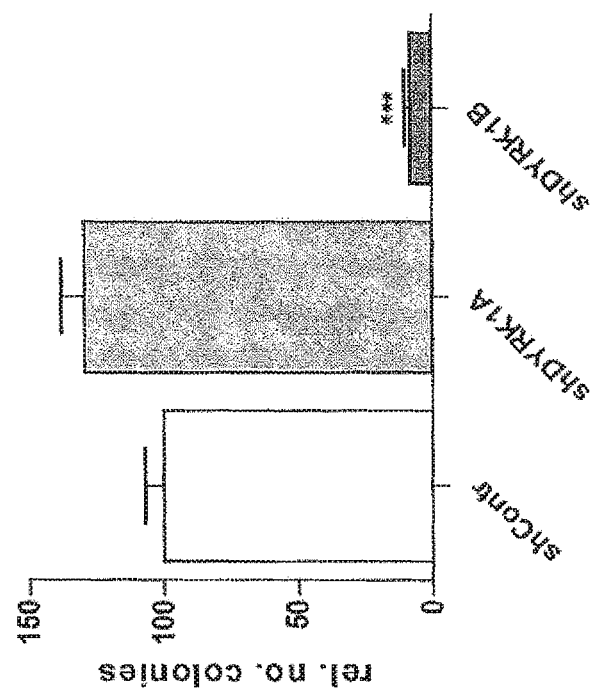
FIG. 9: Effect of RNAi mediated knockdown of DYRK1A or DYRK1B on clonal growth of tumor-initiating PANC1 pancreatic cancer cells in anchorage-independent 3D cultures. The right panel represents the quantification of the 3D cultures shown in the left panel. Data represent the mean values of at least 3 independent experiments (error bars represent SEM. ***p<0.001). Only DYRK1B repression reduces colony numbers.
Figure 9:
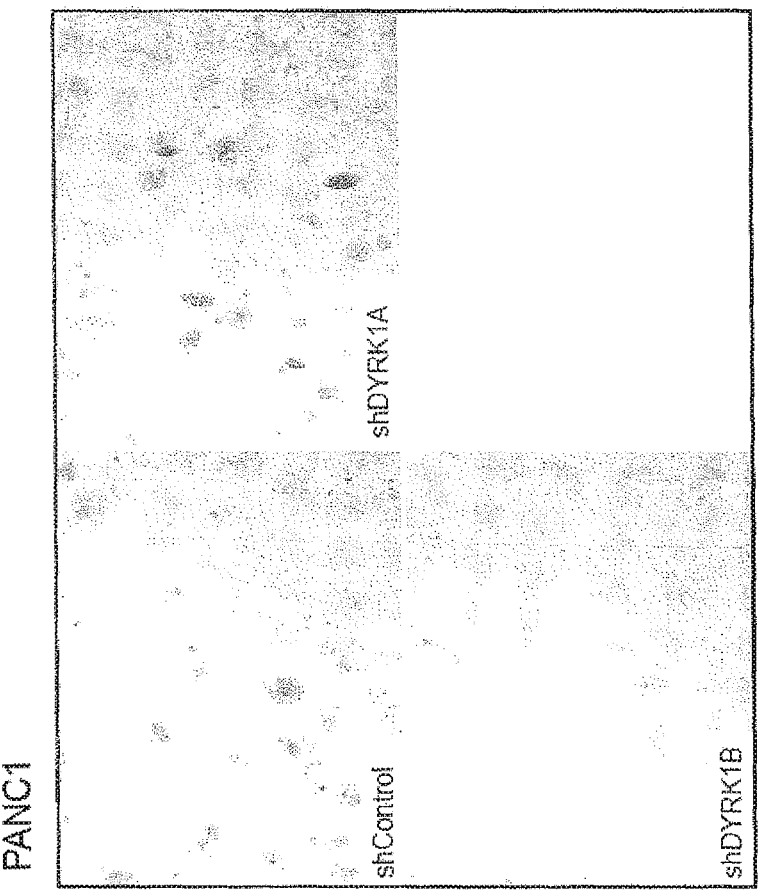
Figure 10:
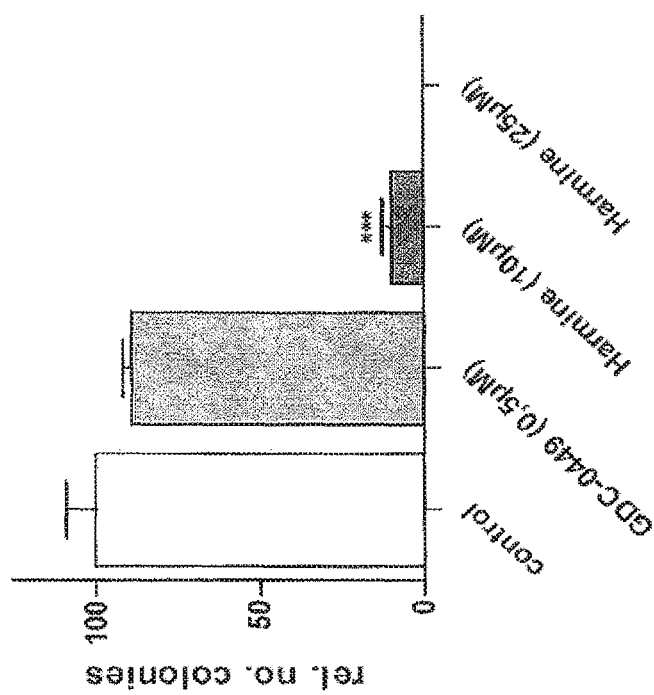
FIG. 10: Results of pharmacological inhibition of DYRK1 on clonal growth of tumor-initiating PANC1 pancreatic cancer cells in anchorage-independent 3D cultures. The right panel represents the quantification of the 3D cultures shown in the left panel. Data represent the mean values of at least 3 independent experiments (error bars represent SEM. ***p<0.001). Only DYRK1 inhibition by Harmine but not SMO inhibition by GDC-0449 reduces sphere numbers.
Figure 10:
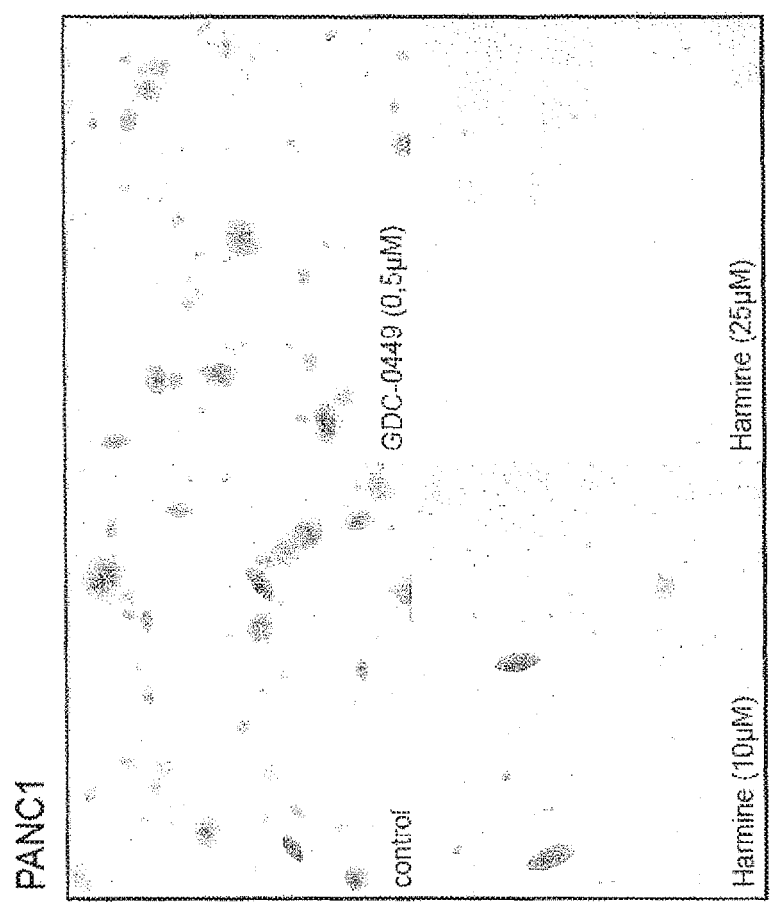
Figure 11:
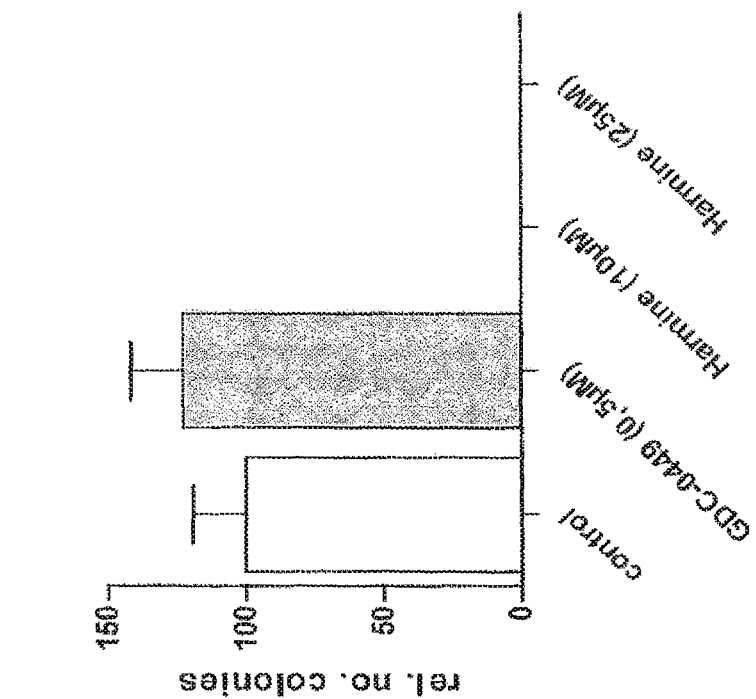
FIG. 11: Results of pharmacological inhibition of DYRK1 on clonal growth of tumor-initiating L3.6p1 pancreatic cancer cells in anchorage-independent 3D cultures. The right panel represents the quantification of the 3D cultures shown in the left panel. Data represent the mean values of at least 3 independent experiments (error bars represent SEM. ***p<0.001). Only DYRK1 inhibition by Harmine but not SMO inhibition by GDC-0449 reduces sphere numbers.
Figure 11:
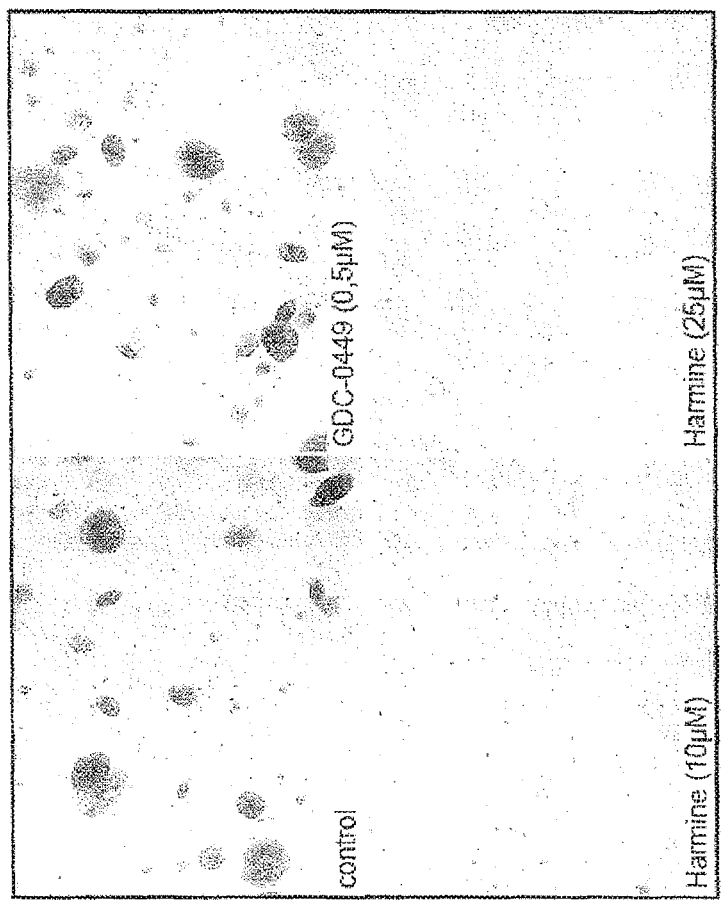

Example 3—DYRK1B Function is Essential for Tumor-Initiating Pancreatic Cancer Cells The role of DYRK1B in GLI-dependent clonogenic growth of tumor-initiating cancer cells (PANC1 and L3.6p1 was addressed. An established 3D tumorsphere assay, suitable to monitor and quantify the growth of tumor-initiating pancreatic cancer stem cells under non-adherent conditions (see Eberl et al., 2012, incorporated herein by reference) was employed to analyze the effect of DYRK1B inhibition on the clonogenic growth properties of tumor-initiating pancreatic cancer cells. As shown in FIG. 9, RNAi mediated knockdown of DYRK1B, but not of DYRK1A, efficiently prevented clonogenic growth of tumor-initiating cells, in line with the results on the selective requirement of DYRK1B for GLI1 expression. In contrast the result obtained for the inhibition of DYRK1A, the pancreatic cancer stem cells do not form colonies upon inhibition of DYRK1B with shRNA, as evidenced by the lack of tumor cell spheroids. Like RNAi-mediated DYRK1B inhibition, Harmine treatment reduced clonogenic growth of PANC1 cells, whereas SMO-inhibition by GDC-0449 did not affect the growth of tumor-initiating cells (FIG. 10, FIG. 11). In the aforementioned experiments the viability of the cells was not affected by inhibition of DYRK1B (data not shown herein).

Example 4—Xenograft Assays

Figure 12:
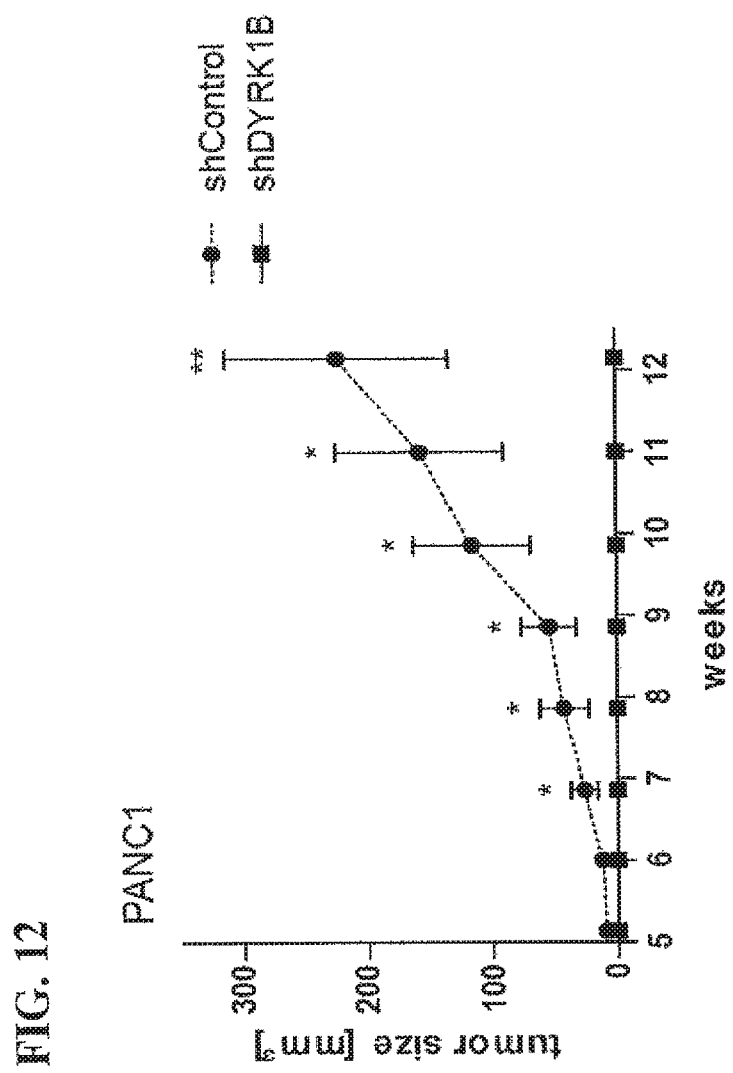
FIG. 12: Effect of RNAi mediated knockdown of DYRK1B on in vivo tumor growth of pancreatic cancer cells. $1 \times 10^6$ pancreatic cancer cells (PANC1) either lentivirally transduced with non-target control shRNA (shContr) or with shRNA specific for DYRK1B (shDYRK1B) were grafted onto nude mice and tumor growth was monitored over a period of 12 weeks. (n=7; Error bars represent SEM. *p<0.05, **p<0.01).
Figure 13:
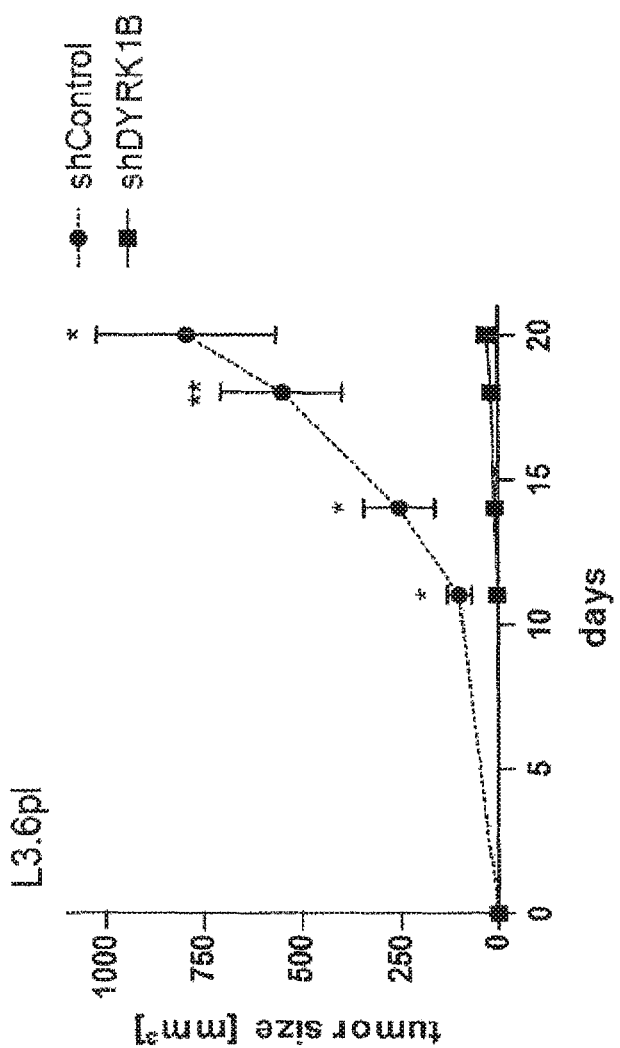
FIG. 13: Effect of RNAi mediated knockdown of DYRK1B on in vivo tumor growth of pancreatic cancer cells. $1 \times 10^5$ pancreatic cancer cells (L3.6p1) either lentivirally transduced with non-target control shRNA (shContr) or with shRNA specific for DYRK1B (shDYRK1B) were grafted onto nude mice and tumor growth was monitored over a period of 3 weeks. (n=8; Error bars represent SEM. *p<0.05, **p<0.01).

Xenograft assays with PANC1 and L3.6p1 cancer cells were prepared as described above. The PANC1 and L3.6p1 cancer cells were beforehand depleted of DYRK1B by DYRK1B shRNA transduction as described above. In agreement with the in vitro data, DYRK1B knockdown reduced in vivo growth of pancreatic cancer cells compared to control knockdown cells expressing non-target shRNA (FIG. 12, FIG. 13).

In summary, DYRK1B is a critical factor required for GLI1 expression in both SMO-dependent and SMO-independent human cancer cells, while DYRK1A function is largely dispensable for GLI1 expression. The essential requirement of DYRK1B in tumor-initiating pancreatic cells suggests that selective targeting of DYRK1B in HH/GLI-dependent human cancers is therefore a promising therapeutic approach, also effective in cells resistant to SMO-targeting such as pancreatic cancer and Ewing's sarcoma cells.

Example 5—In Vitro DYRK1A/DYRK1B Kinase Assay: Compound P

The assay was carried out by Reaction Biology Corp., Malverne, Pa., USA according to specifications by Reaction Biology Corp., as detailed herein below and further described in Anastassiadis et al., Nature Biotechnology, 29 (2011) 1039-1045.

DYRK1A: The substrate DYRKtide (synthetic peptide RRRFRPASPLRGPPK) (SEQ ID NO: 5) was dissolved in freshly prepared Base Reaction Buffer (20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO) at a concentration of 20 µM. DYRK1A was added to the substrate solution in a concentration of 0.3 nM and gently mixed. Compound dilution series in DMSO were added to the reaction, followed 20 min later by addition of a mixture of ATP and $^{33}P$ ATP (0.01 µCi/µl final) to a final concentration of 10 µM. Reactions proceeded at 25° C. for 120 min, followed by spotting onto P81 ion exchange filter paper. Unbound phosphate was removed by extensive washing of the filters in 0.75% phosphoric acid. After subtraction of background derived from control reactions containing inactive enzyme, kinase activity data were expressed as the percent remaining kinase activity in test samples compared to vehicle (DMSO) reactions. $IC_{50}$ values and curve fits were obtained using Prism (Graph Pad Software).

The assay for DYRK1B was carried out as described above for DYRK1A, with the exception that instead of DYRK1A, DYRK1B was added to the substrate solution and gently mixed.

DYRK1A and DYRK1B used in the above assays are further described in the below table:

| | Genbank Accession # | Protein Accession # | Clone | Expression | Tag |
|---|---|---|---|---|---|
| DYRK1A | NP_001387 | Q13627 | full-length | Insect | N-terminal GST |
| DYRK1B | NP_004705 | Q9Y463 | full-length | Insect | N-terminal GST |

Compound dilution series which was applied for 4SC compound P, and which is exemplary for compound dilution series applicable in the above DYRK assays: DYRK1A: 3,00E-05 M, 1,00E-05 M, 3,33E-06 M, 1,11E-06 M, 3,70E-07 M, 1,23E-07 M, 4,12E-08 M, 1,37E-08 M, 4,57E-09 M, 1,52E-09 M; DYRK 1B: 1,00E-05 M, 3,33E-06 M, 1,11E-06 M, 3,70E-07 M, 1,23E-07 M, 4,12E-08 M, 1,37E-08 M, 4,57E-09 M, 1,52E-09 M, 5,08E-10 M.

In said assays, Compound P has an $IC_{50}$ of 22.2 nM (DYRK1A) and 54.8 nM (DYRK1B).

Example 6—DYRK1B Analogy Model

For identifying additional DYRK1B inhibitors a computational approach with the software 4SCan (for additional information and a detailed description of the method see: Seifert, H. J.; Wolf, K.; Vitt, D. Biosilico 2003, 1, 143 and/or Patent EP 1094 415 A2) was used. This iterative process starts by docking a small subset of a compound library into the target, in the present case DYRK1B. From the results a model for inhibitors based on molecular descriptors is generated and subsequently used to choose the next set of compounds for docking. The process is finished, after a predefined number of compounds are submitted to docking. 4SCan screening was conducted in 10 iterations docking 5,000 molecules each. Charged strong acids/bases were neutralized with the 'wash' function in the software MOE 2011.10 by adding/removing corresponding hydrogen atoms for the 2,000 top hits in order to convert the structure to a chemical name within ChemDrawExcel 12.0. Therefore a single compound name can exhibit multiple docking scores, depending on its protonation and tautomerization. The docking score calculated by the software ProPose (for additional information and a detailed description of the method see: Markus H. J. Seifert et al., Mol Model (2004) 10:342-357 is proportional to the change in Gibbs free energy upon ligand binding.

The 3D-structure of DYRK1B necessary for the aforementioned docking studies was not available from The Research Collaboratory for Structural Bioinformatics PDB (http://www.rcsb.org/pdb/) and was therefore generated by homology modeling using the closely related DYRK1A (G Manning et al. (2002) Science 298:1912-1934) as template. The template structure used is an X-ray structure of containing 4 representations (chains) of DYRK1A in complex with a ligand. The model is based on DYRK1A chain (A), wherein the side chain of Methionine 240 was remodeled to compensate for clashes with the ligand and because said Methionine conformation is different from the one in the other three chains (B-D) present in the X-ray structure.

Homology modeling (Jones, T. A. et al., EMBO J. 5 (1986) 819-822; Blundell T L et al. (1987) Nature 326 (6111): 347-352) was carried out with the software MOE 2011.10, using the implemented approach with slightly varied standard parameters (Model refinement optimizations were set to 'fine' method). As DYRK1A and DYRK1B share 83.8% amino acid sequence homology, additional post-processing of the generated model was unnecessary.

The ligand binding site was determined by superposing the protein backbone of template and homology model with the software MOE 2011.10 and thus transferring the ligand of the DYRK1A X-ray structure to the homology model. Based on this ligand pose, the model used for ProPose docking in the 4SCan screening was generated by including all receptor atoms situated at a distance of 6.0 Å or less from at least one atom of the ligand, as potential interaction partners. The atom coordinates of the active site receptor atoms (6.0 Å radius) of the aforementioned model are shown below in pdb compatible format. All other atoms were omitted, as they are not essential to the modeling method as used herein because the active site conformations is kept constant in said method.

| HEADER | | | Q9Y463 DYRK1B_HUMAN 4SC Active Site Homology Model | | | | | | |
|---|---|---|---|---|---|---|---|---|---|
| ATOM | 1 | CA | ILE | 117 | 46.444 | 22.603 | −38.607 | 1.00 | 0.00 |
| ATOM | 2 | C | ILE | 117 | 45.321 | 22.977 | −39.591 | 1.00 | 0.00 |
| ATOM | 3 | O | ILE | 117 | 44.878 | 22.154 | −40.393 | 1.00 | 0.00 |
| ATOM | 4 | CB | ILE | 117 | 46.012 | 21.520 | −37.590 | 1.00 | 0.00 |
| ATOM | 5 | CG1 | ILE | 117 | 45.028 | 22.039 | −36.525 | 1.00 | 0.00 |
| ATOM | 6 | CG2 | ILE | 117 | 47.257 | 20.892 | −36.947 | 1.00 | 0.00 |
| ATOM | 7 | CD1 | ILE | 117 | 44.383 | 20.924 | −35.708 | 1.00 | 0.00 |
| ATOM | 8 | HA | ILE | 117 | 47.202 | 22.143 | −39.256 | 1.00 | 0.00 |
| ATOM | 9 | HB | ILE | 117 | 45.503 | 20.724 | −38.152 | 1.00 | 0.00 |
| ATOM | 10 | HG12 | ILE | 117 | 45.536 | 22.723 | −35.836 | 1.00 | 0.00 |
| ATOM | 11 | HG13 | ILE | 117 | 44.226 | 22.604 | −37.012 | 1.00 | 0.00 |
| ATOM | 12 | HG21 | ILE | 117 | 47.950 | 20.529 | −37.715 | 1.00 | 0.00 |
| ATOM | 13 | HG22 | ILE | 117 | 47.794 | 21.617 | −36.327 | 1.00 | 0.00 |
| ATOM | 14 | HG23 | ILE | 117 | 46.996 | 20.033 | −36.322 | 1.00 | 0.00 |
| ATOM | 15 | HD11 | ILE | 117 | 43.874 | 20.206 | −36.359 | 1.00 | 0.00 |
| ATOM | 16 | HD12 | ILE | 117 | 45.119 | 20.385 | −35.106 | 1.00 | 0.00 |
| ATOM | 17 | HD13 | ILE | 117 | 43.640 | 21.341 | −35.021 | 1.00 | 0.00 |
| ATOM | 18 | N | GLY | 118 | 44.816 | 24.259 | −39.464 | 1.00 | 0.00 |
| ATOM | 19 | HA3 | GLY | 118 | 42.840 | 24.371 | −40.075 | 1.00 | 0.00 |
| ATOM | 20 | HA3 | GLY | 120 | 39.437 | 29.050 | −42.282 | 1.00 | 0.00 |
| ATOM | 21 | CB | PHE | 122 | 35.945 | 31.516 | −39.362 | 1.00 | 0.00 |
| ATOM | 22 | CG | PHE | 122 | 36.599 | 30.152 | −39.232 | 1.00 | 0.00 |
| ATOM | 23 | CD1 | PHE | 122 | 37.459 | 29.867 | −38.161 | 1.00 | 0.00 |
| ATOM | 24 | CD2 | PHE | 122 | 36.356 | 29.150 | −40.181 | 1.00 | 0.00 |
| ATOM | 25 | CE1 | PHE | 122 | 38.102 | 28.631 | −38.070 | 1.00 | 0.00 |
| ATOM | 26 | CE2 | PHE | 122 | 36.970 | 27.900 | −40.070 | 1.00 | 0.00 |
| ATOM | 27 | CZ | PHE | 122 | 37.852 | 27.645 | −39.022 | 1.00 | 0.00 |
| ATOM | 28 | HB1 | PHE | 122 | 35.620 | 31.836 | −38.363 | 1.00 | 0.00 |
| ATOM | 29 | HB2 | PHE | 122 | 35.024 | 31.412 | −39.952 | 1.00 | 0.00 |
| ATOM | 30 | HD1 | PHE | 122 | 37.637 | 30.611 | −37.386 | 1.00 | 0.00 |
| ATOM | 31 | HD2 | PHE | 122 | 35.668 | 29.323 | −41.005 | 1.00 | 0.00 |
| ATOM | 32 | HE1 | PHE | 122 | 38.777 | 28.429 | −37.242 | 1.00 | 0.00 |
| ATOM | 33 | HE2 | PHE | 122 | 36.744 | 27.120 | −40.793 | 1.00 | 0.00 |
| ATOM | 34 | HZ | PHE | 122 | 38.321 | 26.669 | −38.937 | 1.00 | 0.00 |
| ATOM | 35 | HA3 | GLY | 123 | 39.770 | 31.894 | −37.417 | 1.00 | 0.00 |
| ATOM | 36 | CB | VAL | 125 | 42.171 | 25.197 | −36.304 | 1.00 | 0.00 |
| ATOM | 37 | CG1 | VAL | 125 | 42.016 | 24.133 | −35.210 | 1.00 | 0.00 |
| ATOM | 38 | CG2 | VAL | 125 | 40.783 | 25.712 | −36.698 | 1.00 | 0.00 |
| ATOM | 39 | HB | VAL | 125 | 42.614 | 24.718 | −37.186 | 1.00 | 0.00 |
| ATOM | 40 | HG11 | VAL | 125 | 42.986 | 23.729 | −34.905 | 1.00 | 0.00 |
| ATOM | 41 | HG12 | VAL | 125 | 41.533 | 24.549 | −34.319 | 1.00 | 0.00 |
| ATOM | 42 | HG13 | VAL | 125 | 41.406 | 23.297 | −35.566 | 1.00 | 0.00 |
| ATOM | 43 | HG21 | VAL | 125 | 40.309 | 26.251 | −35.870 | 1.00 | 0.00 |
| ATOM | 44 | HG22 | VAL | 125 | 40.840 | 26.388 | −37.557 | 1.00 | 0.00 |
| ATOM | 45 | HG23 | VAL | 125 | 40.126 | 24.882 | −36.981 | 1.00 | 0.00 |
| ATOM | 46 | CD | LYS | 127 | 48.623 | 18.856 | −33.368 | 1.00 | 0.00 |
| ATOM | 47 | HD | LYS | 127 | 47.653 | 18.459 | −33.691 | 1.00 | 0.00 |
| ATOM | 48 | HB2 | LYS | 127 | 47.230 | 21.089 | −33.947 | 1.00 | 0.00 |
| ATOM | 49 | HE2 | LYS | 127 | 49.255 | 16.792 | −33.199 | 1.00 | 0.00 |
| ATOM | 50 | N | ALA | 138 | 43.208 | 21.773 | −29.143 | 1.00 | 0.00 |
| ATOM | 51 | CA | ALA | 138 | 43.020 | 22.343 | −30.474 | 1.00 | 0.00 |
| ATOM | 52 | C | ALA | 138 | 42.412 | 23.727 | −30.262 | 1.00 | 0.00 |
| ATOM | 53 | O | ALA | 138 | 41.276 | 23.894 | −29.805 | 1.00 | 0.00 |
| ATOM | 54 | CB | ALA | 138 | 42.078 | 21.495 | −31.312 | 1.00 | 0.00 |
| ATOM | 55 | H | ALA | 138 | 42.362 | 21.611 | −28.570 | 1.00 | 0.00 |
| ATOM | 56 | HA | ALA | 138 | 43.984 | 22.424 | −30.986 | 1.00 | 0.00 |
| ATOM | 57 | HB1 | ALA | 138 | 42.524 | 20.522 | −31.521 | 1.00 | 0.00 |
| ATOM | 58 | HB2 | ALA | 138 | 41.124 | 21.322 | −30.803 | 1.00 | 0.00 |
| ATOM | 59 | HB3 | ALA | 138 | 41.862 | 21.982 | −32.269 | 1.00 | 0.00 |
| ATOM | 60 | N | LYS | 140 | 41.179 | 27.330 | −31.393 | 1.00 | 0.00 |
| ATOM | 61 | CA | LYS | 140 | 40.558 | 28.079 | −32.487 | 1.00 | 0.00 |
| ATOM | 62 | CB | LYS | 140 | 39.067 | 27.736 | −32.600 | 1.00 | 0.00 |
| ATOM | 63 | CG | LYS | 140 | 38.280 | 28.451 | −33.716 | 1.00 | 0.00 |
| ATOM | 64 | CD | LYS | 140 | 36.793 | 28.031 | −33.699 | 1.00 | 0.00 |
| ATOM | 65 | CE | LYS | 140 | 35.949 | 28.688 | −34.788 | 1.00 | 0.00 |
| ATOM | 66 | NZ | LYS | 140 | 34.554 | 28.235 | −34.711 | 1.00 | 0.00 |
| ATOM | 67 | H | LYS | 140 | 40.639 | 27.249 | −30.516 | 1.00 | 0.00 |
| ATOM | 68 | HA | LYS | 140 | 41.064 | 27.832 | −33.424 | 1.00 | 0.00 |

-continued

| HEADER | | | Q9Y463 DYRK1B_HUMAN 4SC Active Site Homology Model | | | | | |
|---|---|---|---|---|---|---|---|---|
| ATOM | 69 | HB2 | LYS | 140 | 38.977 | 26.652 | −32.748 | 1.00 0.00 |
| ATOM | 70 | HB3 | LYS | 140 | 38.588 | 27.962 | −31.645 | 1.00 0.00 |
| ATOM | 71 | HG2 | LYS | 140 | 38.351 | 29.536 | −33.586 | 1.00 0.00 |
| ATOM | 72 | HG3 | LYS | 140 | 38.723 | 28.206 | −34.688 | 1.00 0.00 |
| ATOM | 73 | HD2 | LYS | 140 | 36.364 | 28.271 | −32.721 | 1.00 0.00 |
| ATOM | 74 | HD3 | LYS | 140 | 36.734 | 26.941 | −33.814 | 1.00 0.00 |
| ATOM | 75 | HE2 | LYS | 140 | 36.314 | 28.393 | −35.774 | 1.00 0.00 |
| ATOM | 76 | HE3 | LYS | 140 | 35.942 | 29.779 | −34.716 | 1.00 0.00 |
| ATOM | 77 | HZ1 | LYS | 140 | 34.398 | 27.306 | −34.315 | 1.00 0.00 |
| ATOM | 78 | HZ2 | LYS | 140 | 33.844 | 28.848 | −34.166 | 1.00 0.00 |
| ATOM | 79 | HZ3 | LYS | 140 | 34.091 | 28.108 | −35.696 | 1.00 0.00 |
| ATOM | 80 | CD | GLU | 155 | 31.851 | 28.520 | −33.176 | 1.00 0.00 |
| ATOM | 81 | OE1 | GLU | 155 | 32.845 | 29.268 | −33.442 | 1.00 0.00 |
| ATOM | 82 | OE2 | GLU | 155 | 31.639 | 27.392 | −33.707 | 1.00 0.00 |
| ATOM | 83 | CD1 | LEU | 159 | 32.388 | 26.728 | −29.358 | 1.00 0.00 |
| ATOM | 84 | HD11 | LEU | 159 | 33.148 | 26.152 | −28.828 | 1.00 0.00 |
| ATOM | 85 | HD12 | LEU | 159 | 32.632 | 26.737 | −30.423 | 1.00 0.00 |
| ATOM | 86 | HD23 | LEU | 159 | 31.272 | 24.698 | −30.743 | 1.00 0.00 |
| ATOM | 87 | CB | VAL | 174 | 34.026 | 19.628 | −30.894 | 1.00 0.00 |
| ATOM | 88 | CG1 | VAL | 174 | 33.453 | 21.036 | −31.057 | 1.00 0.00 |
| ATOM | 89 | CG2 | VAL | 174 | 35.503 | 19.686 | −30.501 | 1.00 0.00 |
| ATOM | 90 | HB | VAL | 174 | 33.983 | 19.142 | −31.876 | 1.00 0.00 |
| ATOM | 91 | HG11 | VAL | 174 | 32.423 | 21.013 | −31.423 | 1.00 0.00 |
| ATOM | 92 | HG12 | VAL | 174 | 33.452 | 21.582 | −30.112 | 1.00 0.00 |
| ATOM | 93 | HG13 | VAL | 174 | 34.047 | 21.613 | −31.773 | 1.00 0.00 |
| ATOM | 94 | HG21 | VAL | 174 | 35.640 | 20.129 | −29.512 | 1.00 0.00 |
| ATOM | 95 | HG22 | VAL | 174 | 35.936 | 18.681 | −30.482 | 1.00 0.00 |
| ATOM | 96 | HG23 | VAL | 174 | 36.077 | 20.281 | −31.218 | 1.00 0.00 |
| ATOM | 97 | CD1 | LEU | 188 | 35.087 | 29.871 | −30.220 | 1.00 0.00 |
| ATOM | 98 | HD11 | LEU | 188 | 35.510 | 29.622 | −31.195 | 1.00 0.00 |
| ATOM | 99 | HD12 | LEU | 188 | 34.458 | 29.034 | −29.898 | 1.00 0.00 |
| ATOM | 100 | HB2 | LEU | 188 | 37.499 | 28.667 | −30.023 | 1.00 0.00 |
| ATOM | 101 | HB3 | LEU | 188 | 36.487 | 28.059 | −28.746 | 1.00 0.00 |
| ATOM | 102 | N | PHE | 190 | 39.437 | 23.853 | −27.713 | 1.00 0.00 |
| ATOM | 103 | CA | PHE | 190 | 38.715 | 22.593 | −27.897 | 1.00 0.00 |
| ATOM | 104 | C | PHE | 190 | 39.656 | 21.401 | −27.640 | 1.00 0.00 |
| ATOM | 105 | O | PHE | 190 | 40.887 | 21.468 | −27.690 | 1.00 0.00 |
| ATOM | 106 | CB | PHE | 190 | 38.196 | 22.432 | −29.332 | 1.00 0.00 |
| ATOM | 107 | CG | PHE | 190 | 37.193 | 23.463 | −29.762 | 1.00 0.00 |
| ATOM | 108 | CD1 | PHE | 190 | 35.825 | 23.260 | −29.549 | 1.00 0.00 |
| ATOM | 109 | CD2 | PHE | 190 | 37.621 | 24.621 | −30.416 | 1.00 0.00 |
| ATOM | 110 | CE1 | PHE | 190 | 34.894 | 24.161 | −30.059 | 1.00 0.00 |
| ATOM | 111 | CE2 | PHE | 190 | 36.684 | 25.531 | −30.889 | 1.00 0.00 |
| ATOM | 112 | CZ | PHE | 190 | 35.326 | 25.292 | −30.740 | 1.00 0.00 |
| ATOM | 113 | H | PHE | 190 | 40.182 | 24.026 | −28.400 | 1.00 0.00 |
| ATOM | 114 | HA | PHE | 190 | 37.894 | 22.547 | −27.180 | 1.00 0.00 |
| ATOM | 115 | HB2 | PHE | 190 | 39.035 | 22.439 | −30.040 | 1.00 0.00 |
| ATOM | 116 | HB3 | PHE | 190 | 37.742 | 21.441 | −29.464 | 1.00 0.00 |
| ATOM | 117 | HD1 | PHE | 190 | 35.469 | 22.390 | −29.003 | 1.00 0.00 |
| ATOM | 118 | HD2 | PHE | 190 | 38.680 | 24.812 | −30.575 | 1.00 0.00 |
| ATOM | 119 | HE1 | PHE | 190 | 33.832 | 23.974 | −29.934 | 1.00 0.00 |
| ATOM | 120 | HE2 | PHE | 190 | 37.010 | 26.428 | −31.393 | 1.00 0.00 |
| ATOM | 121 | HZ | PHE | 190 | 34.612 | 25.998 | −31.146 | 1.00 0.00 |
| ATOM | 122 | N | GLU | 191 | 38.969 | 20.205 | −27.492 | 1.00 0.00 |
| ATOM | 123 | CA | GLU | 191 | 39.667 | 18.923 | −27.543 | 1.00 0.00 |
| ATOM | 124 | C | GLU | 191 | 40.290 | 18.646 | −28.936 | 1.00 0.00 |
| ATOM | 125 | O | GLU | 191 | 39.723 | 18.913 | −29.996 | 1.00 0.00 |
| ATOM | 126 | CB | GLU | 191 | 38.746 | 17.767 | −27.127 | 1.00 0.00 |
| ATOM | 127 | CG | GLU | 191 | 37.523 | 17.546 | −28.022 | 1.00 0.00 |
| ATOM | 128 | H | GLU | 191 | 37.954 | 20.223 | −27.335 | 1.00 0.00 |
| ATOM | 129 | HA | GLU | 191 | 40.487 | 18.992 | −26.818 | 1.00 0.00 |
| ATOM | 130 | HB | GLU | 191 | 39.333 | 16.840 | −27.087 | 1.00 0.00 |
| ATOM | 131 | HG1 | GLU | 191 | 37.831 | 17.159 | −28.999 | 1.00 0.00 |
| ATOM | 132 | HG2 | GLU | 191 | 36.999 | 18.490 | −28.192 | 1.00 0.00 |
| ATOM | 133 | N | LEU | 192 | 41.536 | 18.024 | −28.873 | 1.00 0.00 |
| ATOM | 134 | CA | LEU | 192 | 42.277 | 17.645 | −30.077 | 1.00 0.00 |
| ATOM | 135 | C | LEU | 192 | 41.686 | 16.319 | −30.579 | 1.00 0.00 |
| ATOM | 136 | O | LEU | 192 | 41.266 | 15.439 | −29.829 | 1.00 0.00 |
| ATOM | 137 | CB | LEU | 192 | 43.779 | 17.517 | −29.784 | 1.00 0.00 |
| ATOM | 138 | CG | LEU | 192 | 44.676 | 17.299 | −31.021 | 1.00 0.00 |
| ATOM | 139 | CD1 | LEU | 192 | 44.642 | 18.482 | −31.990 | 1.00 0.00 |
| ATOM | 140 | CD2 | LEU | 192 | 46.120 | 17.042 | −30.587 | 1.00 0.00 |
| ATOM | 141 | H | LEU | 192 | 41.949 | 17.792 | −27.973 | 1.00 0.00 |
| ATOM | 142 | HA | LEU | 192 | 42.090 | 18.421 | −30.823 | 1.00 0.00 |
| ATOM | 143 | HB2 | LEU | 192 | 44.116 | 18.421 | −29.259 | 1.00 0.00 |
| ATOM | 144 | HB3 | LEU | 192 | 43.934 | 16.685 | −29.083 | 1.00 0.00 |
| ATOM | 145 | HG | LEU | 192 | 44.341 | 16.403 | −31.556 | 1.00 0.00 |

-continued

| HEADER | | | Q9Y463 DYRK1B_HUMAN 4SC Active Site Homology Model | | | | | |
|---|---|---|---|---|---|---|---|---|
| ATOM | 146 | HD11 | LEU | 192 | 43.651 | 18.614 | −32.432 | 1.00 | 0.00 |
| ATOM | 147 | HD12 | LEU | 192 | 44.920 | 19.415 | −31.488 | 1.00 | 0.00 |
| ATOM | 148 | HD13 | LEU | 192 | 45.339 | 18.324 | −32.819 | 1.00 | 0.00 |
| ATOM | 149 | HD21 | LEU | 192 | 46.178 | 16.172 | −29.926 | 1.00 | 0.00 |
| ATOM | 150 | HD22 | LEU | 192 | 46.752 | 16.835 | −31.456 | 1.00 | 0.00 |
| ATOM | 151 | N | LEU | 193 | 41.659 | 16.224 | −31.954 | 1.00 | 0.00 |
| ATOM | 152 | CA | LEU | 193 | 40.998 | 15.164 | −32.703 | 1.00 | 0.00 |
| ATOM | 153 | C | LEU | 193 | 42.001 | 14.686 | −33.774 | 1.00 | 0.00 |
| ATOM | 154 | O | LEU | 193 | 43.192 | 15.009 | −33.761 | 1.00 | 0.00 |
| ATOM | 155 | CB | LEU | 193 | 39.706 | 15.730 | −33.321 | 1.00 | 0.00 |
| ATOM | 156 | CG | LEU | 193 | 38.657 | 16.223 | −32.307 | 1.00 | 0.00 |
| ATOM | 157 | CD1 | LEU | 193 | 37.487 | 16.875 | −33.048 | 1.00 | 0.00 |
| ATOM | 158 | CD2 | LEU | 193 | 38.143 | 15.094 | −31.421 | 1.00 | 0.00 |
| ATOM | 159 | H | LEU | 193 | 42.124 | 16.935 | −32.508 | 1.00 | 0.00 |
| ATOM | 160 | HA | LEU | 193 | 40.791 | 14.312 | −32.048 | 1.00 | 0.00 |
| ATOM | 161 | HB2 | LEU | 193 | 39.976 | 16.566 | −33.980 | 1.00 | 0.00 |
| ATOM | 162 | HB3 | LEU | 193 | 39.226 | 14.988 | −33.963 | 1.00 | 0.00 |
| ATOM | 163 | HG | LEU | 193 | 39.104 | 16.990 | −31.667 | 1.00 | 0.00 |
| ATOM | 164 | HD11 | LEU | 193 | 37.832 | 17.728 | −33.640 | 1.00 | 0.00 |
| ATOM | 165 | HD12 | LEU | 193 | 37.001 | 16.166 | −33.726 | 1.00 | 0.00 |
| ATOM | 166 | HD13 | LEU | 193 | 36.733 | 17.240 | −32.344 | 1.00 | 0.00 |
| ATOM | 167 | HD21 | LEU | 193 | 37.646 | 14.321 | −32.015 | 1.00 | 0.00 |
| ATOM | 168 | HD22 | LEU | 193 | 38.943 | 14.618 | −30.850 | 1.00 | 0.00 |
| ATOM | 169 | HD23 | LEU | 193 | 37.427 | 15.484 | −30.694 | 1.00 | 0.00 |
| ATOM | 170 | N | SER | 194 | 41.465 | 13.813 | −34.705 | 1.00 | 0.00 |
| ATOM | 171 | CA | SER | 194 | 42.273 | 13.215 | −35.777 | 1.00 | 0.00 |
| ATOM | 172 | C | SER | 194 | 42.120 | 14.067 | −37.065 | 1.00 | 0.00 |
| ATOM | 173 | O | SER | 194 | 42.012 | 15.294 | −37.049 | 1.00 | 0.00 |
| ATOM | 174 | CB | SER | 194 | 41.881 | 11.738 | −35.933 | 1.00 | 0.00 |
| ATOM | 175 | OG | SER | 194 | 42.606 | 11.082 | −36.979 | 1.00 | 0.00 |
| ATOM | 176 | H | SER | 194 | 40.464 | 13.574 | −34.716 | 1.00 | 0.00 |
| ATOM | 177 | HA | SER | 194 | 43.337 | 13.271 | −35.515 | 1.00 | 0.00 |
| ATOM | 178 | HB2 | SER | 194 | 40.823 | 11.633 | −36.169 | 1.00 | 0.00 |
| ATOM | 179 | HB3 | SER | 194 | 42.073 | 11.202 | −34.998 | 1.00 | 0.00 |
| ATOM | 180 | HG | SER | 194 | 42.337 | 10.145 | −36.941 | 1.00 | 0.00 |
| ATOM | 181 | N | TYR | 195 | 42.208 | 13.346 | −38.241 | 1.00 | 0.00 |
| ATOM | 182 | CA | TYR | 195 | 42.031 | 13.927 | −39.578 | 1.00 | 0.00 |
| ATOM | 183 | C | TYR | 195 | 40.535 | 14.271 | −39.809 | 1.00 | 0.00 |
| ATOM | 184 | O | TYR | 195 | 39.652 | 14.002 | −38.987 | 1.00 | 0.00 |
| ATOM | 185 | CB | TYR | 195 | 42.506 | 12.940 | −40.664 | 1.00 | 0.00 |
| ATOM | 186 | CG | TYR | 195 | 43.948 | 12.506 | −40.526 | 1.00 | 0.00 |
| ATOM | 187 | CD1 | TYR | 195 | 44.989 | 13.347 | −40.941 | 1.00 | 0.00 |
| ATOM | 188 | CD2 | TYR | 195 | 44.263 | 11.251 | −39.984 | 1.00 | 0.00 |
| ATOM | 189 | CE1 | TYR | 195 | 46.321 | 12.942 | −40.809 | 1.00 | 0.00 |
| ATOM | 190 | CE2 | TYR | 195 | 45.593 | 10.847 | −39.847 | 1.00 | 0.00 |
| ATOM | 191 | CZ | TYR | 195 | 46.614 | 11.698 | −40.260 | 1.00 | 0.00 |
| ATOM | 192 | OH | TYR | 195 | 47.927 | 11.334 | −40.136 | 1.00 | 0.00 |
| ATOM | 193 | H | TYR | 195 | 42.426 | 12.347 | −38.149 | 1.00 | 0.00 |
| ATOM | 194 | HA | TYR | 195 | 42.602 | 14.863 | −39.618 | 1.00 | 0.00 |
| ATOM | 195 | HB2 | TYR | 195 | 41.862 | 12.051 | −40.660 | 1.00 | 0.00 |
| ATOM | 196 | HB3 | TYR | 195 | 42.382 | 13.375 | −41.660 | 1.00 | 0.00 |
| ATOM | 197 | HD1 | TYR | 195 | 44.773 | 14.317 | −41.384 | 1.00 | 0.00 |
| ATOM | 198 | HD2 | TYR | 195 | 43.473 | 10.575 | −39.666 | 1.00 | 0.00 |
| ATOM | 199 | HE1 | TYR | 195 | 47.124 | 13.598 | −41.134 | 1.00 | 0.00 |
| ATOM | 200 | HE2 | TYR | 195 | 45.812 | 9.872 | −39.424 | 1.00 | 0.00 |
| ATOM | 201 | HH | TYR | 195 | 47.956 | 10.506 | −39.633 | 1.00 | 0.00 |
| ATOM | 202 | N | ASN | 196 | 40.248 | 14.910 | −41.011 | 1.00 | 0.00 |
| ATOM | 203 | H | ASN | 196 | 41.003 | 15.135 | −41.681 | 1.00 | 0.00 |
| ATOM | 204 | HB2 | ASN | 196 | 39.211 | 17.345 | −41.043 | 1.00 | 0.00 |
| ATOM | 205 | CB | ASP | 199 | 41.898 | 13.839 | −44.603 | 1.00 | 0.00 |
| ATOM | 206 | CG | ASP | 199 | 42.351 | 15.267 | −44.399 | 1.00 | 0.00 |
| ATOM | 207 | OD2 | ASP | 199 | 42.727 | 15.888 | −45.449 | 1.00 | 0.00 |
| ATOM | 208 | OD1 | ASP | 199 | 42.296 | 15.648 | −43.194 | 1.00 | 0.00 |
| ATOM | 209 | HB1 | ASP | 199 | 42.800 | 13.215 | −44.656 | 1.00 | 0.00 |
| ATOM | 210 | HB2 | ASP | 199 | 41.348 | 13.504 | −43.719 | 1.00 | 0.00 |
| ATOM | 211 | C | GLU | 243 | 35.270 | 20.258 | −42.464 | 1.00 | 0.00 |
| ATOM | 212 | O | GLU | 243 | 36.232 | 20.686 | −41.824 | 1.00 | 0.00 |
| ATOM | 213 | N | ASN | 244 | 33.990 | 20.196 | −41.933 | 1.00 | 0.00 |
| ATOM | 214 | CA | ASN | 244 | 33.636 | 20.686 | −40.580 | 1.00 | 0.00 |
| ATOM | 215 | C | ASN | 244 | 33.293 | 19.525 | −39.609 | 1.00 | 0.00 |
| ATOM | 216 | O | ASN | 244 | 32.827 | 19.694 | −38.480 | 1.00 | 0.00 |
| ATOM | 217 | CB | ASN | 244 | 32.457 | 21.671 | −40.630 | 1.00 | 0.00 |
| ATOM | 218 | CG | ASN | 244 | 32.859 | 23.064 | −41.070 | 1.00 | 0.00 |
| ATOM | 219 | OD1 | ASN | 244 | 34.018 | 23.460 | −41.130 | 1.00 | 0.00 |
| ATOM | 220 | ND2 | ASN | 244 | 31.803 | 23.864 | −41.418 | 1.00 | 0.00 |
| ATOM | 221 | HA | ASN | 244 | 34.519 | 21.170 | −40.147 | 1.00 | 0.00 |
| ATOM | 222 | HB2 | ASN | 244 | 31.999 | 21.785 | −39.640 | 1.00 | 0.00 |

-continued

| HEADER | | Q9Y463 DYRK1B_HUMAN 4SC Active Site Homology Model | | | | | | |
|---|---|---|---|---|---|---|---|---|
| ATOM | 223 | HB3 | ASN | 244 | 31.676 | 21.296 | −41.301 | 1.00 0.00 |
| ATOM | 224 | HD2 | ASN | 244 | 31.914 | 24.813 | −41.766 | 1.00 0.00 |
| ATOM | 225 | CB | LEU | 246 | 37.350 | 16.327 | −36.963 | 1.00 0.00 |
| ATOM | 226 | CG | LEU | 246 | 38.272 | 17.316 | −37.711 | 1.00 0.00 |
| ATOM | 227 | CD1 | LEU | 246 | 37.498 | 18.328 | −38.552 | 1.00 0.00 |
| ATOM | 228 | CD2 | LEU | 246 | 39.171 | 18.051 | −36.716 | 1.00 0.00 |
| ATOM | 229 | HB1 | LEU | 246 | 36.718 | 16.877 | −36.253 | 1.00 0.00 |
| ATOM | 230 | HB2 | LEU | 246 | 37.988 | 15.672 | −36.355 | 1.00 0.00 |
| ATOM | 231 | HG | LEU | 246 | 38.926 | 16.745 | −38.382 | 1.00 0.00 |
| ATOM | 232 | HD11 | LEU | 246 | 37.009 | 17.848 | −39.404 | 1.00 0.00 |
| ATOM | 233 | HD12 | LEU | 246 | 36.730 | 18.825 | −37.956 | 1.00 0.00 |
| ATOM | 234 | HD13 | LEU | 246 | 38.165 | 19.095 | −38.958 | 1.00 0.00 |
| ATOM | 235 | HD21 | LEU | 246 | 38.582 | 18.626 | −35.995 | 1.00 0.00 |
| ATOM | 236 | HD22 | LEU | 246 | 39.794 | 17.341 | −36.163 | 1.00 0.00 |
| ATOM | 237 | HD23 | LEU | 246 | 39.844 | 18.743 | −37.234 | 1.00 0.00 |
| ATOM | 238 | O | LEU | 247 | 38.909 | 12.892 | −35.280 | 1.00 0.00 |
| ATOM | 239 | HB3 | PRO | 250 | 44.367 | 8.740 | −37.457 | 1.00 0.00 |
| ATOM | 240 | N | VAL | 258 | 32.839 | 20.006 | −35.521 | 1.00 0.00 |
| ATOM | 241 | CA | VAL | 258 | 33.562 | 21.186 | −35.053 | 1.00 0.00 |
| ATOM | 242 | C | VAL | 258 | 32.997 | 22.405 | −35.785 | 1.00 0.00 |
| ATOM | 243 | O | VAL | 258 | 32.550 | 22.327 | −36.926 | 1.00 0.00 |
| ATOM | 244 | CB | VAL | 258 | 35.095 | 21.095 | −35.247 | 1.00 0.00 |
| ATOM | 245 | CG1 | VAL | 258 | 35.680 | 19.850 | −34.579 | 1.00 0.00 |
| ATOM | 246 | CG2 | VAL | 258 | 35.535 | 21.135 | −36.713 | 1.00 0.00 |
| ATOM | 247 | H | VAL | 258 | 32.878 | 19.821 | −36.532 | 1.00 0.00 |
| ATOM | 248 | HA | VAL | 258 | 33.351 | 21.310 | −33.986 | 1.00 0.00 |
| ATOM | 249 | HB | VAL | 258 | 35.542 | 21.972 | −34.759 | 1.00 0.00 |
| ATOM | 250 | HG11 | VAL | 258 | 35.404 | 19.812 | −33.524 | 1.00 0.00 |
| ATOM | 251 | HG12 | VAL | 258 | 35.333 | 18.929 | −35.058 | 1.00 0.00 |
| ATOM | 252 | HG13 | VAL | 258 | 36.773 | 19.863 | −34.632 | 1.00 0.00 |
| ATOM | 253 | HG21 | VAL | 258 | 35.104 | 20.307 | −37.280 | 1.00 0.00 |
| ATOM | 254 | HG22 | VAL | 258 | 35.243 | 22.072 | −37.198 | 1.00 0.00 |
| ATOM | 255 | HG23 | VAL | 258 | 36.625 | 21.064 | −36.789 | 1.00 0.00 |
| ATOM | 256 | N | ASP | 259 | 33.076 | 23.590 | −35.084 | 1.00 0.00 |
| ATOM | 257 | CA | ASP | 259 | 32.516 | 24.861 | −35.569 | 1.00 0.00 |
| ATOM | 258 | C | ASP | 259 | 30.973 | 24.771 | −35.585 | 1.00 0.00 |
| ATOM | 259 | O | ASP | 259 | 30.355 | 23.808 | −36.037 | 1.00 0.00 |
| ATOM | 260 | CB | ASP | 259 | 33.035 | 25.335 | −36.928 | 1.00 0.00 |
| ATOM | 261 | CG | ASP | 259 | 32.659 | 26.812 | −37.080 | 1.00 0.00 |
| ATOM | 262 | OD1 | ASP | 259 | 33.553 | 27.633 | −36.694 | 1.00 0.00 |
| ATOM | 263 | OD2 | ASP | 259 | 31.491 | 27.050 | −37.512 | 1.00 0.00 |
| ATOM | 264 | H | ASP | 259 | 33.525 | 23.591 | −34.173 | 1.00 0.00 |
| ATOM | 265 | HA | ASP | 259 | 32.827 | 25.577 | −34.804 | 1.00 0.00 |
| ATOM | 266 | HB2 | ASP | 259 | 32.597 | 24.768 | −37.757 | 1.00 0.00 |
| ATOM | 267 | HB3 | ASP | 259 | 34.123 | 25.221 | −36.990 | 1.00 0.00 |
| ATOM | 268 | N | PHE | 260 | 30.358 | 25.863 | −35.044 | 1.00 0.00 |
| ATOM | 269 | H | PHE | 260 | 30.953 | 26.564 | −34.526 | 1.00 0.00 |
| ATOM | 270 | HD2 | PHE | 260 | 30.099 | 23.791 | −33.004 | 1.00 0.00 |
| ATOM | 271 | H | GLY | 261 | 30.374 | 27.597 | −36.722 | 1.00 0.00 |
| TER | 272 | | GLY | 261 | | | | |
| END | | | | | | | | |

(Residues at positions 190-196 disclosed as SEQ ID NO: 6 and residues at positions 258-261 disclosed as SEQ ID NO: 7)

Table 1 shows the top hits found among a library of commercially available compounds with the above modeling approach, ranked by score/mol. wt. ratio (score/MW). While the ProPose Score is influenced by the size and thus the molecular weight of the tested compounds (because potential molecular interaction partners are more abundant in larger molecules), the score/molecular weight ratio generally represents a reasonable approach for identifying possible lead compounds. To maintain economical balance, Table 1 shows only every fifth hit. The results demonstrate that in terms of structure, a variety of small molecule inhibitors is accepted into the DYRK1B binding site and may be usable in the methods of the present invention. In the above modeling approach compound P has a score/weight ratio of −0.056 with a ProPose score of −15,803, thus showing a rationale for relating the score/weight ratio found in the above modeling approach to actual in vitro and in vivo binding affinity.

TABLE 1

| Rank | Chemical Name | Score/MW | ProPose Score |
|---|---|---|---|
| 1 | coronene | −0.106 | −31.752 |
| 2 | (Z)-3-(5-(2-cyano-2-(2-fluorophenyl)vinyl)furan-2-yl)benzoic acid | −0.094 | −31.269 |
| 3 | 10-(naphthalen-2-yl)-5H-benzo[c]furo[3,2-g]chromen-5-one | −0.090 | −32.709 |
| 4 | (Z)-2-((5-(2-(trifluoromethyl)phenyl)furan-2-yl)methylene)benzo[b]thiophen-3(2H)-one | −0.090 | −33.443 |

TABLE 1-continued

| Rank | Chemical Name | Score/MW | ProPose Score |
|---|---|---|---|
| 5 | 4-phenyl-2-(quinolin-2-yl)-10H-pyrido[2,3-b]carbazole | −0.087 | −36.672 |
| 6 | (E)-3-(5-(2-(benzo[d]thiazol-2-yl)-2-cyanovinyl)furan-2-yl)benzoic acid | −0.087 | −32.212 |
| 7 | perfluorophenyl 3-(thiazol-2-yl)benzoate | −0.085 | −31.555 |
| 8 | 9,10-di(naphthalen-2-yl)anthracene | −0.085 | −36.449 |
| 9 | (Z)-2-(2-chloro-6-fluorobenzylidene)-3-oxo-2,3-dihydrobenzofuran-6-yl 2-fluorobenzoate | −0.084 | −34.682 |
| 10 | (Z)-2-chloro-5-(5-(2-(4-chlorophenyl)-2-cyanovinyl)furan-2-yl)benzoic acid | −0.084 | −32.066 |
| 15 | (Z)-1-(5-((1-oxobenzo[4,5]imidazo[2,1-b]thiazol-2(1H)-ylidene)methyl)furan-2-yl)anthracene-9,10-dione | −0.082 | −38.926 |
| 20 | 2-(5-methylthiophen-2-yl)-N-(perfluorophenyl)quinoline-4-carboxamide | −0.081 | −35.345 |
| 25 | (Z)-5-((1H-indol-3-yl)methylene)-2-thioxo-3-(3-(trifluoromethyl)phenyl)thiazolidin-4-one | −0.080 | −32.481 |
| 30 | (E)-3-(5-((2-(2-(naphthalen-1-yl)acetyl)hydrazono)methyl)furan-2-yl)benzoic acid | −0.080 | −31.672 |
| 35 | 3,4-bis(4-phenoxyphenyl)-2,5-diphenylcyclopenta-2,4-dienone | −0.079 | −45.185 |
| 40 | (Z)-3-(5-((4-oxo-2-thioxo-3-(o-tolyl)thiazolidin-5-ylidene)methyl)furan-2-yl)benzoic acid | −0.079 | −33.269 |
| 45 | (Z)-3-benzyl-5-((5-(naphthalen-1-yl)furan-2-yl)methylene)-2-thioxothiazolidin-4-one | −0.079 | −33.718 |
| 50 | (Z)-5-(naphthalen-2-ylmethylene)-2-thioxo-3-(3-(trifluoromethyl)phenyl)thiazolidin-4-one | −0.079 | −32.674 |
| 55 | 3-(benzofuran-2-carboxamido)-N-(3-chlorophenyl)benzofuran-2-carboxamide | −0.078 | −33.630 |
| 60 | 3-(benzofuran-2-carboxamido)-N-(3-chloro-4-fluorophenyl)benzofuran-2-carboxamide | −0.078 | −34.925 |
| 65 | 1-(4-phenoxyphenyl)-3-(quinolin-2-yl)benzo[f]quinoline | −0.078 | −36.803 |
| 70 | 5-(dibenzo[b,d]thiophen-2-yl)-2-(3-fluorophenyl)-4-phenyl-1H-imidazole | −0.077 | −32.521 |
| 75 | ethyl 5-benzyl-2-(perfluorobenzamido)thiophene-3-carboxylate | −0.077 | −35.151 |
| 80 | N-((8aR,10aR)-9,10-dioxo-8a,9,10,10a-tetrahydroanthracen-1-yl)-9-oxo-9H-fluorene-1-carboxamide | −0.077 | −33.185 |
| 85 | 3-chloro-N-(2-fluoro-3-(trifluoromethyl)benzyl)naphtho[2,1-b]thiophene-2-carboxamide | −0.077 | −33.503 |
| 90 | N-(benzo[d][1,3]dioxol-5-yl)-3-(benzofuran-2-carboxamido)benzofuran-2-carboxamide | −0.076 | −33.626 |
| 95 | (E)-4-(5-((1-methyl-4,6-dioxo-3-phenyl-2-thioxotetrahydropyrimidin-5(2H)-ylidene)methyl)furan-2-yl)benzoic acid | −0.076 | −32.857 |
| 100 | N-(4-(2-oxo-1,2,3,4-tetrahydroquinolin-6-yl)thiazol-2-yl)-3-(trifluoromethyl)benzamide | −0.076 | −31.666 |
| 105 | 5-((4-(benzyloxy)phenyl)amino)-3,8,10-trichloropyrene-1,6-dione | −0.076 | −40.303 |
| 110 | (E)-3-oxo-4-(2-phenyl-1H-cyclopenta[b]chromen-4-ium-1-ylidene)-2-(2-phenylcyclopenta[b]chromen-1-yl)cyclobut-1-enolate | −0.075 | −42.695 |
| 115 | 3-(5-cyano-1-cyclopropyl-6-oxo-1,6-dihydropyridin-3-yl)-N-(3,4-difluorophenyl)-5-fluorobenzofuran-2-carboxamide | −0.075 | −33.773 |
| 120 | 2-((benzo[d]thiazol-2-ylmethyl)thio)-3-(2-fluorophenyl)quinazolin-4(3H)-one | −0.075 | −31.411 |
| 125 | (2Z,2'Z)-3,3'-(1,2-phenylene)bis(2-(naphthalen-1-yl)acrylonitrile) | −0.075 | −32.310 |
| 130 | (E)-4-(5-((4-hydroxy-6-oxo-2-thioxo-1-(p-tolyl)-1,6-dihydropyrimidin-5(2H)-ylidene)methyl)furan-2-yl)benzoic acid | −0.075 | −32.134 |
| 135 | 3-(5-((Z)-((Z)-2-((2,5-dimethylphenyl)imino)-4-oxothiazolidin-5-ylidene)methyl)furan-2-yl)benzoic acid | −0.074 | −31.093 |
| 140 | N-(5,7-difluorobenzo[d]thiazol-2-yl)-N-(furan-2-ylmethyl)benzo[d]thiazole-5-carboxamide | −0.074 | −31.756 |
| 145 | 5-(dibenzo[b,d]thiophen-2-yl)-2-(3-fluorophenyl)-4-phenyl-1H-imidazole | −0.074 | −31.170 |
| 150 | (E)-1-(((2-(2-benzylphenoxy)-5-(trifluoromethyl)phenyl)imino)methyl)naphthalen-2-ol | −0.074 | −36.731 |
| 155 | 2-((1-oxo-2-phenyl-2,9-dihydro-1H-pyrimido[5,4-b]indol-3-yl)thio)-N-(3-(trifluoromethyl)phenyl)acetamide | −0.074 | −36.536 |
| 160 | (E)-2-cyano-3-(5-(3-nitrophenyl)thiophen-2-yl)-N-(2-(trifluoromethyl)phenyl)acrylamide | −0.074 | −32.697 |
| 165 | 4-(4-(5-(3-(trifluoromethyl)phenyl)furan-2-carboxamido)benzyl)pyridin-1-ium | −0.074 | −31.169 |
| 170 | (E)-3-(4-chlorophenyl)-5-((5-(4-fluorophenyl)furan-2-yl)methylene)-6-hydroxy-2-thioxo-2,3-dihydropyrimidin-4(5H)-one | −0.073 | −31.279 |
| 175 | 3-(naphthalen-2-yloxy)-4-oxo-2-(trifluoromethyl)-4H-chromen-7-yl 4-fluorobenzoate | −0.073 | −36.296 |
| 180 | (E)-2-(4-([1,1'-biphenyl]-4-yl)thiazol-2-yl)-3-(2-chloro-7-methoxyquinolin-3-yl)acrylonitrile | −0.073 | −35.173 |
| 185 | (Z)-3-cyano-N-(3-((2-fluorophenyl)carbamoyl)-2H-chromen-2-ylidene)-4,5,6,7-tetrahydrobenzo[b]thiophen-2-aminium | −0.073 | −32.518 |
| 190 | 2,3,4,5,6-pentafluoro-N-(3-(2-oxo-2H-chromen-3-yl)phenyl)benzamide | −0.073 | −31.519 |
| 195 | (E)-3-(5-(3,4-dichlorophenyl)furan-2-yl)-N-(2-(trifluoromethyl)phenyl)acrylamide | −0.073 | −31.127 |
| 200 | (E)-3-(5-(((3-cyano-4,5-bis(4-methoxyphenyl)furan-2-yl)imino)methyl)furan-2-yl)benzoic acid | −0.073 | −37.734 |
| 205 | 2-(5-(4-chloro-3-(trifluoromethyl)phenyl)furan-2-yl)-6-fluoroquinoline-4-carboxylic acid | −0.073 | −31.670 |

TABLE 1-continued

| Rank | Chemical Name | Score/ MW | ProPose Score |
|---|---|---|---|
| 210 | (Z)-2-((Z)-5-((5-(2-chlorophenyl)furan-2-yl)methylene)-4-oxo-3-phenylthiazolidin-2-ylidene)-2-cyano-N-(furan-2-ylmethyl)acetamide | −0.073 | −38.373 |
| 215 | 2-(((1-(difluoromethyl)-1H-benzo[d]imidazol-2-yl)methyl)thio)-3-(2,4-difluorophenyl)quinazolin-4(3H)-one | −0.073 | −34.160 |
| 220 | N-(3-fluorophenyl)-2-((1-oxo-2-phenyl-1,2-dihydrobenzofuro[3,2-d]pyrimidin-3-yl)thio)acetamide | −0.073 | −32.311 |
| 225 | N-(2-fluorophenyl)-2-((1-oxo-2-phenyl-1,2-dihydrobenzofuro[3,2-d]pyrimidin-3-yl)thio)acetamide | −0.072 | −32.284 |
| 230 | 3-([1,1'-biphenyl]-4-yloxy)-4-oxo-2-(trifluoromethyl)-4H-chromen-7-yl 3-chlorobenzoate | −0.072 | −38.834 |
| 235 | 3-([1,1'-biphenyl]-4-yloxy)-7-((2-chlorobenzyl)oxy)-2-(trifluoromethyl)-4H-chromen-4-one | −0.072 | −37.777 |
| 240 | (E)-3-(naphthalen-1-yl)-2-(4-(3-oxo-3H-benzo[f]chromen-2-yl)thiazol-2-yl)acrylonitrile | −0.072 | −32.964 |
| 245 | (R) - N-(3-(3-(2,5-difluorophenyl)-4-oxothiazolidin-2-yl)phenyl)-2-naphthamide | −0.072 | −33.182 |
| 250 | (Z)-2-(2-chloro-6-fluorobenzylidene)-3-oxo-2,3-dihydrobenzofuran-6-yl 2-bromobenzoate | −0.072 | −34.043 |
| 255 | (E)-2-(4-(4-chlorophenyl)thiazol-2-yl)-3-(5-(3-nitrophenyl)furan-2-yl)acrylonitrile | −0.072 | −31.136 |
| 260 | 2-(3-chlorophenyl)-5-(dibenzo[b,d]thiophen-2-yl)-4-phenyl-1H-imidazole | −0.072 | −31.298 |
| 265 | 2-(((6-chloroimidazo[1,2-a]pyridin-2-yl)methyl)thio)-3-(2,4-difluorophenyl)quinazolin-4(3H)-one | −0.072 | −32.567 |
| 270 | 2-((1-oxo-2-phenyl-1,2-dihydrobenzofuro[3,2-d]pyrimidin-3-yl)thio)-N-(p-tolyl)acetamide | −0.072 | −31.571 |
| 275 | 2-([1,1'-biphenyl]-4-yl)-N-(3-(trifluoromethyl)phenyl)quinoline-4-carboxamide | −0.071 | −33.456 |
| 280 | (E)-4-(5-((1-(3,5-dimethylphenyl)-4-hydroxy-6-oxo-2-thioxo-1,6-dihydropyrimidin-5(2H)-ylidene)methyl)furan-2-yl)benzoic acid | −0.071 | −31.719 |
| 285 | 3-(benzofuran-2-carboxamido)-N-(2,3-dihydrobenzo[b][1,4]dioxin-6-yl)benzofuran-2-carboxamide | −0.071 | −32.403 |
| 290 | N-(3-(3H-benzo[d]imidazol-2-yl)-4-chlorophenyl)-2,3,4,5,6-pentafluorobenzamide | −0.071 | −31.194 |
| 295 | 2-((3-((Z)-((Z)-4-oxo-3-phenyl-2-(phenylimino)thiazolidin-5-ylidene)methyl)-1H-indol-1-yl)methyl)benzonitrile | −0.071 | −36.350 |
| 300 | 3-((2-(indolin-1-yl)-2-oxoethyl)thio)-2-(3-(trifluoromethyl)phenyl)-2,9-dihydro-1H-pyrimido[5,4-b]indol-1-one | −0.071 | −37.022 |
| 305 | (Z)-3-(2-((3-(2-((4-fluorophenyl)amino)-2-oxoethyl)-2,4-dioxothiazolidin-5-ylidene)methyl)-1H-pyrrol-1-yl)benzoic acid | −0.071 | −33.008 |
| 310 | (1Z,2E)-2-cyano-3-(5-(3-nitrophenyl)thiophen-2-yl)-N-(2-(trifluoromethyl)phenyl)acrylimidate | −0.071 | −31.408 |
| 315 | N-(2,4-difluorophenyl)-2-((2-(4-fluorophenyl)-1-oxo-2,9-dihydro-1H-pyrimido[5,4-b]indol-3-yl)thio)acetamide | −0.071 | −34.057 |
| 320 | 3-((2-fluorobenzyl)thio)-2,6-diphenylthieno[2,3-d]pyrimidin-1(2H)-one | −0.071 | −31.474 |
| 325 | 3-((2-(3,4-difluorophenyl)-2-oxoethyl)thio)-7-(furan-2-yl)-2-phenylthieno[2,3-d]pyrimidin-1(2H)-one | −0.071 | −33.993 |
| 330 | (R)-2-(naphthalen-1-yl)-14-phenyl-14H-benzo[5,6]chromeno[3,2-e][1,2,4]triazolo[1,5-c]pyrimidine | −0.071 | −33.675 |
| 335 | (Z)-2-benzyl-6-((5-(3-(trifluoromethyl)phenyl)furan-2-yl)methylene)-3H-thiazolo[3,2-b][1,2,4]triazine-3,7(6H)-dione | −0.071 | −33.992 |
| 340 | 2-((3-(2,4-difluorophenyl)-4-oxo-3,4-dihydroquinazolin-2-yl)thio)-N-(naphthalen-1-yl)acetamide | −0.071 | −33.406 |
| 345 | 3-((4-fluorobenzyl)thio)-2,6-diphenylthieno[2,3-d]pyrimidin-1(2H)-one | −0.071 | −31.342 |
| 350 | 3-((2-oxo-2-phenylethyl)thio)-2,6-diphenylthieno[2,3-d]pyrimidin-1(2H)-one | −0.070 | −31.985 |
| 355 | N-(2-benzoyl-4-chlorophenyl)-2-((4-phenylquinazolin-2-yl)thio)acetamide | −0.070 | −35.849 |
| 360 | (Z)-3-benzyl-5-((5-(2,4-dichlorophenyl)furan-2-yl)methylene)-2-thioxothiazolidin-4-one | −0.070 | −31.356 |
| 365 | (1-amino-5,7-bis(4-methoxyphenyl)thieno[2,3-b]pyridin-2-yl)(naphthalen-2-yl)methanone | −0.070 | −36.259 |
| 370 | (Z)-2-((4-chlorobenzyl)thio)-1-(4-chlorophenyl)-4-(4-fluorobenzylidene)-1H-imidazol-5(4H)-one | −0.070 | −32.080 |
| 375 | (Z) - N-(3-(1H-benzo[d]imidazol-2-yl)-6,8-dichloro-2H-chromen-2-ylidene)-[1,1'-biphenyl]-4-aminium | −0.070 | −33.879 |
| 380 | N-(2-chloro-5-(6-methylbenzo[d]oxazol-2-yl)phenyl)-2,3,4,5,6-pentafluorobenzamide | −0.070 | −31.710 |
| 385 | (E) - N-(2-(2-chloro-4,5-difluorophenyl)benzo[d]oxazol-5-yl)-3-(4-chlorophenyl)acrylamide | −0.070 | −31.164 |
| 390 | N-(4-chloro-2-(2-chlorobenzoyl)phenyl)-5-(thiophen-2-yl)-7-(trifluoromethyl)pyrazolo[1,5-a]pyrimidine-2-carboxamide | −0.070 | −39.252 |
| 395 | 3-(2,4-difluorophenyl)-2-((2-(indolin-1-yl)-2-oxoethyl)thio)quinazolin-4(3H)-one | −0.070 | −31.389 |
| 400 | (Z)-2-benzyl-5-((5-(3-(trifluoromethyl)phenyl)furan-2-yl)methylene)thiazolo[3,2-b][1,2,4]triazol-6(5H)-one | −0.070 | −31.635 |
| 405 | 2-(4-(benzyloxy)phenyl)-5-(dibenzo[b,d]thiophen-2-yl)-4-phenyl-1H-imidazole | −0.070 | −35.456 |
| 410 | (4-(2-([1,1'-biphenyl]-4-yl)-5-phenyl-1H-imidazol-4-yl)phenyl)(phenyl)methanone | −0.070 | −33.183 |

TABLE 1-continued

| Rank | Chemical Name | Score/ MW | ProPose Score |
|---|---|---|---|
| 415 | (2-amino-1-(4-(4-nitrophenyl)thiazol-2-yl)indolizin-3-yl)(4-fluorophenyl)methanone | −0.070 | −31.910 |
| 420 | 3-(naphthalen-2-yloxy)-4-oxo-2-(trifluoromethyl)-4H-chromen-7-yl 2-methoxybenzoate | −0.070 | −35.216 |
| 425 | (Z)-4-chloro-3-(5-((3-(2-chloro-6-fluorobenzyl)-2,4-dioxothiazolidin-5-ylidene)methyl)furan-2-yl)benzoic acid | −0.069 | −34.113 |
| 430 | 2,2'-((4-methoxyphenyl)methylene)bis(1H-phenalene-1,3(2H)-dione) | −0.069 | −35.421 |
| 435 | N,N'-(1,2-phenylene)bis(5-(4-fluorophenyl)furan-2-carboxamide) | −0.069 | −33.557 |
| 440 | 3-(benzofuran-2-carboxamido)-N-(2,4-dimethoxyphenyl)benzofuran-2-carboxamide | −0.069 | −31.582 |
| 445 | (E)-3-(3-(2-((1-naphthoyl)oxy)phenyl)-2-cyanoacrylamido)benzoic acid | −0.069 | −31.906 |
| 450 | 2-(4-fluorophenyl)-3-((2-(indolin-1-yl)-2-oxoethyl)thio)-2,9-dihydro-1H-pyrimido[5,4-b]indol-1-one | −0.069 | −32.460 |
| 455 | 2-chloro-4-(5-((Z)-((Z)-3-(2-methoxyethyl)-4-oxo-2-(phenylimino)thiazolidin-5-ylidene)methyl)furan-2-yl)benzoic acid | −0.069 | −33.229 |
| 460 | 2-((3-(4-ethoxyphenyl)-4-oxo-3,4-dihydroquinazolin-2-yl)thio)-N-(3-(trifluoromethyl)phenyl)acetamide | −0.069 | −34.421 |
| 465 | (Z)-3-((2-chloro-5-(trifluoromethyl)phenyl)amino)-2-(4-(2-oxo-2H-chromen-3-yl)thiazol-2-yl)acrylonitrile | −0.069 | −32.616 |
| 470 | N-(9,10-dioxo-9,10-dihydroanthracen-1-yl)-2-((4-(4-fluorophenyl)-1H-imidazol-2-yl)thio)acetamide | −0.069 | −31.454 |
| 475 | N-(5-chloro-2-fluorophenyl)-2-((3-(2-chlorophenyl)-4-oxo-3,4-dihydroquinazolin-2-yl)thio)acetamide | −0.069 | −32.553 |
| 480 | 3-((2-(4-fluorophenyl)-2-oxoethyl)thio)-10-oxo-11-phenethyl-6,7,8,9,10.11-hexahydrobenzo[4,5]thieno[3,2-e][1,2,4]triazolo[4,3-a]pyrimidin-2-ium | −0.069 | −35.633 |
| 485 | (Z)-5-(5-chloro-2-((2-fluorobenzyl)oxy)benzylidene)-3-(3-fluorophenyl)-2-thioxothiazolidin-4-one | −0.068 | −32.466 |
| 490 | 2-((2-(4-chlorophenyl)-1-oxo-2,9-dihydro-1H-pyrimido[5,4-b]indol-3-yl)thio)-N-(2,4-difluorophenyl)acetamide | −0.068 | −33.999 |
| 495 | (Z)-2-(4-bromobenzoyl)-8-(furan-2-yl)-5-(furan-2-ylmethylene)-6,7-dihydro-5H-cyclopenta[b]thieno[3,2-e]pyridine-1-carbonitrile | −0.068 | −36.022 |
| 500 | (R)-2-((((9H-fluoren-9-yl)methoxy)carbonyl)amino)-3-(perfluorophenyl)propanoic acid | −0.068 | −32.509 |
| 505 | 10-(2-chloro-4-fluorobenzyl)-N-(3-(3,4-dihydroisoquinolin-2(1H)-yl)propyl)-11-oxo-10.11-dihydrodibenzo[b,f][1,4]thiazepine-8-carboxamide | −0.068 | −40.007 |
| 510 | N-(3,4-difluorophenyl)-2-((3-(2,4-difluorophenyl)-4-oxo-3,4-dihydroquinazolin-2-yl)thio)acetamide | −0.068 | −31.281 |
| 515 | N2,N5-bis(1,2-dihydroacenaphthylen-6-yl)thiophene-2,5-dicarboxamide | −0.068 | −32.291 |
| 520 | (2Z,5Z)-5-((5-(2-bromo-4-methylphenyl)furan-2-yl)methylene)-3-(furan-2-ylmethyl)-2-(phenylimino)thiazolidin-4-one | −0.068 | −35.336 |
| 525 | 3-(2-((2-fluorobenzyl)thio)-5-(phenylthio)pyrimidine-4-carboxamido)benzoic acid | −0.068 | −33.343 |
| 530 | (E)-4-(4-(diphenylamino)benzylidene)-1,2,3,4-tetrahydroacridin-10-ium-9-carboxylate | −0.068 | −32.777 |
| 535 | N-(3,4-dichlorophenyl)-2-((1-oxo-2-phenyl-2,9-dihydro-1H-pyrimido[5,4-b]indol-3-yl)thio)acetamide | −0.068 | −33.627 |
| 540 | N-(2-chloro-5-(4,6-dimethylbenzo[d]oxazol-2-yl)phenyl)-2,3,4,5,6-pentafluorobenzamide | −0.068 | −31.675 |
| 545 | N-(2-ethylphenyl)-2-((1-oxo-2-(p-tolyl)-1,2-dihydrobenzofuro[3,2-d]pyrimidin-3-yl)thio)acetamide | −0.068 | −31.851 |
| 550 | 4-(5-((Z)-((Z)-3-(2-(1H-indol-3-yl)ethyl)-2-((4-methoxyphenyl)imino)-4-oxothiazolidin-5-ylidene)methyl)furan-2-yl)benzonitrile | −0.068 | −36.900 |
| 555 | N-(2-(phenylcarbamoyl)benzofuran-3-yl)-9H-xanthene-9-carboxamide | −0.068 | −31.185 |
| 560 | 9-(phenethylthio)-8-(m-tolyl)-5,6-dihydronaphtho[2',1':4,5]thieno[2,3-d]pyrimidin-7(8H)-one | −0.068 | −32.533 |
| 565 | N-(4-fluorobenzyl)-2-((2-(4-fluorophenyl)-1-oxo-2,9-dihydro-1H-pyrimido[5,4-b]indol-3-yl)thio)acetamide | −0.068 | −32.216 |
| 570 | (Z)-2-cyano-2-((Z)-5-((5-(2-nitrophenyl)furan-2-yl)methylene)-4-oxo-3-phenylthiazolidin-2-ylidene)-N-phenylacetamide | −0.068 | −36.119 |
| 575 | 2-(3-chloro-4-((2-fluorobenzyl)oxy)-5-methoxyphenyl)-5,6,7,8-tetrahydrobenzo[4,5]thieno[2,3-d]pyrimidin-4(3H)-one | −0.068 | −31.810 |
| 580 | (R)-ethyl 2-(perfluorobenzamido)-6-phenyl-4,5,6,7-tetrahydrobenzo[b]thiophene-3-carboxylate | −0.067 | −33.434 |
| 585 | 2-phenyl-5-(m-tolylamino)-3-(p-tolylthio)-1H-naphtho[2,3-g]indole-6,11-dione | −0.067 | −37.131 |
| 590 | (Z)-4-(5-((4-oxo-2-thioxo-3-(3-(trifluoromethyl)phenyl)thiazolidin-5-ylidene)methyl)furan-2-yl)benzoic acid | −0.067 | −31.977 |
| 595 | 2-((2,6-diphenyl-4H-pyran-4-ylidene)methyl)-4,6-diphenylthiopyrylium | −0.067 | −33.244 |
| 600 | 3-([1,1'-biphenyl]-4-yloxy)-7-((2,3,6-trichlorobenzyl)oxy)-2-(trifluoromethyl)-4H-chromen-4-one | −0.067 | −39.843 |
| 605 | N-(3-fluorophenyl)-2-((4-oxo-3-(4-phenoxyphenyl)-3,4-dihydroquinazolin-2-yl)thio)acetamide | −0.067 | −33.445 |
| 610 | N-(3,4-difluorophenyl)-3-(2,2-diphenylacetamido)benzofuran-2-carboxamide | −0.067 | −32.403 |
| 615 | 2-(5-(2-chlorophenyl)furan-2-yl)-N-(4-(trifluoromethyl)phenyl)quinoline-4-carboxamide | −0.067 | −33.082 |

TABLE 1-continued

| Rank | Chemical Name | Score/MW | ProPose Score |
|---|---|---|---|
| 620 | 6-(4-((4-fluorobenzyl)oxy)phenyl)-2-((4-fluorobenzyl)thio)-4-(trifluoromethyl)nicotinonitrile | −0.067 | −34.367 |
| 625 | (Z)-3-(5-((3-(3,4-dichlorophenyl)-4-oxo-2-thioxothiazolidin-5-ylidene)methyl)furan-2-yl)benzoic acid | −0.067 | −31.848 |
| 630 | 5-(3-nitrophenyl)-N-((2-(pyridin-4-yl)benzo[d]oxazol-6-yl)carbamothioyl)furan-2-carboxamide | −0.067 | −32.493 |
| 635 | 4-(((3-(2-chloro-5-(trifluoromethyl)phenyl)-4-oxo-3,4-dihydroquinazolin-2-yl)thio)methyl)benzonitrile | −0.067 | −31.554 |
| 640 | (E)-5-((5-(3-nitrophenyl)furan-2-yl)methylene)-2-thioxo-3-(3-(trifluoromethyl)phenyl)thiazolidin-4-one | −0.067 | −31.821 |
| 645 | (E)-3-(5-(3-nitrophenyl)furan-2-yl)-2-(4-(2-oxo-2H-chromen-3-yl)thiazol-2-yl)acrylonitrile | −0.067 | −31.196 |
| 650 | N-(4-bromo-2-(2-fluorobenzoyl)phenyl)-5-(thiophen-2-yl)-7-(trifluoromethyl)pyrazolo[1,5-a]pyrimidine-2-carboxamide | −0.067 | −39.313 |
| 655 | (E)-3-(5-((3-(2-chloro-6-fluorobenzyl)-2,4-dioxothiazolidin-5-ylidene)methyl)furan-2-yl)-4-methylbenzoic acid | −0.067 | −31.375 |
| 660 | (E)-3-((3-((2-((4-fluorophenyl)amino)-4-oxothiazol-5(4H)-ylidene)methyl)-1H-indol-1-yl)methyl)benzoic acid | −0.067 | −31.323 |
| 665 | (Z)-5-(3-(benzyloxy)benzylidene)-2-thioxo-3-(3-(trifluoromethyl)phenyl)thiazolidin-4-one | −0.067 | −31.372 |
| 670 | (carbonylbis(4,1-phenylene))bis((1,2-dihydroacenaphthylen-6-yl)methanone) | −0.066 | −36.082 |
| 675 | (3R,3aR,6aS)-5-(4-chlorophenyl)-3-(naphthalen-1-yl)-3,3a-dihydrospiro[furo[3,4-c]pyrrole-1,2'-indene]-1',3',4,6(5H,6aH)-tetraone | −0.066 | −33.759 |
| 680 | 3-(2-chloro-5-(trifluoromethyl)phenyl)-4-oxo-N-(4-phenoxyphenyl)-2-thioxo-1,2,3,4-tetrahydroquinazoline-7-carboxamide | −0.066 | −37.711 |
| 685 | N-(3-chloro-4-fluorophenyl)-2-((2-(4-fluorophenyl)-1-oxo-1,2-dihydrobenzofuro[3,2-d]pyrimidin-3-yl)thio)acetamide | −0.066 | −33.052 |
| 690 | 3-((2-(naphthalen-2-yl)-2-oxoethyl)thio)-2,6-diphenylthieno[2,3-d]pyrimidin-1(2H)-one | −0.066 | −33.487 |
| 695 | (Z)-4-(5-((1-(4-bromophenyl)-2-hydroxy-4,6-dioxo-1,6-dihydropyrimidin-5(4H)-ylidene)methyl)furan-2-yl)benzoic acid | −0.066 | −31.789 |
| 700 | (R) - N-(3,4-difluorophenyl)-2-(5-(2-(trifluoromethyl)phenyl)benzo[d]oxazol-2-yl)pyrrolidine-1-carboxamide | −0.066 | −32.317 |
| 705 | (R)-2-((3-(2,4-difluorophenyl)-4-oxo-3,4-dihydroquinazolin-2-yl)thio)-N-(1-(4-fluorophenyl)ethyl)acetamide | −0.066 | −31.111 |
| 710 | 5-(4-((2-chlorobenzyl)oxy)benzylidene)-1,3-diphenyl-2-thioxodihydropyrimidine-4,6(1H,5H)-dione | −0.066 | −34.781 |
| 715 | 3-(2-(6-methylbenzofuran-3-yl)acetamido)-N-(3-(trifluoromethyl)phenyl)benzofuran-2-carboxamide | −0.066 | −32.612 |
| 720 | (Z)-4-chloro-3-(5-((3-(2-((2,3-dihydrobenzo[b][1,4]dioxin-7-yl)amino)-2-oxoethyl)-2,4-dioxothiazolidin-5-ylidene)methyl)furan-2-yl)benzoic acid | −0.066 | −35.710 |
| 725 | N-(2-fluorophenyl)-2-((4-oxo-3-(4-phenoxyphenyl)-3,4-dihydroquinazolin-2-yl)thio)acetamide | −0.066 | −32.875 |
| 730 | 1,4-bis(2-(4-fluorophenyl)-4-phenyl-1H-imidazol-5-yl)benzene | −0.066 | −36.371 |
| 735 | N-(3-cyano-5,6,7,8-tetrahydro-4H-cyclohepta[b]thiophen-2-yl)-5-(furan-2-yl)-1-phenylisoxazolo[5,4-b]pyridine-7-carboxamide | −0.066 | −31.735 |
| 740 | N-(3-(6-(2,3-dihydrobenzo[b][1,4]dioxin-7-yl)pyridin-2-yl)phenyl)-2,3,4,5,6-pentafluorobenzamide | −0.066 | −32.883 |
| 745 | (2Z,5Z)-2-((4-chloro-3-(trifluoromethyl)phenyl)imino)-5-(4-((2-chlorobenzyl)oxy)benzylidene)thiazolidin-4-one | −0.066 | −34.516 |
| 750 | 2-((E)-((4-(2-(4-((E)-(2-hydroxybenzylidene)amino)phenyl)quinazolin-4-yl)phenyl)imino)methyl)phenolate | −0.066 | −34.256 |
| 755 | (Z)-5-((5-(3-nitrophenyl)furan-2-yl)methylene)-2-thioxo-3-(3-(trifluoromethyl)phenyl)thiazolidin-4-one | −0.066 | −31.396 |
| 760 | (S) - N-(1-cyano-5-methyl-4,5,6,7-tetrahydrobenzo[b]thiophen-2-yl)-5-(furan-2-yl)-1-phenylisoxazolo[5,4-b]pyridine-7-carboxamide | −0.066 | −31.639 |
| 765 | N-(3-chloro-4-fluorophenyl)-3-(3-(trifluoromethyl)benzamido)benzofuran-2-carboxamide | −0.066 | −31.368 |
| 770 | (2Z,5Z)-5-(4-((2-chlorobenzyl)oxy)-3-ethoxybenzylidene)-2-((2-fluorophenyl)imino)thiazolidin-4-one | −0.066 | −31.753 |
| 775 | N-(3,5-dimethylphenyl)-2-((2-(4-fluorophenyl)-1-oxo-1,2-dihydrobenzofuro[3,2-d]pyrimidin-3-yl)thio)acetamide | −0.066 | −31.104 |
| 780 | 2-((3-(2,4-difluorophenyl)-4-oxo-3,4-dihydroquinazolin-2-yl)thio)-N-(2-(2-methoxyphenoxy)ethyl)acetamide | −0.066 | −32.650 |
| 785 | (Z)-5-((5-(2-chloro-5-nitrophenyl)furan-2-yl)methylene)-2-thioxo-3-(3-(trifluoromethyl)phenyl)thiazolidin-4-one | −0.066 | −33.525 |
| 790 | 6-chloro-N-(4-chlorophenyl)-2-(5-(3-(trifluoromethyl)phenyl)furan-2-yl)imidazo[1,2-a]pyridin-1-amine | −0.066 | −32.094 |
| 795 | N-(naphthalen-1-yl)-2-((4-oxo-3-phenyl-3,4,6,7,8,9-hexahydropyrimido[4,5-b]quinolin-2-yl)thio)acetamide | −0.066 | −32.283 |
| 800 | 2-((3-(4-(difluoromethoxy)phenyl)-4-oxo-3,4-dihydroquinazolin-2-yl)thio)-N-(2,4-difluorophenyl)acetamide | −0.065 | −32.036 |
| 805 | 2-(3-bromophenyl)-N-(perfluorophenyl)quinoline-4-carboxamide | −0.065 | −32.279 |
| 810 | 2-((E)-((4-(4-((E)-(2-hydroxybenzylidene)amino)phenyl)quinazolin-2-yl)phenyl)imino)methyl)phenolate | −0.065 | −33.986 |

TABLE 1-continued

| Rank | Chemical Name | Score/MW | ProPose Score |
|---|---|---|---|
| 815 | N-([1,1'-biphenyl]-2-yl)-2-((3-(2,4-difluorophenyl)-4-oxo-3,4-dihydroquinazolin-2-yl)thio)acetamide | −0.065 | −32.659 |
| 820 | (3-(9-chloro-5H-chromeno[4,3-b]pyridin-2-yl)-5-methylbenzofuran-2-yl)(4-chlorophenyl)methanone | −0.065 | −31.746 |
| 825 | 3-(2-([1,1'-biphenyl]-4-yl)acetamido)-N-(3,4-difluorophenyl)benzofuran-2-carboxamide | −0.065 | −31.476 |
| 830 | (Z)-5-((5-(4-chloro-3-(trifluoromethyl)phenyl)furan-2-yl)methylene)-3-(2-oxo-2-phenylethyl)thiazolidine-2,4-dione | −0.065 | −32.069 |
| 835 | (Z)-ethyl 2-(4-(((2,6-difluorophenyl)amino)methylene)-1,3-dioxo-3,4-dihydroisoquinolin-2(1H)-yl)-4,5,6,7-tetrahydrobenzo[b]thiophene-3-carboxylate | −0.065 | −33.131 |
| 840 | N-(2-((3,4-difluorophenyl)carbamoyl)benzofuran-3-yl)-9H-xanthene-9-carboxamide | −0.065 | −32.329 |
| 845 | 8-benzyl-9-(phenethylthio)-5,6-dihydronaphtho[2',1':4,5]thieno[2,3-d]pyrimidin-7(8H)-one | −0.065 | −31.280 |
| 850 | 2-((E)-3-((E)-(3-((Z)-2-(quinolin-2-yl)vinyl)phenyl)diazenyl)styryl)quinolin-1-ium | −0.065 | −31.838 |
| 855 | N-(9,10-dioxo-9,10-dihydroanthracen-2-yl)-3-(indolin-1-ylsulfonyl)benzamide | −0.065 | −33.023 |
| 860 | (R,Z)-7-(4-chlorophenyl)-10-((5-(3-(trifluoromethyl)phenyl)furan-2-yl)methylene)-7,10-dihydro-5H-benzo[h]thiazolo[2,3-b]quinazolin-9(6H)-one | −0.065 | −38.232 |
| 865 | N-(2-ethoxyphenyl)-2-((2-(4-fluorophenyl)-1-oxo-2,9-dihydro-1H-pyrimido[5,4-b]indol-3-yl)thio)acetamide | −0.065 | −31.687 |
| 870 | methyl 2-(5-(furan-2-yl)-7-(trifluoromethyl)pyrazolo[1,5-a]pyrimidine-2-carboxamido)-4,5,6,7-tetrahydrobenzo[b]thiophene-1-carboxylate | −0.065 | −31.799 |
| 875 | (2Z,5E)-2-((2-chloro-5-(trifluoromethyl)phenyl)imino)-5-((5-(3-nitrophenyl)furan-2-yl)methylene)thiazolidin-4-one | −0.065 | −32.009 |
| 880 | (Z)-3-(2-((3-(2-((4-chlorophenyl)amino)-2-oxoethyl)-2,4-dioxothiazolidin-5-ylidene)methyl)-1H-pyrrol-1-yl)benzoic acid | −0.065 | −31.154 |
| 885 | (Z)-2-((3-(2-oxo-2H-chromen-3-yl)-1-phenyl-1H-pyrazol-4-yl)methylene)benzo[4,5]imidazo[2,1-b]thiazol-3(2H)-one | −0.065 | −31.635 |
| 890 | N-(3-chloro-4-fluorophenyl)-4-oxo-2-thioxo-3-(3-(trifluoromethyl)phenyl)-1,2,3,4-tetrahydroquinazoline-7-carboxamide | −0.065 | −31.960 |
| 895 | 6-(4-((2,6-dichlorobenzyl)oxy)phenyl)-3-methyl-1-phenyl-4-(trifluoromethyl)-1H-pyrazolo[3,4-b]pyridine | −0.065 | −34.175 |
| 900 | N-(4-chloro-3-(trifluoromethyl)phenyl)-7-(chlorodifluoromethyl)-5-(thiophen-2-yl)pyrazolo[1,5-a]pyrimidine-2-carboxamide | −0.065 | −32.799 |
| 905 | 2-((2-([1,1'-biphenyl]-4-yl)-2-oxoethyl)thio)-4-(4-fluorophenyl)-6-phenylnicotinonitrile | −0.065 | −32.349 |
| 910 | (Z)-2-(4-oxo-2-thioxo-5-(2-(trifluoromethyl)benzylidene)thiazolidin-3-yl)-1H-benzo[de]isoquinoline-1,3(2H)-dione | −0.065 | −31.287 |
| 915 | 2-((2-(4-ethoxyphenyl)-1-oxo-2,9-dihydro-1H-pyrimido[5,4-b]indol-3-yl)thio)-N-(3-fluorophenyl)acetamide | −0.065 | −31.521 |
| 920 | 4-((1-oxo-3-((2-(trifluoromethyl)benzyl)thio)-6,7,8,9-tetrahydrobenzo[4,5]thieno[2,3-d]pyrimidin-2(1H)-yl)methyl)pyridin-1-ium | −0.064 | −31.500 |
| 925 | 2-((2-(4-fluorobenzyl)-1-oxo-1,2-dihydrobenzofuro[3,2-d]pyrimidin-3-yl)thio)-N-(3-methoxyphenyl)acetamide | −0.064 | −31.525 |
| 930 | (R)-2-((1-oxo-2-(3-(trifluoromethyl)phenyl)-2,9-dihydro-1H-pyrimido[5,4-b]indol-3-yl)thio)-N-((tetrahydrofuran-2-yl)methyl)acetamide | −0.064 | −32.335 |
| 935 | (Z)-2-((6-((5-chloro-2-hydroxybenzylidene)amino)benzo[d]thiazol-2-yl)thio)-N-(dibenzo[b,d]furan-3-yl)acetamide | −0.064 | −34.921 |
| 940 | 6-chloro-3-(2,4-difluorophenyl)-2-((2-(3,4-dihydroisoquinolin-2(1H)-yl)-2-oxoethyl)thio)quinazolin-4(3H)-one | −0.064 | −31.992 |
| 945 | (Z)-3-(5-((7-imino-5-oxo-2-(o-tolyloxy)methyl)-5H-[1,3,4]thiadiazolo[3,2-a]pyrimidin-6(7H)-ylidene)methyl)furan-2-yl)benzoic acid | −0.064 | −31.174 |
| 950 | (2Z,5Z)-3-phenyl-2-(phenylimino)-5-((5-(3-(trifluoromethyl)phenyl)furan-3-yl)methylene)thiazolidin-4-one | −0.064 | −31.467 |
| 955 | (E)-5-((1-(2-chlorobenzyl)indolin-5-yl)methylene)-6-hydroxy-3-(naphthalen-1-yl)-2-thioxo-2,3-dihydropyrimidin-4(5H)-one | −0.064 | −33.525 |
| 960 | (Z)-1-(2,4-dichlorobenzoyl)-3-(((2,4-dichlorobenzoyl)oxy)imino)indolin-2-one | −0.064 | −32.562 |
| 965 | 2-(2-(1H-indol-3-yl)ethyl)-3-((2-fluorobenzyl)thio)benzo[4,5]thieno[3,2-d]pyrimidin-1(2H)-one | −0.064 | −31.092 |
| 970 | 2-chloro-5-(5-((Z)-((Z)-4-oxo-3-phenyl-2-(phenylimino)thiazolidin-5-ylidene)methyl)furan-2-yl)benzoic acid | −0.064 | −32.004 |
| 975 | N-(3-methoxyphenyl)-2-((2-(4-methoxyphenyl)-1-oxo-2,9-dihydro-1H-pyrimido[5,4-b]indol-3-yl)thio)acetamide | −0.064 | −31.118 |
| 980 | 9-((2-(4-chlorophenyl)-2-oxoethyl)thio)-8-phenyl-5,6-dihydronaphtho[2',1':4,5]thieno[2,3-d]pyrimidin-7(8H)-one | −0.064 | −32.913 |
| 985 | 5-(2-(acridin-10-ium-3-yl)-1,3-dioxoisoindoline-5-carbonyl)-1-oxo-1H-isoindol-3-olate | −0.064 | −31.840 |
| 990 | ethyl 4-(2-(((3-(4-fluorophenyl)-4-oxo-4,5-dihydro-3H-pyrimido[5,4-b]indol-2-yl)thio)acetamido)benzoate | −0.064 | −32.951 |

TABLE 1-continued

| Rank | Chemical Name | Score/MW | ProPose Score |
|---|---|---|---|
| 995 | methyl 3-((6-chloro-2-(5-(3-(trifluoromethyl)phenyl)furan-2-yl)imidazo[1,2-a]pyridin-1-yl)amino)benzoate | −0.064 | −32.703 |
| 1000 | 2-(benzylthio)-6-(4-((4-fluorobenzyl)oxy)phenyl)-4-(trifluoromethyl)nicotinonitrile | −0.064 | −31.494 |
| 1005 | N-(2-ethoxyphenyl)-2-((2-(4-fluorophenyl)-1-oxo-1,2-dihydrobenzofuro[3,2-d]pyrimidin-3-yl)thio)acetamide | −0.064 | −31.140 |
| 1010 | (Z)-ethyl 3-(((1,3-dioxo-2-(p-tolyl)-2,3-dihydroisoquinolin-4(1H)-ylidene)methyl)amino)-5-(4-fluorophenyl)thiophene-2-carboxylate | −0.064 | −33.459 |
| 1015 | 3-((2-(4-chlorophenyl)-2-oxoethyl)thio)-10-oxo-11-phenethyl-6,7,8,9,10,11-hexahydrobenzo[4,5]thieno[3,2-e][1,2,4]triazolo[4,3-a]pyrimidin-1-ium | −0.064 | −34.050 |
| 1020 | N-(2-chloro-5-(trifluoromethyl)phenyl)-2-((3-(4-ethoxyphenyl)-4-oxo-3,4-dihydroquinazolin-2-yl)thio)acetamide | −0.063 | −33.897 |
| 1025 | (E)-3-((5-(4-bromophenyl)furan-2-yl)methylene)-1-(naphthalen-2-yl)-5-phenyl-1H-pyrrol-2(3H)-one | −0.063 | −32.896 |
| 1030 | (Z)-5-(4-(benzyloxy)-3-methoxybenzylidene)-2-thioxo-3-(3-(trifluoromethyl)phenyl)thiazolidin-4-one | −0.063 | −31.813 |
| 1035 | N-(5-(2-chloro-5-(trifluoromethyl)benzyl)-4-methylthiazol-2-yl)-5-((p-tolyloxy)methyl)furan-2-carboxamide | −0.063 | −33.028 |
| 1040 | 2-((2-(2-chlorobenzyl)-1-oxo-1,2-dihydrobenzo[4,5]thieno[3,2-d]pyrimidin-3-yl)thio)-N-(m-tolyl)acetamide | −0.063 | −32.052 |
| 1045 | 2,2'-disulfanediylbis(3-phenylquinazolin-4(3H)-one) | −0.063 | −32.056 |
| 1050 | N-(3-(6-(2,5-dimethoxyphenyl)pyridin-2-yl)phenyl)-2,3,4,5,6-pentafluorobenzamide | −0.063 | −31.652 |
| 1055 | 2-((4-oxo-3-(4-phenoxyphenyl)-3,4-dihydroquinazolin-2-yl)thio)-N-(perfluorophenyl)acetamide | −0.063 | −36.004 |
| 1060 | N-(5-(2-chloro-5-(trifluoromethyl)benzyl)-4-methylthiazol-2-yl)-5-(phenoxymethyl)furan-2-carboxamide | −0.063 | −32.023 |
| 1065 | 6,6'-([1,1'-biphenyl]-2,2'-diylbis(oxy))bis(benzo[de]isochromene-1,3-dione) | −0.063 | −36.516 |
| 1070 | 5-((5-(2,5-dichlorophenyl)furan-2-yl)methylene)-1,3-diphenyl-2-thioxodihydropyrimidine-4,6(1H,5H)-dione | −0.063 | −32.767 |
| 1075 | 2-((2-(9H-fluoren-2-yl)-2-oxoethyl)thio)-6-(4-methoxyphenyl)-4-(trifluoromethyl)nicotinonitrile | −0.063 | −32.556 |
| 1080 | (E)-2-((3-(4-chlorophenyl)-4-oxo-3,4-dihydroquinazolin-2-yl)thio)-N'-((2-hydroxynaphthalen-1-yl)methylene)acetohydrazide | −0.063 | −32.373 |
| 1085 | (E)-5-(5-chloro-2-((3-chlorobenzyl)oxy)benzylidene)-3-(2-chloro-6-fluorobenzyl)thiazolidine-2,4-dione | −0.063 | −32.898 |
| 1090 | (Z)-2-(1-(2-chlorobenzyl)-1H-benzo[d]imidazol-2-yl)-1-(4-fluorophenyl)vinyl 4-fluorobenzoate | −0.063 | −31.578 |
| 1095 | ethyl 4-(2-chlorophenyl)-2-(2-(furan-2-yl)quinoline-4-carboxamido)thiophene-3-carboxylate | −0.063 | −31.618 |
| 1100 | 9-((2-(4-chlorophenyl)-2-oxoethyl)thio)-8-(m-tolyl)-5,6-dihydronaphtho[2',1':4,5]thieno[2,3-d]pyrimidin-7(8H)-one | −0.063 | −33.235 |
| 1105 | 2-((1-oxo-2-(pyridin-4-ylmethyl)-1,2,6,7,8,9-hexahydrobenzo[4,5]thieno[2,3-d]pyrimidin-3-yl)thio)-N-(2-(trifluoromethyl)phenyl)acetamide | −0.063 | −33.322 |
| 1110 | 3-(5-(benzyloxy)-2,4-dichlorophenyl)-2-(benzylthio)quinazolin-4(3H)-one | −0.063 | −32.614 |
| 1115 | dimethyl 5-(1-hydroxy-4-((perfluorophenyl)thio)-2-naphthamido)isophthalate | −0.063 | −36.175 |
| 1120 | N-(2-benzoyl-4-chlorophenyl)-2-((3-cyano-6-phenyl-4-(trifluoromethyl)pyridin-2-yl)thio)acetamide | −0.063 | −34.591 |
| 1125 | 4-((1-oxo-3-((2-oxo-2-((2-(trifluoromethyl)phenyl)amino)ethyl)thio)-6,7,8,9-tetrahydrobenzo[4,5]thieno[2,3-d]pyrimidin-2(1H)-yl)methyl)pyridin-1-ium | −0.063 | −33.280 |
| 1130 | (3aS,6aS)-3-(2-naphthoyl)-5-(4-bromophenyl)-1-(4-chlorophenyl)-1,6a-dihydropyrrolo[3,4-c]pyrazole-4,6(3aH,5H)-dione | −0.063 | −34.965 |
| 1135 | (Z)-4-chloro-3-(5-((3-(2-((4-chlorophenyl)amino)-2-oxoethyl)-2,4-dioxothiazolidin-5-ylidene)methyl)furan-2-yl)benzoic acid | −0.063 | −32.299 |
| 1140 | N-(2-benzoyl-4-bromo-9,10-dioxo-9,10-dihydroanthracen-1-yl)-2-chlorobenzamide | −0.063 | −34.064 |
| 1145 | N-((2-(5-chloronaphthalen-1-yl)benzo[d]oxazol-5-yl)carbamothioyl)-5-(3-nitrophenyl)furan-2-carboxamide | −0.062 | −35.559 |
| 1150 | N-(3-((4-chloro-1H-pyrazol-1-yl)methyl)phenyl)-3-phenyl-1-(trifluoromethyl)-3H-thieno[2,3-c]pyrazole-5-carboxamide | −0.062 | −31.345 |
| 1155 | (Z)-5-(3-(2,4-dinitrophenoxy)benzylidene)-2-thioxo-3-(3-(trifluoromethyl)phenyl)thiazolidin-4-one | −0.062 | −34.176 |
| 1160 | (E)-3-(3-((5-(2,5-dichlorophenyl)furan-2-yl)methylene)-2-oxo-5-phenyl-2,3-dihydro-1H-pyrrol-1-yl)benzoic acid | −0.062 | −31.263 |
| 1165 | (Z)-ethyl 3-(((1,3-dioxo-2-(3-(trifluoromethyl)phenyl)-2,3-dihydroisoquinolin-4(1H)-ylidene)methyl)amino)benzofuran-2-carboxylate | −0.062 | −32.425 |
| 1170 | N-(5-chloro-2-phenoxyphenyl)-6-(4-chlorobenzyl)-4-methyl-6H-thieno[2,3-c]pyrazole-2-carboxamide | −0.062 | −31.659 |
| 1175 | 2-oxo-2-(10H-phenothiazin-10-yl)ethyl 4'-(trifluoromethyl)-[1,1'-biphenyl]-2-carboxylate | −0.062 | −31.460 |
| 1180 | (Z)-ethyl 4-(5-((2-(4-methylbenzyl)-3,7-dioxo-3H-thiazolo[3,2-b][1,2,4]triazin-6(7H)-ylidene)methyl)furan-2-yl)benzoate | −0.062 | −31.065 |
| 1185 | 2-((3-cyano-6-(4-((4-fluorobenzyl)oxy)phenyl)-4-(trifluoromethyl)pyridin-2-yl)thio)-N-(4-fluorophenyl)acetamide | −0.062 | −34.516 |

TABLE 1-continued

| Rank | Chemical Name | Score/ MW | ProPose Score |
|---|---|---|---|
| 1190 | 5-((5-(2-bromo-4-methylphenyl)furan-2-yl)methylene)-1,3-diphenyl-2-thioxodihydropyrimidine-4,6(1H,5H)-dione | −0.062 | −33.730 |
| 1195 | 2-(3,5-dichloro-4-(naphthalen-1-ylmethoxy)phenyl)-4,5-diphenyl-1H-imidazole | −0.062 | −32.355 |
| 1200 | N-(4-(2,4-dichlorophenyl)thiazol-2-yl)-2-(3-methoxyphenyl)quinoline-4-carboxamide | −0.062 | −31.397 |
| 1205 | 3-((2-(1-(4-fluorophenyl)-2,5-dimethyl-1H-pyrrol-3-yl)-2-oxoethyl)thio)-2,6-diphenylthieno[2,3-d]pyrimidin-1(2H)-one | −0.062 | −35.055 |
| 1210 | 3-((2-oxo-2-(4-phenylpiperazin-1-yl)ethyl)thio)-2-(3-(trifluoromethyl)phenyl)-2,9-dihydro-1H-pyrimido[5,4-13]indol-1-one | −0.062 | −34.909 |
| 1215 | 3-(4-fluorophenyl)-4-oxo-2-((2-oxo-2-((2,3,4-trifluorophenyl)amino)ethyl)thio)-3,4-dihydroquinazoline-7-carboxylic acid | −0.062 | −31.099 |
| 1220 | 2-((3-cyano-4,5-diphenylfuran-2-yl)amino)-2-oxoethyl 1-chlorobenzo[b]thiophene-2-carboxylate | −0.062 | −31.724 |
| 1225 | 2-([1,1'-biphenyl]-4-yl)-N-(4-(N-(3,4-dimethylisoxazol-5-yl)sulfamoyl)phenyl)quinoline-4-carboxamide | −0.062 | −35.511 |
| 1230 | (E)-1-(6-chloro-2-methyl-4-phenylquinolin-3-yl)-3-(1,3-diphenyl-1H-pyrazol-4-yl)prop-2-en-1-one | −0.062 | −32.495 |
| 1235 | 9-((4-bromobenzyl)thio)-8-(m-tolyl)-5,6-dihydronaphtho[2',1':4,5]thieno[2,3-d]pyrimidin-7(8H)-one | −0.062 | −33.660 |
| 1240 | (E)-2-chloro-5-(3-((5-(3,4-dichlorophenyl)furan-2-yl)methylene)-2-oxo-5-phenyl-2,3-dihydro-1H-pyrrol-1-yl)benzoic acid | −0.062 | −33.012 |
| 1245 | 2-((3-cyano-6-(4-fluorophenyl)-4-phenylpyridin-2-yl)thio)-N-(3-(trifluoromethyl)phenyl)acetamide | −0.062 | −31.244 |
| 1250 | 9-((2-(4-chlorophenyl)-2-oxoethyl)thio)-8-cyclohexyl-5,6-dihydronaphtho[2',1':4,5]thieno[2,3-d]pyrimidin-7(8H)-one | −0.062 | −32.060 |
| 1255 | (Z)-2-((3,4-dichlorobenzyl)thio)-3-(2-(2,4,6-trichlorophenyl)hydrazono)-3H-indole | −0.061 | −31.713 |
| 1260 | N-(9,10-dioxo-9,10-dihydroanthracen-1-yl)-2-((3-(4-fluorophenyl)-4-oxo-3,4-dihydroquinazolin-2-yl)thio)acetamide | −0.061 | −32.916 |
| 1265 | N-(3-chloro-4-methylphenyl)-2-((2-(4-ethoxyphenyl)-1-oxo-2,9-dihydro-1H-pyrimido[5,4-b]indol-3-yl)thio)acetamide | −0.061 | −31.866 |
| 1270 | N-(4-chloro-3-(trifluoromethyl)phenyl)-2-((3-(4-chlorophenyl)-4-oxo-3,4-dihydroquinazolin-2-yl)thio)acetamide | −0.061 | −32.165 |
| 1275 | (E)-2-(((5-(3,4-dichlorophenyl)furan-2-yl)methylene)amino)-N-(2-(trifluoromethyl)phenyl)thiophene-3-carboxamide | −0.061 | −31.219 |
| 1280 | (Z)-2-methoxy-4-((4-oxo-2-thioxo-3-(3-(trifluoromethyl)phenyl)thiazolidin-5-ylidene)methyl)phenyl benzoate | −0.061 | −31.563 |
| 1285 | 3-(5-((4-chlorophenyl)thio)-2-((2-methylbenzyl)thio)pyrimidine-4-carboxamido)benzoic acid | −0.061 | −31.882 |
| 1290 | (Z)-2-(benzo[d]thiazol-2(1H)-ylidene)-4-((3-benzyl-6-(trifluoromethyl)-3H-benzo[d]imidazol-2-yl)thio)-3-oxobutanenitrile | −0.061 | −31.965 |
| 1295 | (1E,NE)-2-cyano-N-(2-hydroxy-4-(trifluoromethyl)-7H-chromen-7-ylidene)-2-(4-(2-oxo-2H-chromen-3-yl)thiazol-2-yl)ethenaminium | −0.061 | −31.078 |
| 1300 | (S,E)-10-((1-(2-chlorobenzyl)-1H-indol-3-yl)methylene)-7-(thiophen-2-yl)-7,10-dihydro-5H-benzo[h]thiazolo[2,3-b]quinazolin-9(6H)-one | −0.061 | −36.038 |
| 1305 | (E)-5-(5-bromo-2-((2-chlorobenzyl)oxy)benzylidene)-3-(2-chloro-6-fluorobenzyl)thiazolidine-2,4-dione | −0.061 | −34.624 |
| 1310 | (R,E)-10-(2-((2-fluorobenzyl)oxy)benzylidene)-7-(3-fluorophenyl)-7,10-dihydro-5H-benzo[h]thiazolo[2,3-b]quinazolin-9(6H)-one | −0.061 | −34.316 |
| 1315 | 2-((3-(4-chlorophenyl)-4-oxo-3,4-dihydroquinazolin-2-yl)thio)-N-(2-methoxydibenzo[b,d]furan-3-yl)acetamide | −0.061 | −33.031 |
| 1320 | (R,Z)-10-(2-((4-chlorobenzyl)oxy)benzylidene)-7-(4-fluorophenyl)-7,10-dihydro-5H-benzo[h]thiazolo[2,3-b]quinazolin-9(6H)-one | −0.061 | −35.272 |
| 1325 | (R,Z)-7-(4-fluorophenyl)-10-(2-(naphthalen-1-ylmethoxy)benzylidene)-7,10-dihydro-5H-benzo[h]thiazolo[2,3-b]quinazolin-9(6H)-one | −0.061 | −36.208 |
| 1330 | (Z)-2-((Z)-5-(2,4-dichlorobenzylidene)-3-(4-fluorophenyl)-4-oxothiazolidin-2-ylidene)-3-oxo-3-(4-propylphenyl)propanenitrile | −0.061 | −32.700 |
| 1335 | (R,Z)-2-(5-((7-(3-methoxyphenyl)-9-oxo-5H-benzo[h]thiazolo[2,3-b]quinazolin-10(6H,7H,9H)-ylidene)methyl)furan-2-yl)benzoic acid | −0.061 | −34.036 |
| 1340 | (S,E)-5-phenyl-2-(3-(4-(5-phenyl-3-(p-tolyl)-4,5-dihydro-1H-pyrazol-1-yl)styryl)phenyl)oxazole | −0.061 | −33.896 |
| 1345 | (E)-methyl 2-chloro-5-(3-((5-(2,5-dichlorophenyl)furan-2-yl)methylene)-2-oxo-5-phenyl-2,3-dihydro-1H-pyrrol-1-yl)benzoate | −0.061 | −33.433 |
| 1350 | 2-(4-ethylphenyl)-N-(4-(N-(4-methylpyrimidin-2-yl)sulfamoyl)phenyl)quinoline-4-carboxamide | −0.061 | −31.766 |
| 1355 | N-(3-chloro-4-methoxyphenyl)-3-(2-chloro-5-(trifluoromethyl)phenyl)-4-oxo-2-thioxo-1,2,3,4-tetrahydroquinazoline-7-carboxamide | −0.061 | −32.768 |
| 1360 | 5-(5-bromo-2-hydroxybenzoyl)-N,1-bis(2-fluorophenyl)-2-oxo-1,2-dihydropyridine-3-carboxamide | −0.061 | −31.773 |
| 1365 | 4-((5-hydroxy-2-oxo-1-(3-(trifluoromethyl)benzyl)-2,3-dihydro-1H-imidazol-4-yl)methylene)-1-phenyl-3-(thiophen-2-ylmethyl)-1H-pyrazol-5(4H)-one | −0.061 | −31.643 |
| 1370 | (Z)-3-(5-((1-(3,4-dichlorobenzyl)-1H-indol-3-yl)methylene)-4-oxo-2-thioxothiazolidin-3-yl)benzoic acid | −0.061 | −32.583 |
| 1375 | 1-(4-bromophenyl)-6-(4-((2-fluorobenzyl)oxy)phenyl)-3-methyl-4-(trifluoromethyl)-1H-pyrazolo[3,4-b]pyridine | −0.060 | −33.631 |

TABLE 1-continued

| Rank | Chemical Name | Score/MW | ProPose Score |
|---|---|---|---|
| 1380 | N-(2-chloro-5-(trifluoromethyl)phenyl)-2-((1-oxo-2,6-diphenyl-1,2-dihydrothieno[2,3-d]pyrimidin-3-yl)thio)acetamide | −0.060 | −34.554 |
| 1385 | (S)-2-((4-chloro-2-(trifluoromethyl)phenyl)amino)-2-oxo-1-phenylethyl 1-chlorobenzo[b]thiophene-2-carboxylate | −0.060 | −31.646 |
| 1390 | N-(4-chlorophenyl)-2-((3-cyano-6-(4-((4-fluorobenzyl)oxy)phenyl)-4-(trifluoromethyl)pyridin-2-yl)thio)acetamide | −0.060 | −34.501 |
| 1395 | N,N'-(1,2-phenylene)bis(1-chloro-5-methoxybenzo[b]thiophene-2-carboxamide) | −0.060 | −33.603 |
| 1400 | N-(2,5-dichlorophenyl)-2-((4-oxo-3-(4-phenoxyphenyl)-3,4-dihydroquinazolin-2-yl)thio)acetamide | −0.060 | −33.030 |
| 1405 | 2-((3-(4-bromophenyl)-4-oxo-3,4-dihydroquinazolin-2-yl)thio)-N-(3-chloro-4-fluorophenyl)acetamide | −0.060 | −31.240 |
| 1410 | N-(3,5-dimethylphenyl)-2-((1-oxo-2-(3-(trifluoromethyl)phenyl)-2,9-dihydro-1H-pyrimido[5,4-b]indol-3-yl)thio)acetamide | −0.060 | −31.441 |
| 1415 | N-(2-bromo-4,6-difluorophenyl)-2-((3-(4-methoxyphenyl)-4-oxo-3,4-dihydroquinazolin-2-yl)thio)acetamide | −0.060 | −32.023 |
| 1420 | N-(4-(2,4-dichlorophenyl)thiazol-2-yl)-2-(4-ethoxyphenyl)quinoline-4-carboxamide | −0.060 | −31.299 |
| 1425 | (Z)-3-(5-((1-(2,4-dichlorobenzyl)-1H-indol-3-yl)methylene)-4-oxo-2-thioxothiazolidin-3-yl)benzoic acid | −0.060 | −32.346 |
| 1430 | N2,N7-bis(4-chlorophenyl)-9-oxo-9H-fluorene-2,7-disulfonamide | −0.060 | −33.572 |
| 1435 | 2-((3-(4-bromophenyl)-4-oxo-3,4-dihydroquinazolin-2-yl)thio)-N-(4-chloro-3-(trifluoromethyl)phenyl)acetamide | −0.060 | −34.099 |
| 1440 | (Z)-2-(3-methoxybenzylidene)-3-oxo-2,3-dihydrobenzofuran-6-yl 5-methoxy-2-phenylbenzofuran-3-carboxylate | −0.060 | −31.066 |
| 1445 | N-(3-chloro-1,4-dioxo-1,4-dihydronaphthalen-2-yl)-4-(2-(((1,2-dioxo-1,2-dihydronaphthalen-4-yl)amino)phenyl)-2-hydroxy-4-oxobut-2-enamide | −0.060 | −33.026 |
| 1450 | 5-butoxy-N-(2-(3-chloro-4-methoxybenzoyl)benzofuran-3-yl)-2-methylbenzofuran-3-carboxamide | −0.060 | −31.784 |
| 1455 | 2-([1,1'-biphenyl]-4-yl)-N-(3-(N-methyl-N-phenylsulfamoyl)phenyl)quinoline-4-carboxamide | −0.060 | −34.002 |
| 1460 | (E)-3-(3,4-bis(benzyloxy)phenyl)-2-(4-(3-nitrophenyl)thiazol-2-yl)acrylonitrile | −0.060 | −32.527 |
| 1465 | bis(2-(naphthalen-2-yl)-2-oxoethyl) [1,1'-biphenyl]-2,2'-dicarboxylate | −0.060 | −34.456 |
| 1470 | (Z)-5-((4-bromo-5-((4-chlorophenyl)thio)furan-2-yl)methylene)-1-(4-fluorophenyl)-2-thioxodihydropyrimidine-4,6(1H,5H)-dione | −0.060 | −32.007 |
| 1475 | 5,6,11,12-tetraphenyltetracene | −0.059 | −31.681 |
| 1480 | (S)-2-(3-(2-(5-(4-fluorophenyl)-3-(thiophen-2-yl)-4,5-dihydro-1H-pyrazol-1-yl)thiazol-4-yl)phenyl)isoindoline-1,3-dione | −0.059 | −32.707 |
| 1485 | N-(1-chloro-9,10-dioxo-9,10-dihydroanthracen-2-yl)-2-(4-fluorophenylsulfonamido)benzamide | −0.059 | −31.761 |
| 1490 | (Z)-3-(3,4-difluorobenzyl)-5-(4-(4-(furan-2-carbonyl)piperazine-1-carbonyl)benzylidene)thiazolidine-2,4-dione | −0.059 | −31.897 |
| 1495 | (S,Z)-5-(4-chlorobenzylidene)-2-(5-(4-methoxyphenyl)-3-(naphthalen-2-yl)-4,5-dihydro-1H-pyrazol-1-yl)thiazol-4(5H)-one | −0.059 | −31.078 |
| 1500 | 3-(5-((E)-((Z)-2-((4-bromo-2-chlorophenyl)imino)-4-oxothiazolidin-5-ylidene)methyl)furan-2-yl)-4-chlorobenzoic acid | −0.059 | −31.850 |
| 1505 | 1,3-bis((6-phenylthieno[2,3-d]pyrimidin-1-yl)oxy)benzene | −0.059 | −31.440 |
| 1510 | N-(4-fluorobenzyl)-11-oxo-10-(4-(trifluoromethyl)benzyl)-10,11-dihydrodibenzo[b,f][1,4]thiazepine-8-carboxamide | −0.059 | −31.778 |
| 1515 | 2,2'-(quinoxaline-2,3-diylbis(4,1-phenylene))bis(1-(4-fluorophenyl)ethane-1,2-dione) | −0.059 | −34.476 |
| 1520 | (E)-3-(1-(2-chloro-5-(trifluoromethyl)phenyl)-2,5-dimethyl-1H-pyrrol-3-yl)-2-(4-oxo-1,4,5,6,7,8-hexahydrobenzo[4,5]thieno[2,3-d]pyrimidin-2-yl)acrylonitrile | −0.059 | −31.289 |
| 1525 | (Z) - N-(2-2-chloro-4,5-difluorophenyl)benzo[d]oxazol-5-yl)carbamothioyl)-5-(2,5-dichlorophenyl)furan-2-carbimidate | −0.059 | −34.163 |
| 1530 | N-(6-methylbenzo[d]thiazol-2-yl)-2-((2-(4-nitrophenyl)-1-oxo-2,9-dihydro-1H-pyrimido[5,4-b]indol-3-yl)thio)acetamide | −0.059 | −32.067 |
| 1535 | N-(3-cyano-4-(2,4-dichlorophenyl)-5-methylthiophen-2-yl)-2-(3-ethoxyphenyl)quinoline-4-carboxamide | −0.059 | −32.971 |
| 1540 | (Z)-2-(2-(3-((2-chlorobenzyl)oxy)phenyl)-1-phenyl-1H-pyrazol-4-yl)-1-cyanovinyl)quinazolin-4-olate | −0.059 | −32.753 |
| 1545 | (E)-2-(4-((3,4-dichlorobenzyl)oxy)styryl)-3-(3-(trifluoromethyl)phenyl)quinazolin-4(3H)-one | −0.059 | −33.473 |
| 1550 | N-(5-benzyl-3-carbamoylthiophen-2-yl)-5-(5-chlorothiophen-2-yl)-7-(trifluoromethyl)pyrazolo[1,5-a]pyrimidine-2-carboxamide | −0.059 | −33.133 |
| 1555 | 4,4'-oxybis(N-(4-(pyridin-2-yl)thiazol-2-yl)benzamide) | −0.059 | −33.945 |
| 1560 | (S)-3,3-bis(4-chlorophenyl)-3',5'-diphenyl-3H,3'H-spiro[benzo[c]thiophene-1,2'-[1,3,4]thiadiazole] | −0.059 | −34.203 |
| 1565 | N-(4-(6-methylbenzo[d]thiazol-2-yl)phenyl)-2-((4-oxo-3-(p-tolyl)-3,4-dihydroquinazolin-2-yl)thio)acetamide | −0.059 | −32.238 |
| 1570 | (E)-2-((6-((2-chloro-6-fluorobenzylidene)amino)benzo[d]thiazol-2-yl)thio)-N-(dibenzo[b,d]furan-3-yl)acetamide | −0.059 | −32.060 |
| 1575 | 2-((2-(1-(4-chlorophenethyl)-2,5-dimethyl-1H-pyrrol-3-yl)-2-oxoethyl)thio)-3-(4-fluorophenyl)quinazolin-4(3H)-one | −0.059 | −32.021 |

TABLE 1-continued

| Rank | Chemical Name | Score/ MW | ProPose Score |
|---|---|---|---|
| 1580 | N-(4-(benzyloxy)phenyl)-2-((7-chloro-4-oxo-3-(p-tolyl)-3,4-dihydroquinazolin-2-yl)thio)acetamide | −0.059 | −31.771 |
| 1585 | 3-((2-(4-bromophenyl)-2-oxoethyl)thio)-10-oxo-11-phenethyl-6,7,8,9,10,11-hexahydrobenzo[4,5]thieno[3,2-e][1,2,4]triazolo[4,3-a]pyrimidin-1-ium | −0.059 | −34.020 |
| 1590 | 5-(5-chlorothiophen-2-yl)-N-(3-(cyclohexylcarbamoyl)-4-ethyl-5-methylthiophen-2-yl)-7-(trifluoromethyl)pyrazolo[1,5-a]pyrimidine-2-carboxamide | −0.059 | −34.905 |
| 1595 | 3-((E)-1-((Z)-((4E,5Z)-3-phenyl-4,5-bis(phenylimino)thiazolidin-2-ylidene)hydrazono)ethyl)-2H-chromen-2-one | −0.058 | −31.674 |
| 1600 | 2,2',3,3'-tetraphenyl-7,7'-biquinoxaline | −0.058 | −32.880 |
| 1605 | (E)-5-(5-bromo-2-((4-chlorobenzyl)oxy)benzylidene)-3-(2,6-dichlorobenzyl)thiazolidine-2,4-dione | −0.058 | −34.072 |
| 1610 | 1-(4-bromophenyl)-6-(4-((2-chlorobenzyl)oxy)phenyl)-3-methyl-4-(trifluoromethyl)-1H-pyrazolo[3,4-b]pyridine | −0.058 | −33.400 |
| 1615 | (E) - N-(5-(4-bromobenzyl)thiazol-2-yl)-2-cyano-3-(5-(3-nitrophenyl)furan-2-yl)acrylamide | −0.058 | −31.195 |
| 1620 | 6-(5-chloro-3-(9-chloro-5H-chromeno[4,3-b]pyridin-3-yl)benzofuran-2-carbonyl)-4-methyl-2H-benzo[b][1,4]oxazin-3(4H)-one | −0.058 | −32.461 |
| 1625 | N-(4-chloro-3-(trifluoromethyl)phenyl)-2-((2-(4-methoxyphenyl)-1-oxo-1,2,6,7,8,9-hexahydrobenzo[4,5]thieno[2,3-d]pyrimidin-3-yl)thio)acetamide | −0.058 | −33.749 |
| 1630 | N1,N3-bis(3-(benzo[d]oxazol-2-yl)phenyl)isophthalamide | −0.058 | −32.003 |
| 1635 | (E)-3-((5-(4-bromophenyl)furan-2-yl)methylene)-1-(2,4-dichlorophenyl)-5-phenyl-1H-pyrrol-2(3H)-one | −0.058 | −31.219 |
| 1640 | 2-((3-(4-bromophenyl)-4-oxo-3,4-dihydroquinazolin-2-yl)thio)-N-(3,5-dichlorophenyl)acetamide | −0.058 | −31.067 |
| 1645 | N-(5-(4-chlorophenyl)-1,2,4-thiadiazol-3-yl)-2-((3-cyano-4-(4-methoxyphenyl)-6-phenylpyridin-2-yl)thio)acetamide | −0.058 | −33.072 |
| 1650 | 3-(5-((4-(4-carboxyphenoxy)phenyl)sulfonyl)-1,3-dioxoisoindolin-2-yl)benzoic acid | −0.058 | −31.387 |
| 1655 | (Z) - N-(2-((5-ethyl-4-(4-phenoxyphenyl)thiazol-2-yl)carbamoyl)-3H-benzo[f]chromen-3-ylidene)benzenaminium | −0.058 | −34.454 |
| 1660 | N-(3-(N-(2-chlorophenyl)sulfamoyl)phenyl)-2-(4-methoxyphenyl)quinoline-4-carboxamide | −0.058 | −31.504 |
| 1665 | (E)-2-((2-(1-(4-chlorobenzyl)-1H-pyrazole-3-carbonyl)hydrazono)methyl)phenyl 1-chlorobenzo[b]thiophene-2-carboxylate | −0.058 | −31.789 |
| 1670 | N-(3-(N-(2-chlorophenyl)sulfamoyl)-4-methylphenyl)-2-(4-methoxyphenyl)quinoline-4-carboxamide | −0.058 | −32.262 |
| 1675 | (R,Z) - N-(2-chlorophenyl)-2-cyano-2-(5-(2,5-dichlorobenzyl)-4-oxo-3-(p-tolyl)thiazolidin-2-ylidene)acetamide | −0.058 | −31.352 |
| 1680 | N-(2-methoxy-4-(3-(5-(3-nitrophenyl)furan-2-carbonyl)thioureido)phenyl)benzofuran-2-carboxamide | −0.058 | −32.119 |
| 1685 | di(naphthalen-2-yl) 9H-fluorene-2,7-disulfonate | −0.058 | −33.372 |
| 1690 | (Z)-5-chloro-N-(4-(1-(2-(8-chloro-2-phenylquinoline-4-carbonyl)hydrazono)ethyl)phenyl)thiophene-2-carboxamide | −0.058 | −32.246 |
| 1695 | N-(2-chloro-5-(trifluoromethyl)phenyl)-2-((1-oxo-2-(p-tolyl)-1,2,6,7,8,9-hexahydrobenzo[4,5]thieno[2,3-d]pyrimidin-3-yl)thio)acetamide | −0.058 | −32.495 |
| 1700 | (S,E)-10-(3,5-dichloro-2-hydroxybenzylidene)-7-(2,4-dichlorophenyl)-7,10-dihydro-5H-benzo[h]thiazolo[2,3-b]quinazolin-9(6H)-one | −0.058 | −33.002 |
| 1705 | (S)-4-(5-(4-(dimethylamino)phenyl)-1-(4-nitrophenyl)-4,5-dihydro-1H-pyrazol-3-yl)-7H-benzo[de]benzo[4,5]imidazo[2,1-a]isoquinolin-7-one | −0.057 | −33.363 |
| 1710 | 4,4'-oxybis(N-(5-fluorobenzo[d]thiazol-2-yl)benzamide) | −0.057 | −32.065 |
| 1715 | 2-((2-(4-chlorophenyl)-1-oxo-1,2,6,7,8,9-hexahydrobenzo[4,5]thieno[2,3-d]pyrimidin-3-yl)thio)-N-(2-(trifluoromethyl)phenyl)acetamide | −0.057 | −31.544 |
| 1720 | 2-((3-cyano-6-(4-methoxyphenyl)-4-(trifluoromethyl)pyridin-2-yl)thio)-N-(2,4,5-trichlorophenyl)acetamide | −0.057 | −31.341 |
| 1725 | (S,Z)-10-((5-(4-chloro-2-nitrophenyl)furan-2-yl)methylene)-7-(thiophen-2-yl)-7,10-dihydro-5H-benzo[h]thiazolo[2,3-b]quinazolin-9(6H)-one | −0.057 | −32.761 |
| 1730 | (R,E)-10-(2-((2-chlorobenzyl)oxy)benzylidene)-7-(4-chlorophenyl)-7,10-dihydro-5H-benzo[h]thiazolo[2,3-b]quinazolin-9(6H)-one | −0.057 | −34.059 |
| 1735 | N-(2-(3-((2-(benzo[d]thiazol-2-ylamino)-2-oxoethyl)thio)-1H-indol-1-yl)ethyl)-3-(trifluoromethyl)benzamide | −0.057 | −31.683 |
| 1740 | 5-bromo-2-(5-(5-chlorothiophen-2-yl)-7-(trifluoromethyl)pyrazolo[1,5-a]pyrimidine-2-carboxamido)benzoic acid | −0.057 | −31.086 |
| 1745 | N4,N4'-bis(2-chlorophenyl)-[3,3'-biquinoline]-4,4'-dicarboxamide | −0.057 | −32.139 |
| 1750 | (R)-5-(3-(benzyloxy)phenyl)-4-(2,3-dihydrobenzo[b][1,4]dioxine-7-carbonyl)-3-hydroxy-1-(5-methylbenzo[d]thiazol-2-yl)-1H-pyrrol-2(5H)-one | −0.057 | −33.613 |
| 1755 | 2-(2-((3-chloro-4-((1-chloronaphthalen-2-yl)oxy)phenyl)amino)thiazol-4-yl)-8-methoxy-2H-chromen-2-one | −0.057 | −31.994 |
| 1760 | N2,N6-bis(2-(benzo[d]thiazol-2-yl)phenyl)pyridine-2,6-dicarboxamide | −0.057 | −33.245 |
| 1765 | 3-((2-(2,5-dimethyl-1-(p-tolyl)-1H-pyrrol-3-yl)-2-oxoethyl)thio)-2,6-diphenylthieno[2,3-d]pyrimidin-1(2H)-one | −0.057 | −31.964 |
| 1770 | (Z)-2-(2-(3-(3-((4-chlorobenzyl)oxy)phenyl)-1-phenyl-1H-pyrazol-4-yl)-1-cyanovinyl)quinazolin-4-olate | −0.057 | −31.539 |
| 1775 | N1,N3-di(naphthalen-2-yl)-N1,N3-diphenylisophthalamide | −0.057 | −32.254 |
| 1780 | (N,N'E,N,N'Z) - N,N'-((Z)-2-((E)-(anthracen-9-ylmethylene)hydrazono)-3-phenylthiazolidine-4,5-diylidene)dianiline | −0.057 | −31.682 |

TABLE 1-continued

| Rank | Chemical Name | Score/MW | ProPose Score |
|---|---|---|---|
| 1785 | (S)-(2-((difluoromethyl)thio)phenyl)(6-methoxy-1-(5-(2-(trifluoromethyl)phenyl)furan-2-yl)-3,4-dihydro-1H-pyrido[3,4-b]indol-2(9H)-yl)methanone | −0.057 | −33.843 |
| 1790 | N2,N5-bis(1-ethyl-2-oxo-1,2-dihydrobenzo[cd]indol-6-yl)thiophene-2,5-dicarboxamide | −0.057 | −31.688 |
| 1795 | (R)-1-(3,4-dimethoxyphenyl)-3-((1-oxo-2-(m-tolyl)-1,2,6,7,8,9-hexahydrobenzo[4,5]thieno[2,3-d]pyrimidin-3-yl)thio)pyrrolidine-2,5-dione | −0.056 | −31.706 |
| 1800 | (9H-fluorene-9,9-diyl)bis(4,1-phenylene) bis(2-fluorobenzoate) | −0.056 | −33.529 |
| 1805 | 11-chloro-N-(1-(2,4-dichlorobenzyl)-1H-pyrazol-4-yl)-7-(trifluoromethyl)-5,6-dihydrobenzo[h]pyrazolo[5,1-b]quinazoline-10-carboxamide | −0.056 | −33.355 |
| 1810 | (8S,8aR,11aS,11bS)-10-(2,5-dichlorophenyl)-9,11-dioxo-N-(3-(trifluoromethyl)phenyl)-8a,9,10,11,11a,11b-hexahydro-8H-pyrrolo[3',4':3,4]pyrrolo[2,1-a]isoquinoline-8-carboxamide | −0.056 | −32.180 |
| 1815 | (R)-4-(benzofuran-2-carbonyl)-3-hydroxy-1-(5-((naphthalen-1-ylmethyl)thio)-1,3,4-thiadiazol-2-yl)-5-phenyl-1H-pyrrol-2(5H)-one | −0.056 | −32.227 |
| 1820 | (R,E)-10-((5-(2,3-dichlorophenyl)furan-2-yl)methylene)-7-(4-fluorophenyl)-7,10-dihydro-5H-benzo[h]thiazolo[2,3-b]quinazolin-9(6H)-one | −0.056 | −32.123 |
| 1825 | 2,2'-(2-(1,2-diphenyl-1H-indol-3-yl)ethene-1,1-diyl)bis(benzo[d]thiazole) | −0.056 | −31.408 |
| 1830 | 2-(3-bromophenyl)-N-(4-(N-(4-methylpyrimidin-2-yl)sulfamoyl)phenyl)quinoline-4-carboxamide | −0.056 | −32.069 |
| 1835 | 6,6'-(carbonylbis(4,1-phenylene))bis(5-phenylpyrazine-2,3-dicarbonitrile) | −0.056 | −32.953 |
| 1840 | (Z)-3-(4-benzylpyridin-1-ium-1-yl)-2-(((4-bromophenyl)sulfonyl)imino)-1-oxo-1,2-dihydronaphthalen-4-olate | −0.056 | −31.191 |
| 1845 | (R)-4-(benzofuran-2-carbonyl)-3-hydroxy-1-(5-((naphthalen-1-ylmethyl)thio)-1,3,4-thiadiazol-2-yl)-5-(p-tolyl)-1H-pyrrol-2(5H)-one | −0.056 | −32.745 |
| 1850 | 2-phenyl-N-(2-(4-(2-phenylquinoline-4-carbonyl)piperazin-1-yl)ethyl)quinoline-4-carboxamide | −0.056 | −32.918 |
| 1855 | 2-(4-chlorophenyl)-2-oxoethyl 2-(4-((3aR,7aR)-1,3-dioxohexahydro-1H-isoindol-2(3H)-yl)phenyl)-6-methylquinoline-4-carboxylate | −0.056 | −31.478 |
| 1860 | (Z)-2-(2,4-dichlorophenyl)-5-((3-(4-ethoxy-3-methylphenyl)-1-phenyl-1H-pyrazol-4-yl)methylene)thiazolo[3,2-b][1,2,4]triazol-6(5H)-one | −0.055 | −31.849 |
| 1865 | (Z)-3-oxo-2-(3,4,5-trimethoxybenzylidene)-2,3-dihydrobenzofuran-6-yl 5-methoxy-2-phenylbenzofuran-3-carboxylate | −0.055 | −32.016 |
| 1870 | (Z)-5-(5-bromo-2-((3,4-dichlorobenzyl)oxy)benzylidene)-3-(4-fluorobenzyl)-2-thioxothiazolidin-4-one | −0.055 | −32.223 |
| 1875 | (1E,NE)-2-(4-(6-bromo-2-oxo-2H-chromen-3-yl)thiazol-2-yl)-2-cyano-N-(2-hydroxy-4-(trifluoromethyl)-7H-chromen-7-ylidene)ethenaminium | −0.055 | −32.406 |
| 1880 | (Z)-2-(2,4-dichlorophenyl)-5-((1-phenyl-3-(4-propoxyphenyl)-1H-pyrazol-4-yl)methylene)thiazolo[3,2-b][1,2,4]triazol-6(5H)-one | −0.055 | −31.645 |
| 1885 | 10-(3-(4-(4-chlorophenyl)thiazol-2-yl)piperazin-1-yl)propyl)-2-(trifluoromethyl)-10H-phenothiazine | −0.055 | −32.346 |
| 1890 | (S)-2-((3-allyl-4-oxo-3,4,5,6,7,8-hexahydrobenzo[4,5]thieno[2,3-d]pyrimidin-2-yl)thio)-N-(2-chloro-5-(trifluoromethyl)phenyl)-2-phenylacetamide | −0.055 | −32.407 |
| 1895 | (R,E)-2-chloro-4-(5-((7-(4-fluorophenyl)-9-oxo-5H-benzo[h]thiazolo[2,3-b]quinazolin-10(6H,7H,9H)-ylidene)methyl)furan-2-yl)benzoic acid | −0.055 | −31.928 |
| 1900 | (E)-4-((2-(1-naphthoyl)hydrazono)methyl)-1,3-phenylene bis(4-chlorobenzoate) | −0.055 | −31.973 |
| 1905 | 2-(5-(2,5-dichlorophenyl)furan-2-yl)-N-(5-(4-fluorobenzyl)thiazol-2-yl)quinoline-4-carboxamide | −0.055 | −31.440 |
| 1910 | N-(9-ethyl-9H-carbazol-3-yl)-1,3-dioxo-2-(3-(trifluoromethyl)phenyl)-2,3-dihydro-1H-benzo[de]isoquinoline-6-carboxamide | −0.055 | −31.523 |
| 1915 | (Z)-2-(2,4-dichlorophenyl)-5-((3-(4-isopropoxy-3-methylphenyl)-1-phenyl-1H-pyrazol-4-yl)methylene)thiazolo[3,2-b][1,2,4]triazol-6(5H)-one | −0.054 | −32.061 |
| 1920 | N-benzyl-N-(2-(2-(naphthalen-2-yl)imidazo[2,1-b]thiazol-5-yl)ethyl)-3-(trifluoromethyl)benzenesulfonamide | −0.054 | −32.201 |
| 1925 | 3-((2-(2,5-dimethyl-1-(3-(trifluoromethyl)phenyl)-1H-pyrrol-3-yl)-2-oxoethyl)thio)-2-phenyl-6,7,8,9-tetrahydrobenzo[4,5]thieno[2,3-d]pyrimidin-1(2H)-one | −0.054 | −32.268 |
| 1930 | (S)-4-(benzofuran-2-carbonyl)-3-hydroxy-5-(5-methylfuran-2-yl)-1-(5-((naphthalen-1-ylmethyl)thio)-1,3,4-thiadiazol-2-yl)-1H-pyrrol-2(5H)-one | −0.054 | −31.424 |
| 1935 | N-(3-(3,4-dichlorophenylsulfonamido)-4-methoxyphenyl)-2-phenylquinoline-4-carboxamide | −0.054 | −31.342 |
| 1940 | N2,N7-di(naphthalen-1-yl)-9-oxo-9H-fluorene-2,7-disulfonamide | −0.054 | −31.920 |
| 1945 | 3-((4-chlorophenyl)thio)-N-(4-((1,3-dioxo-2-(2-(trifluoromethyl)phenyl)isoindolin-6-yl)oxy)phenyl)propanamide | −0.054 | −32.177 |
| 1950 | (Z)-5-((4-bromo-5-((4-chlorophenyl)thio)furan-2-yl)methylene)-3-(2,3-dichlorophenyl)-6-hydroxy-2-thioxo-2,3-dihydropyrimidin-4(5H)-one | −0.054 | −31.592 |
| 1955 | N-((4-(benzo[d]thiazol-2-yl)-3-chlorophenyl)carbamothioyl)-4-((4-chlorobenzyl)oxy)-3-methoxybenzamide | −0.054 | −31.867 |
| 1960 | (Z)-4-(((3-(3-fluorobenzoyl)-4,5,6,7-tetrahydrobenzo[b]thiophen-2-yl)amino)methylene)-2-(3-(trifluoromethyl)phenyl)isoquinoline-1,3(2H,4H)-dione | −0.054 | −31.612 |
| 1965 | sulfonylbis(4,1-phenylene) bis(2,4-dichlorobenzoate) | −0.053 | −31.864 |
| 1970 | (E)-3-((5-(2,5-dichlorophenyl)furan-2-yl)methylene)-1-(3-iodophenyl)-5-phenyl-1H-pyrrol-2(3H)-one | −0.053 | −31.161 |

TABLE 1-continued

| Rank | Chemical Name | Score/ MW | ProPose Score |
|---|---|---|---|
| 1975 | (Z)-4-methyl-N-(2-((5-methyl-4-(4-phenoxyphenyl)thiazol-2-yl)carbamoyl)-3H-benzo[f]chromen-3-ylidene)benzenaminium | −0.053 | −31.587 |
| 1980 | (S,Z)-10-(3-bromo-4-hydroxy-5-nitrobenzylidene)-7-(2-chlorophenyl)-7,10-dihydro-5H-benzo[h]thiazolo[2,3-b]quinazolin-9(6H)-one | −0.053 | −31.495 |
| 1985 | (E) - N-(2-(2-(anthracen-9-ylmethylene)hydrazinyl)-2-oxoethyl)-N-(4-chloro-3-(trifluoromethyl)phenyl)benzenesulfonamide | −0.053 | −31.586 |
| 1990 | N-(2-benzoyl-4-bromophenyl)-5-(4-methoxyphenyl)-7-(trifluoromethyl)pyrazolo[1,5-a]pyrimidine-2-carboxamide | −0.053 | −31.308 |
| 1995 | 6-bromo-N-(4-(2,4-dichlorophenyl)-5-methylthiazol-2-yl)-2-(4-methoxyphenyl)quinoline-4-carboxamide | −0.052 | −31.409 |
| 2000 | (Z)-3-(furan-2-ylmethyl)-5-((3-(4-(naphthalen-1-ylmethoxy)phenyl)-1-phenyl-1H-pyrazol-4-yl)methylene)-2-thioxothiazolidin-4-one | −0.052 | −31.069 |

The entire disclosures of all applications, patents and publications, cited herein and of corresponding European Application No. 13/172575.6, filed Jun. 18, 2013 are incorporated by reference herein.

The invention claimed is:

1. A method for treating cancer, comprising administering to a subject in need thereof an effective amount of a DYRK1B inhibitor, wherein said cancer and/or cells of said cancer do not respond to Smoothened inhibitor therapy, or said cancer is not responsive to inhibition of the G protein-coupled receptor Smoothened, or in said cancer and/or in cells of said cancer the G protein-coupled receptor Smoothened is not responsive to inhibition by Smoothened inhibitors.

2. The method of claim 1, wherein said cancer and/or cells of said cancer do not respond to Smoothened inhibitor therapy.

3. The method of claim 1, wherein said cancer is not responsive to inhibition of the G protein-coupled receptor Smoothened.

4. The method of claim 1, wherein in said cancer and/or in cells of said cancer the G protein-coupled receptor Smoothened is not responsive to inhibition by Smoothened inhibitors.

5. The method of claim 1, wherein said cancer is selected from the group consisting of cancer of the breast, esophagus, gastrointestinal tract, gastro-intestinal stromal tumors, pancreas, prostate, biliary tract, bladder, basal cell carcinoma, medulloblastoma, rhabdomyosarcoma, glioma, small-cell lung cancer, oral squamous cell carcinoma, melanoma, colorectal cancer, non-small cell lung cancer, osteosarcoma, glioblastoma, chronic lymphacytic leukemia, chronic myeloid leukemia, multiple myeloma, acute myeloid leukemia, ovarian cancer, meningioma, Non-NF2 Meningiomas, and liver cancer.

6. The method of claim 1, wherein in said cancer and/or in cells of said cancer the hedgehog signaling pathway is activated.

7. The method of claim 6, wherein in said cancer and/or in cells of said cancer the activation of the hedgehog signaling pathway is independent of signaling by the G protein-coupled receptor Smoothened.

8. The method of claim 1, wherein said DYRK1B inhibitor is a small molecule.

9. The method of claim 1, wherein said DYRK1B inhibitor is a compound of formula (I):

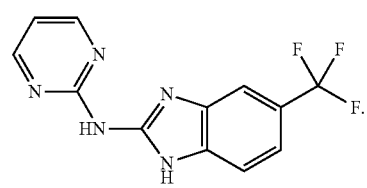

10. The method of claim 1, wherein said subject is a human.

11. The method of claim 1, wherein cancer stem cells are inhibited in said cancer.

12. A method for treating cancer, comprising administering to a subject in need thereof an effective amount of a DYRK1B inhibitor, wherein at least two of the following conditions are satisfied:
  said cancer and/or cells of said cancer do not respond to Smoothened inhibitor therapy, or said cancer is not responsive to inhibition of the G protein-coupled receptor Smoothened, or in said cancer and/or in cells of said cancer the G protein-coupled receptor Smoothened is not responsive to inhibition by Smoothened inhibitors.

13. The method of claim 12, wherein said cancer is selected from the group consisting of cancer of the breast, esophagus, gastrointestinal tract, gastro-intestinal stromal tumors, pancreas, prostate, biliary tract, bladder, basal cell carcinoma, medulloblastoma, rhabdomyosarcoma, glioma, small-cell lung cancer, oral squamous cell carcinoma, melanoma, colorectal cancer, non-small cell lung cancer, osteosarcoma, glioblastoma, chronic lymphacytic leukemia, chronic myeloid leukemia, multiple myeloma, acute myeloid leukemia, ovarian cancer, meningioma, Non-NF2 Meningiomas, and liver cancer.

14. The method of claim 12, wherein said DYRK1B inhibitor is a compound of formula (I):

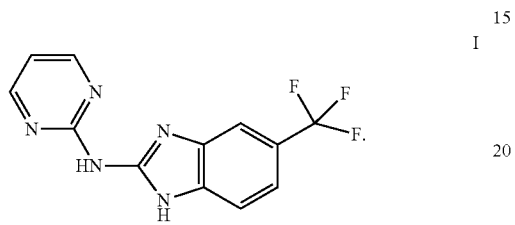

I

* * * * *